(12) United States Patent
Chen et al.

(10) Patent No.: US 8,119,640 B2
(45) Date of Patent: Feb. 21, 2012

(54) HEDGEHOG PATHWAY ANTAGONISTS METHODS OF USE

(75) Inventors: James K. Chen, Mountain View, CA (US); Joel M. Hyman, San Carlos, CA (US); Cory A. Ocasio, San Francisco, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 12/866,338

(22) PCT Filed: Feb. 12, 2009

(86) PCT No.: PCT/US2009/033913
§ 371 (c)(1),
(2), (4) Date: Sep. 27, 2010

(87) PCT Pub. No.: WO2009/102864
PCT Pub. Date: Aug. 20, 2009

(65) Prior Publication Data
US 2011/0015201 A1    Jan. 20, 2011

Related U.S. Application Data

(60) Provisional application No. 61/028,134, filed on Feb. 12, 2008.

(51) Int. Cl.
*A61K 31/495* (2006.01)
(52) U.S. Cl. ........ 514/250; 514/299; 514/306; 514/311; 514/603; 514/637

(58) Field of Classification Search .................. None
See application file for complete search history.

(56) References Cited

FOREIGN PATENT DOCUMENTS
EP    1746100 A1    1/2007
WO    2006122156 A2    11/2006

OTHER PUBLICATIONS

Supplemental EPO search report dated Jul. 20, 2011.
Chemical Abstracts Service, Columbus, Ohio, Jan. 24, 2001 Database accession No. 316361-78-1.
Chemical Abstracts Service, Columbus, Ohio, Aug. 20, 2002 Database accession No. 444316-90-9.
Chemical Abstracts Service, Columbus, Ohio, Feb. 15, 2001 Database accession No. 321863-30-3.
Chemical Abstracts Service, Columbus, Ohio, Sep. 13, 2002 Database accession No. 450382-96-4.
Takahashi, et al., "Structure Activity Relationships of Receptor Binding of 1,4-Dihydropyridine Derivatives," Biological & Pharmaceutical Bulletin, vol. 31, No. 3, Jan. 1, 2008, pp. 473-479.
Chemical Abstracts Service, Columbus, Ohio, Jun. 20, 2003 Database accession No. 534567-13-0.
Pujman, et al., "The Influence of Perathiepine on Leukemia LA VUFB," Neoplasma, Vydavatel 'Sto Slovenskej Akademie Vied Veda, SK. vol. 13, No. 4, Jan. 1, 1966, pp. 411-415.

*Primary Examiner* — Janet Andres
*Assistant Examiner* — Timothy R Rozof
(74) *Attorney, Agent, or Firm* — Thomas, Kayden, Horstemeyer & Risley, LLP

(57) ABSTRACT

The present disclosure provides for compounds, pharmaceutical preparations, kits and methods for the inhibition of the Hh pathway and the alleviation of cancer and developmental disorders associated with the Hh pathway.

5 Claims, 23 Drawing Sheets

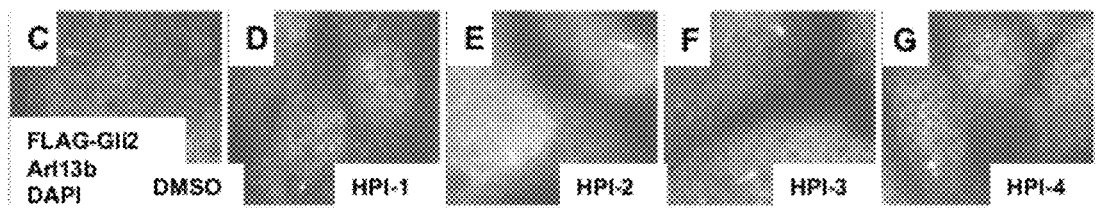
*Fig. 3C*   *Fig. 3D*   *Fig. 3E*   *Fig. 3F*   *Fig. 3G*
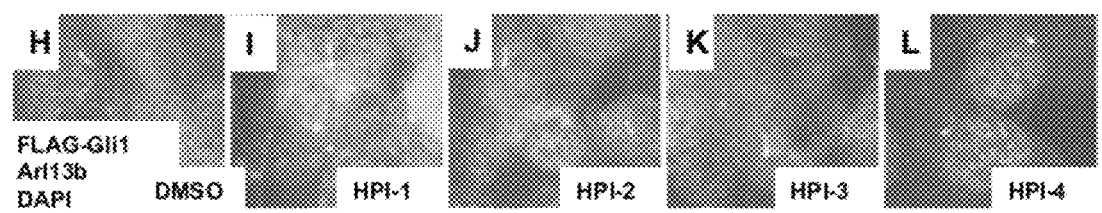
*Fig. 3H*   *Fig. 3I*   *Fig. 3J*   *Fig. 3K*   *Fig. 3L*
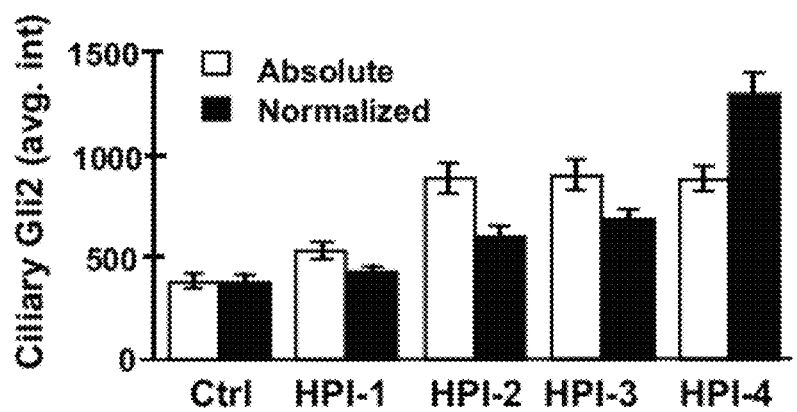
*Fig. 3M*
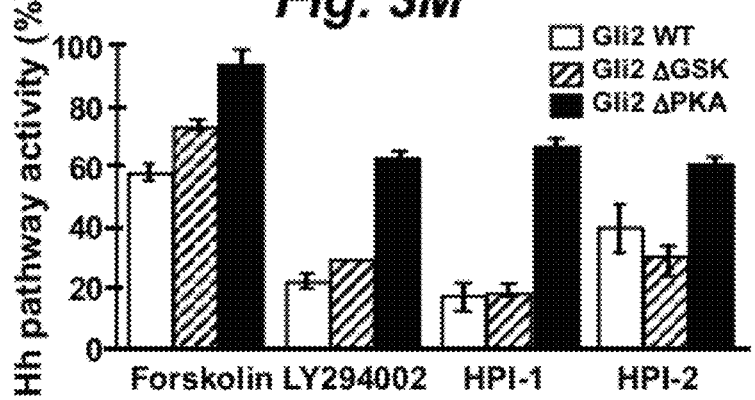
*Fig. 3N*

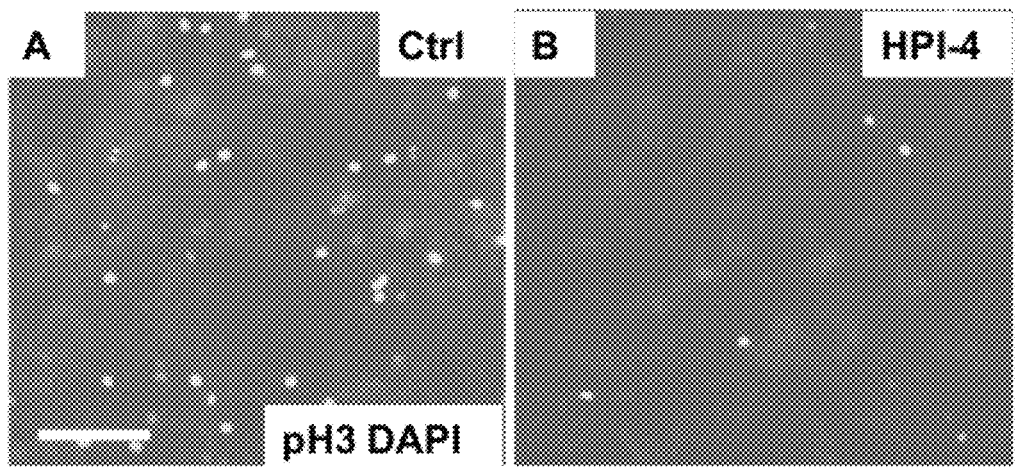
Fig. 4A Fig. 4B
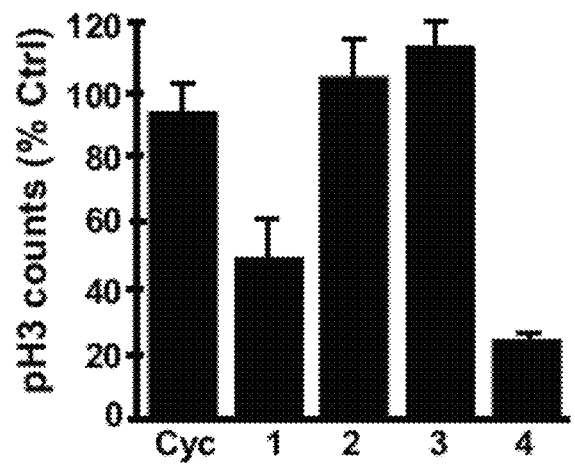
Fig. 4C
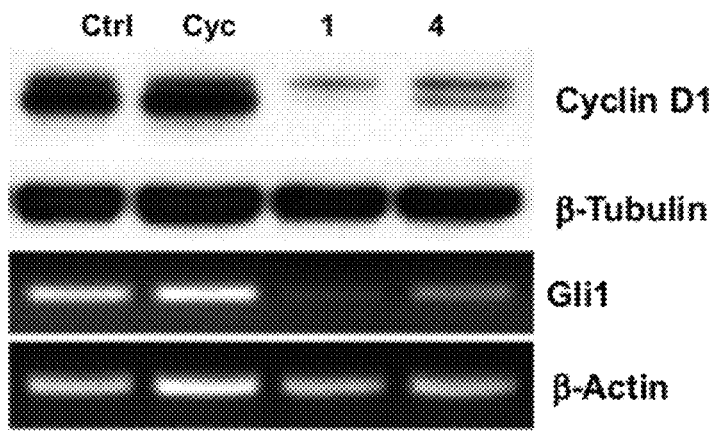
Fig. 4D

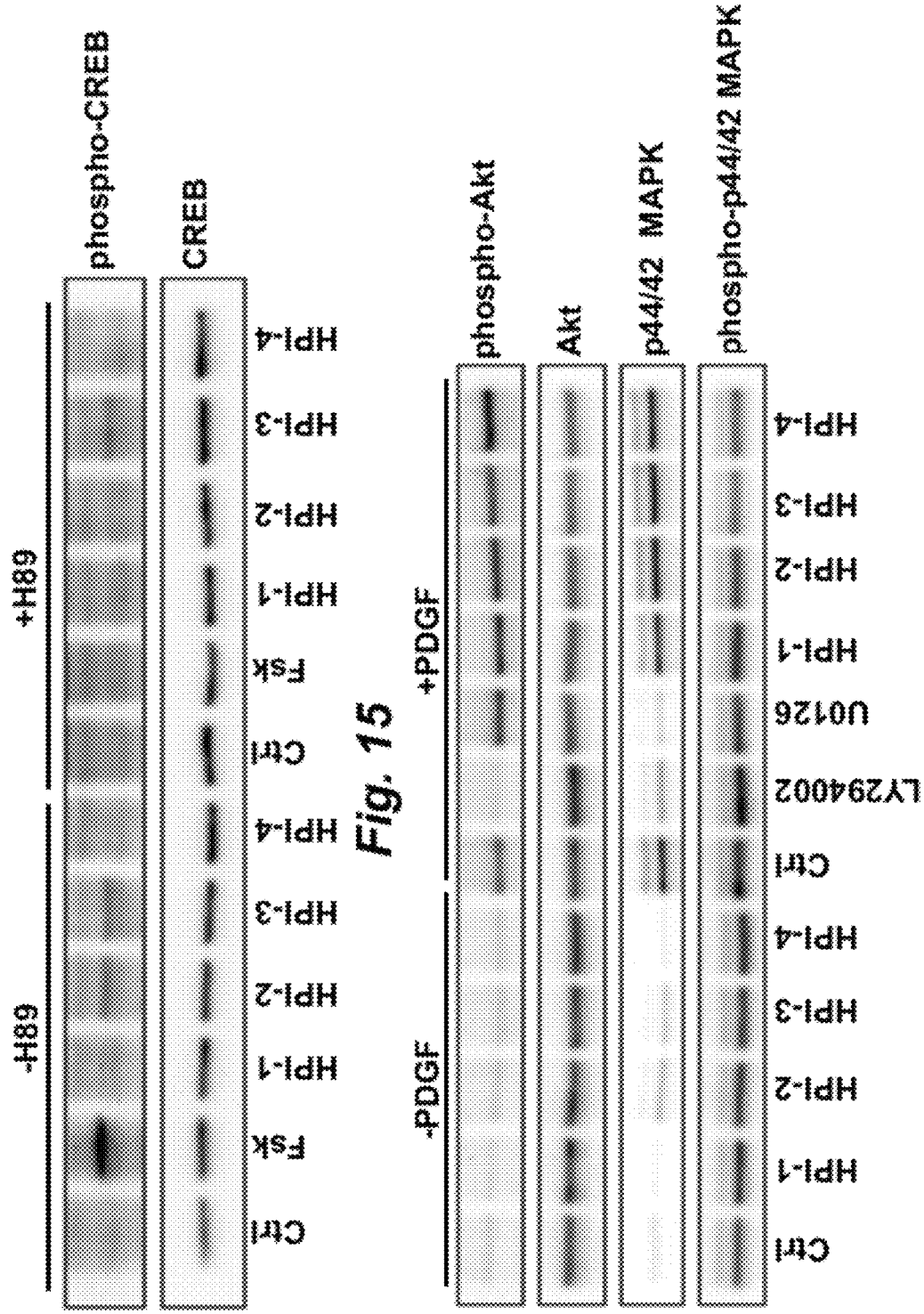

```
SEQ ID NO.: 1
GTACGCTAGCATGGTGAGCAAGGGCGAGCTG
SEQ ID NO.: 2
GTACGTCGACTCACTTGTACAGCTCGTCCATG
SEQ ID NO.: 3
GCGCCTCTCCCACATACTAGAAATCT
SEQ ID NO.: 4
TAGGAAATACCATCTGCTTGGGGTTC
SEQ ID NO.: 5
CACCTGCATGCTAGAGGCAAACTTTT
SEQ ID NO.: 6
TCAGGCCTAGTTAACACTTTGGGACA
SEQ ID NO.: 7
GAATGCGGCCGCGTTCAATCCAATGACTCCAC
SEQ ID NO.: 8
GAAGATCTTTAGGCACTAGAGTTGAGG
SEQ ID NO.: 9
GAATGCGGCCGCGGAGACTTCTGCCCCAGCCC
SEQ ID NO.: 10
GAAGATCTTAGGTCATCATGTTTAAAAAC
SEQ ID NO.: 11
AAAAAGCAGCCTCAGCCACCATGGACTACAAAGACCATGACGGTG
SEQ ID NO.: 12
AGAAAGCTGGGTCTTAGGCACTAGAGTTGAGGAATTG
SEQ ID NO.: 13
AGAAAGCTGGGTCTTAGGTCATCATGTTTAAAAAC
SEQ ID NO.: 14
GGGGACAAGTTTGTACAAAAAAGCAGGCTCA
SEQ ID NO.: 15
GGGGACCACTTTGTACAAGAAAGCTGGGTC
```

*Fig. 21*

HEDGEHOG PATHWAY ANTAGONISTS METHODS OF USE

CROSS-REFERENCE TO RELATED APPLICATIONS

This application claims priority to PCT Application No. US/09/033913, filed Feb. 12, 2009 and entitled "HEDGEHOG PATHWAY ANTAGONISTS AND METHODS OF USE", and which also claims priority to U.S. Provisional Application No. 61/028,134, entitled "HEDGEHOG PATHWAY ANTAGONISTS AND METHODS OF USE" filed on Feb. 12, 2008, the entirety of which is herein incorporated by reference in its entirety.

STATEMENT REGARDING FEDERALLY SPONSORED RESEARCH OR DEVELOPMENT

This disclosure was made with Government support under contract CA136574 awarded by the National Institutes of Health. The Government has certain rights in this invention.

TECHNICAL FIELD

The present disclosure is generally related to compounds antagonistic to the Hedgehog pathway, and derivatives of said compounds. The disclosure further relates to pharmaceutical compositions and methods of using said compositions to modulate cell growth and tissue development.

SEQUENCE LISTING

The present disclosure includes a sequence listing incorporated herein by reference in its entirety.

BACKGROUND

The Hedgehog (Hh) pathway was first discovered in a *Drosophila* genetic screen because of its role in patterning the body of the animal (Nusslein-Volhard et al., Nature (1980) 287:795-801). Shortly afterward, mammalian homologues of the Hedgehog gene were cloned and characterized in chick and mouse (Echelard et al., Cell (1993) 75:1417-1430; Riddle et al., Cell (1993) 75:1401-1416; Roelink et al., Cell (1994) 76:761-775). There are three Hh vertebrate homologues, named Sonic Hedgehog (Shh), Desert Hedgehog (Dhh) and Indian Hedgehog (Ihh), with Shh being implicated in limb development and neural tube development (Bitgood et al., Curr. Biol. (1996) 6:298-304; Chiang et al., Nature (1996) 383:407-413; St. Jacques et al., Genes Dev. (1999) 13:2072-2086; Zhang et al., Cell (2001) 106:781-792). Using both the *Drosophila* and the mouse models to define how the Hh pathway transduced its signal, it was revealed that this is a multifactorial and unconventional pathway (Hooper et al., Nat. Rev. Mol. Cell. Biol. (2005) 6:306-317; Huangfu et al., Dev. (2006) 133:3-14). In vertebrates, signal transduction in Hh pathway begins by the Shh ligand binding to Patched (Ptc1) a 12 transmembrane receptor. Ptc1 is coupled to and represses a signaling polypeptide Smoothened (Smo), a 7 transmembrane, G-protein coupled receptor. In the presence of Shh, the Ptc1 inhibition on Smo is released, and Smo transduces the Shh signal, activating downstream pathway components. However, in the absence of Shh, Ptc1 represses Smo signaling, and no signal transduction takes place.

The final downstream effector of the Hh pathway is the transcription factor Gli. There are 3 Gli proteins in vertebrates, Gli1, Gli2 and Gli3, and the Gli polypeptides take their name from their discovery as genes amplified in glioblastoma (Kinzler et al., Science (1987) 236:70-73; Bai et al, Dev. Cell (2004) 6:103-115; Motoyama et al, Dev. Biol. (2003) 259:150-161). The three Gli proteins share high homology in the zinc finger domain, but have limited homology outside of this region (Matise and Joyner Oncogene (1999) 18: 7852-7859). Gli 1 is a transcriptional activator, while Gli2 and Gli3 are bifunctional and can function as a transcriptional activator or, when proteolytically processed, a transcriptional repressor (Dai et al., J. Biol. Chem. (1999) 12:8143-8152). In general, Gli1 expression is restricted to proliferating cells adjacent to tissues expressing Shh. Gli2 and Gli3 are broadly expressed in proliferating cells exposed to lower concentrations of Shh (Hui et al., Dev. Biol. (1994) 162:402-413).

In the cytoplasm, Gli is complexed with the protein Suppressor of Fused and may be tethered to the microtubule cytoskeleton (Methot and Basler, Dev. (2000) 127:4001-4010; Chen et al., Mol. Cell. Biol. (2005) 25:7042-7053; Preat, Genetics (1992) 132:725-736). Upon transduction of a Shh signal, Gli is released from the complex and migrates to the nucleus. There Gli binds to specific sites in the genome and induces gene expression. It is interesting to note that some of the transcripts produced by the Gli transcription factors are components of the Hh pathway itself, such as Gli1, Ptc1 and Hedgehog interacting protein (Hip).

Disruption of the Hh pathway causes developmental abnormalities in embryogenesis and cancer in the adult. For example, in development, Shh mutations in a mouse model have a dramatic embryonic phenotype with lack of anterior and posterior limb polarity, lack of lung mesoderm and most ventral CNS motorneurons (Chiang et al., Nature (1996) 383:407-413). Mouse models of Ptc1 mutations can be embryonic lethal when homozygous, and display severe developmental defects similar to that of the Shh mutants when heterozygous (Goodrich et al., Science (1997) 277:1109-1113). For the Gli genes, a mouse that is homozygous for a Gli1 mutant with deleted zinc-finger domains develops normally (Matise et al., Development (1998) 125:2759). In contrast, Gli2 mutants without zinc-finger domains show developmental defects in the ventral CNS, lung, vertebrae and bones (Matise et al, supra; Motoyama et al, Nat. Genet. (1998) 20:54-57). Double mutants that are Gli1−/− and Gli2−/+ have a milder phenotype than Gli2−/− and have relatively normal limb development, but die at birth or shortly after. (Park et al., Development (2000) 127:1593-1605). Mice containing a Gli2+/−; Gli3−/− mutant have skeletal abnormalities that are more severe than either mutant alone (Mo et al., Development (1997) 124:113-123).

As mentioned previously, Gli was named for its discovery in brain cancer (glioblastoma). In Basal Cell Nevus Syndrome or Gorlin's syndrome, loss of function of Ptc1 leads to a predisposition to pediatric medulloblastoma and basal cell carcinoma (BCC) of the skin, the most common pediatric brain tumor and the most common type of skin cancer in the Caucasian population (Goodrich and Scott, Neuron (1998) 21:1243-1257). Gli1 overexpression is frequently found in BCC patients with Gorlin's syndrome and in non Gorlin's patients where the BCC has arisen spontaneously (Fan et al, Nat. Med. (1997) 3:788-792). Disruption of the Shh-Gli pathway is has also been described in a number of adult cancers which are discussed in more detail below.

The primary cilium is a hair-like appendage extending from the surface of a cell. This specialized structure, with a unique microtubular cytoskeleton (axoneme) and a surrounding membrane, is assembled and maintained by the intraflagellar transport machinery. Recent work has shown that primary cilia concentrate receptors and signal transduction components that have vital roles in development. In particular, evidence in the developing neural tube and limb bud has shown that genes encoding the IFT motors and the IFT particle subunits are required for Shh signaling. It has been found that the Shh signaling components, Patched (Ptc), Smo, Suppressor of fused and Gli transcription factors, concentrate in primary cilia.

Compounds which specifically affect the Hh pathway are few. Cyclopamine is a steroidal alkaloid derived from plants that antagonizes Smo and is currently in phase I clinical trials (Curis, Cambridge Mass.). Three other compounds have been described to act downstream of Smo in the Hh pathway, but their targets and mechanism of action are currently unclear (Lauth et al., Proc. Natl. Acad. Sci. USA (2007) 104:8455-8460; Lee et al., Chembiochem (2007)8:1916-1919).

Thus the Hh pathway is important for normal development of the embryo and carcinogenesis in the adult, indicating there is a great need for compounds and methods of using such compounds of the present disclosure for the alleviation and study of cancers and developmental disorders of the Hh pathway.

SUMMARY

The present disclosure provides for compounds, pharmaceutical preparations, kits and methods for the inhibition of the Hh pathway and the alleviation of cancer and developmental disorders associated with the Hh pathway.

Briefly described, embodiments of this disclosure, among others, encompass compounds and pharmaceutical formulations thereof are provided for the inhibition of the Hh pathway. One aspect, therefore, of the present disclosure provides compounds according to formula (I):

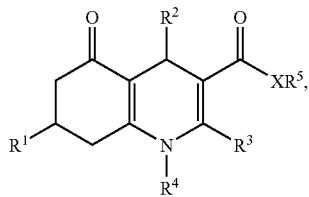

I wherein: $R^1$, $R^2$, $R^3$, and $R^5$ can be independently: H, $CO_2R$, $NO_2$, CN, $SO_2$, SH, SR, OH, OR, $NH_2$, NHR, NRR, an ether group, alky, alkenyl, alkynyl, alkoxy, cycloalkyl, aryl, heterocycloalkyl, or heteroaryl, wherein alkyl, alkenyl, alkynyl, alkoxy, cycloalkyl, heterocycloalkyl, and heteroaryl may be optionally substituted with: $CO_2R$, $NO_2$, CN, $SO_2$, SH, SR, OH, OR, $NH_2$, NHR, NRR, halogen, alkyl, alkenyl, alkynyl, alkoxy, cycloalkyl, aryl, heterocycloalkyl, or heteroaryl; $R^4$ can be: H, $CO_2R$, or alkyl, where alkyl may be optionally substituted with $CO_2R$, $NO_2$, CN, $SO_2$, SH, SR, OH, OR, $NH_2$, NHR, NRR, halogen, alkyl, alkenyl, alkynyl, alkoxy, cycloalkyl, aryl, heterocycloalkyl, or heteroaryl; R can be independently: H; alkyl, cycloalkyl, aryl, heterocycloalkyl, or heteroaryl; and X can be: O, N, or S; or a pharmaceutically acceptable salt thereof.

In the embodiments of this aspect of the disclosure, the compounds are antagonists of the Hedgehog signaling pathway of a cell. In the embodiments of the present disclosure, the compound can be selected from the group consisting of the compounds as shown in FIGS. 20A and 20B, or a pharmaceutically acceptable salt thereof.

Another aspect of the disclosure provides compounds selected from the group consisting of: the compounds as shown in FIG. 19, or a pharmaceutically acceptable salt thereof.

Another aspect of the disclosure provides for pharmaceutical compositions comprising a compound or pharmaceutically acceptable salt thereof according to any one of the above embodiments, and a pharmaceutically acceptable carrier.

Still another aspect of the disclosure is a method of inhibiting Hedgehog pathway signaling in a cell, the method comprising: contacting the cell with a compound as set forth in any one of claims 1-4 in an amount effective to inhibit Hedgehog signaling in the cell; wherein Hedgehog pathway signaling in the cell is inhibited.

Still another aspect of the disclosure provides methods of screening a candidate agent for use as a Hedgehog pathway inhibitor compound (HPI), the method comprising: contacting a cell with a Smo agonist, wherein the cell comprises a heterologous reporter gene construct comprising Gli DNA binding sites operably linked to a region encoding a reporter; contacting the cell with a candidate HPI agent; and detecting a difference in activity of the reporter, wherein a lower level of activity of the reporter marker as compared to a control cell untreated with the candidate HPI is indicative of HPI activity.

Another aspect of the disclosure provides methods of diagnosing cancer in a mammal, the method comprising: contacting a detectably labeled HPI with a test sample of cancer cells suspected of over-expressing a Gli transcription factor; detecting the level of a Gli transcription factor in the test sample of cancer cells obtained from the mammal, wherein a higher level of HPI label detected as compared to a control sample is indicative of cancer in the mammal from which the test sample of cancer cells were obtained.

Yet another aspect of the disclosure provides kits comprising a container and a doses or plurality of doses of a Hedgehog pathway antagonist compound according to any of claims 1-4, and a package insert describing the use and attendant benefits of said compound, or a pharmaceutical composition comprising said compound, in treating a pathological condition of interest.

which compounds include those set forth in Table 1 and Table 2, and pharmaceutically acceptable derivatives thereof. In some embodiments, the compounds do not directly target Smo, i.e. the compounds are not functionally or biochemically competitive with Smoothened antagonist (SAG) or do not bind to Smoothened; act on a target in the Hh pathway other than Smoothened, etc. The compounds provided by the present disclosure are epistatic to Smo, including compounds that can inhibit Hh target gene expression induced by the overexpression of Gli transcription factors.

BRIEF DESCRIPTION OF THE DRAWINGS

Further aspects of the present disclosure will be more readily appreciated upon review of the detailed description of its various embodiments, described below, when taken in conjunction with the accompanying figures. The drawings are described in greater detail in the description and examples below.

FIG. 1A: Hh pathway activation induced by 0.5 μM SAG is resistant to cyclopamine (red) but not forskolin (black). FIG. 1B: Structures of four HPIs identified in the chemical library screen. FIG. 1C: Each of HPI1-HPI-4 inhibits Hh pathway activity induced by Shh-conditioned medium or 0.5 μM SAG with similar potencies. FIGS. 1D-1I: None of the HPIs (20 μM)

inhibits the binding of BODIPYcyclopamine to Smo-overexpressing HEK-293T cells. FIGS. 1J-1L: The HPIs can partially inhibit Shh-dependent accumulation of Smo in the primary cilium, suggesting that they can indirectly alter Smo activity. The HPIs were used at concentrations ten-fold greater than their IC50s in the Shh-LIGHT2 assay or 30 µM, whichever was lower (15 µM HPI-1, 20 µM HPI-2, 30 µM HPI-3, and 30 µM HPI-4). Quantitative data are the average intensity of Smo antibody staining in at least 20 ciliary regions ± s.e.m. Scale bars: D-I, 10 µm; J-K, 5 µm.

FIG. 2A: All four HPIs block the constitutive Hh pathway activity in Su(fu)$^{-/-}$ fibroblasts, as determined by a transfected Gli-dependent firefly luciferase reporter. Doses of 15 µM HPI-1, 20 µM HPI-2, 30 µM HPI-3, and 30 µM HPI-4 were used. FIG. 2B: HPI-1 inhibits Hh pathway activity induced by Gli1 or Gli2 overexpression; HPI-2 preferentially inhibits Gli2; and HPI-3 and HPI-4 are inactive against exogenous Gli1 and Gli2.

FIGS. 3A-3N illustrate the effects of HPIs on Gli processing, stability, and localization. FIG. 3A: Shh-sensitive Gli processing can be recapitulated in clonal NIH-3T3 cells stably expressing FLAG-tagged Gli2. Effects of each HPI on cellular levels of full-length and repressor forms of FLAG-Gli2 are 30 shown, including representative immunoblotting results and the average band intensities from at least four independent experiments ± s.e.m. Quantitative data are normalized with respect to basal levels of full-length FLAG-Gli2 in the control condition. FIGS. 3C-3G: Subcellular localization of FLAG-Gli2 (green) with respect to the primary cilium (red) and nucleus (blue outline) in cells treated with a DMSO vehicle control or individual HPIs. FIGS. 3H-3L: Subcellular localization of FLAG-Gli1 (green) with respect to the primary cilium (red) and nucleus (blue outline) in cells treated with a DMSO vehicle control or individual HPIs. FIG. 3M: Quantification of ciliary FLAG-Gli2 levels observed by immunofluorescence. Data are the average intensity of anti-FLAG antibody staining in at least 60 ciliary regions ± s.e.m, and both absolute ciliary intensities and those normalized with respect to total FLAG-Gli2 levels are shown. Doses of 15 µM HPI-1, 20 µM HPI-2, 30 µM HPI-3, and 30 µM HPI-4 were used. FIG. 3N: Differential inhibition of wildtype, ΔGSK and ΔPKA forms of Gli2 by 50 µM forskolin, 50 µM LY294002, 15 µM HPI-1, or 20 µM HPI-2. Scale bars: C-E, 5 µm; H-I, 10 µm.

FIGS. 4A-4D illustrate the pharmacological blockade of SmoM2-dependent GNP proliferation. FIGS. 4A-3B: Representative anti-pH3 staining of primary GNP cultures treated with DMSO or individual HPIs. Scale bar: 100 µm. FIG. 4C: Quantification of pH3-positive cells upon cyclopamine (Cyc; 5 µM) or HPI treatment (10 µM each), relative to a DMSO control. Data are the average of at least two independent experiments ± s.e.m. FIG. 4D: Effects of cyclopamine, HPI-1, and HPI-4 on cyclin D1 and Gli1 expression, relative to β-tubulin and β-actin controls.

FIGS. 10A-10B: Merge of Smo-CFP (green) and Smo-YFP (red) fluorescence in transfected NIH-3T3 cells before and after the top half of the cell is subjected to YFP photobleaching. FIGS. 10C-10D: False color images of Smo-CFP fluorescence intensities before and after YFP photobleaching, with selected regions within the non-photobleached and photobleached halves indicated by the white and red squares, respectively. FIG. 10E: Close-up view of the white-bordered region in panel C. FIG. 10F: Close-up view of the white-bordered region in panel D. FIG. 10G: Close-up view of the red-bordered region in panel C. FIG. 10H: Close-up view of the red-bordered region in FIG. 10D. FIG. 10I: Percentage of Smo-CFP/Smo-YFP FRET associated with 10 µM cyclopamine, 500 nM SAG, and 10 µM doses of the HPIs. Data are the average of at least 10 cells ± s.d. FIG. 10J: Shh-induced fold change in Smo-CFP/Smo-YFP FRET for each condition.

FIG. 11A: Relative firefly luciferase levels in Shh-LIGHT2 cells transfected for Gli1 or Gli2 overexpression and treated with various doses of HPI-2. FIG. 11B: Corresponding *Renilla* luciferase levels under the same experimental conditions. Data are the average of triplicate samples ± s.d.

FIG. 15 is a digital image of an electrophoretic gel analysis showing that the HPIs of the disclosure do not significantly induce PKA-dependent phosphorylation of CREB. NIH-3T3 cells were treated with individual HPIs in the absence and presence of 10 μM PKA inhibitor H89, and the resulting levels of phosphorylated CREB were determined by immunoblotting. Doses of 15 μM HPI-1, 20 μM HPI-2, 30 μM HPI-3, and 30 μM HPI-4 were tested, and DMSO and 50 μM forskolin (Fsk) were used as negative and positive controls, respectively.

FIG. 16 is a digital image of an electrophoretic gel analysis showing that The HPIs do not inhibit PI3K or MAPK pathway activity. NIH-3T3 cells were treated with individual HPIs in the absence and presence of PDGF BB simulation, and the resulting levels of phosphorylated Akt or phosphorylated p44/p42 MAPK were determined by immunoblotting. Doses of 15 μM HPI-1, 20 μM HPI-2, 30 μM HPI-3, and 30 μM HPI-4 were tested, and 50 μM LY294002 and 10 μM U0126 were used as positive controls.

FIG. 21 shows the nucleotide sequences used a primers.

DETAILED DESCRIPTION

Figure 1A:
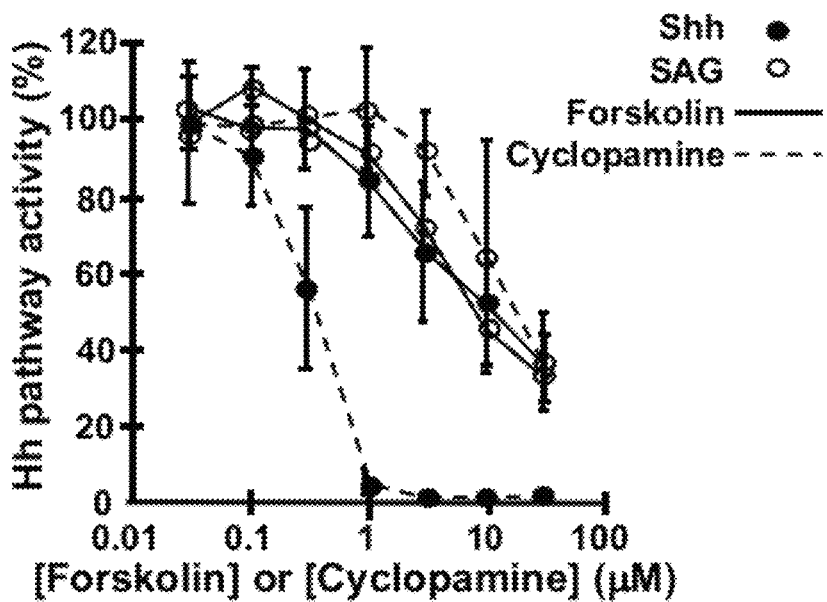
FIGS. 1A-1L illustrate the identification of four Hh pathway inhibitors that do not directly target Smo.

Before the present disclosure described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the exemplary methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a sample" includes a plurality of such samples and reference to "the molecule" includes reference to one or more molecules and equivalents thereof known to those skilled in the art, and so forth.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Definitions

In describing and claiming the disclosed subject matter, the following terminology will be used in accordance with the definitions set forth below.

As used herein, compounds of the disclosure are "Hedgehog Pathway Inhibitors" or "HPIs." It is understood that there is no limitation placed on the term as to a particular Hh pathway gene or polypeptide either known or yet to be discovered, nor is it limited to a Hedgehog pathway gene or polypeptide in a particular species (e.g., human).

As used herein, "HPI-1" refers to a hedgehog pathway inhibitor, 4-(3-Hydroxy-phenyl)-7-(2-methoxy-phenyl)-2-methyl-5-oxo-1,4,5,6,7,8-hexahydro-quinoline-3-carboxylic acid 2-methoxy-ethyl ester.

"Gli transcription factors" or "Gli" as used herein are genes and polypeptides which are effectors of the Hh pathway, and includes Gli1, Gli2 and Gli3, and all variants thereof. In certain cases, examples of Gli genes may be found at least at accession numbers AF316573.1, NM_005270, NM_000168, NM_010296, NM_001081125, X95255.

As used herein, "hedgehog pathway" or "Hh pathway" is not limited to any species, and refers to a signal transduction pathway where a signal is generated by Smoothened (Smo).

The term "antagonist" is used in the broadest sense, and includes any molecule that partially or fully blocks, inhibits, or neutralizes a biological activity of a Hh pathway-associated polypeptide.

"Aryl" refers to an unsaturated hydrocarbon aromatic ring which may be monocyclic, bicyclic, or polycyclic including, but not limited to, phenyl, naphthyl, and anthracene. "Heteroaryl" refers to an aromatic ring in which one or more carbon atoms is replaced by a heteroatom, for example nitrogen, oxygen, and sulfur, which may be monocyclic, bicyclic, or polycyclic including, but not limited to, indole, furan, thiophene, imidazole, benzofuran, and acridine.

"Cycloalkyl" refers to a saturated hydrocarbon ring which may be monocyclic, bicyclic, or polycyclic, including but not limited to, cyclopropyl, cyclobutyl, cyclopentyl, cyclohexyl, cyclohexenyl, and decalin.

"Heterocycloalkyl" refers to a saturated or partially unsaturated cycloalkyl in which one or more carbon atoms is replaced by a heteroatom, for example nitrogen, oxygen, and sulfur, which may be monocyclic, bicyclic, or polycyclic including, but not limited to, morpholine, dioxane, dioxocane, and benzo-1,3-dioxole.

As used herein, "methods known to one of ordinary skill in the art" may be identified though various reference books and databases. Suitable reference books and treatise that detail the synthesis of reactants useful in the preparation of compounds of the present disclosure, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases. Chemicals that are known but not commercially available in catalogs may be prepared by custom chemical synthesis houses, where many of the standard chemical supply houses (e.g., those listed above) provide custom synthesis services.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

The term "pharmaceutically acceptable" as used herein refers to a compound or combination of compounds that while biologically active will not damage the physiology of the recipient human or animal to the extent that the viability of the recipient is comprised. Preferably, the administered compound or combination of compounds will elicit, at most, a temporary detrimental effect on the health of the recipient human or animal is reduced.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Particularly useful inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Organic bases include, but are not limited to, such as isopropylamine, diethylamine, ethanolamine, trimethylamine, dicyclohexylamine, choline and caffeine.

As used herein, the term "IC50" refers to half maximal inhibitory concentration, for example, representing the concentration of an inhibitor that is necessary for 50% inhibition of the target (i.e. the activity of an enzyme, transcription factor, receptor or ligand).

"Purified" as used herein refers to a HPI removed from an environment in which it was produced and is about 60% free, about 75% free, and most usefully about 90% free from other components with which it is naturally associated or with which it was otherwise associated with during production.

The phrases "operably associated" and "operably linked" refer to functionally related nucleic acid sequences. By way of example, a regulatory sequence is operably linked or operably associated with a protein encoding nucleic acid sequence if the regulatory sequence can exert an effect on the expression of the encoded protein. In another example, a promoter is operably linked or operably associated with a protein encoding nucleic acid sequence if the promoter controls the transcription of the encoded protein. While operably associated or operably linked nucleic acid sequences can be contiguous with the nucleic acid sequence that they control, the phrases "operably associated" and "operably linked" are not meant to be limited to those situations in which the regulatory sequences are contiguous with the nucleic acid sequences they control.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

As used herein, "apoptosis" is a process of self-destruction in certain cells, for example, epithelial cells and erythrocytes, that are genetically programmed to have a limited life span or are damaged. Apoptosis can be induced either by a stimulus, such as irradiation or toxic drugs, by removal of a repressor agent, or by activation of a pro-apoptotic pathway. The cells disintegrate into membrane-bound particles that are then eliminated by phagocytosis. Apoptosis is also known as programmed cell death.

The term "conjugate" refers to a HPI that is covalently or non-covalently associated with a molecule or moiety that alters the physical properties of the HPI such as increasing stability and/or facilitate cellular uptake or efficacy of the HPI. The conjugated HPI may have a molecule or moiety attached directly or indirectly through a linker.

Conjugates may contain, for example, amino acids, peptides, polypeptides, proteins, antibodies, antigens, toxins, hormones, lipids, nucleotides, nucleosides, sugars, carbohydrates, polymers such as polyethylene glycol and polypropylene glycol, as well as analogs or derivatives of all of these classes of substances. Additional examples of conjugates are steroids, such as cholesterol, phospholipids, di- and tri-acylglycerols, fatty acids, hydrocarbons that may or may not contain unsaturation or substitutions, enzyme substrates, biotin, digoxigenin, and polysaccharides. Still other examples include thioethers such as hexyl-S-tritylthiol, thiocholesterol, acyl chains such as dodecandiol or undecyl groups, phospholipids such as di-hexadecyl-rac-glycerol, triethylammonium 1,2-di-O-hexadecyl-rac-glycer-o-3-H-phosphonate, polyamines, polyethylene glycol, adamantane acetic acid, palmityl moieties, octadecylamine moieties, hexylaminocarbonyl-oxyc-holesterol, farnesyl, geranyl and geranylgeranyl moieties.

Conjugates can also comprise a detectable label. The term "label" when used herein refers to a detectable compound or composition which is conjugated directly or indirectly to the HPI so as to generate a "labeled" HPI. The label may be detectable by itself (e.g. radioisotope labels or fluorescent labels) or, in the case of an enzymatic label, may catalyze chemical alteration of a substrate compound or composition which is detectable. For example, conjugates can be a HPI covalently attached to a fluorophore. Conjugates may include fluorophores such as TAMRA, BODIPY, Cyanine derivatives such as Cy3 or Cy5, Dabsyl, or any other suitable fluorophore known in the art.

The term "effective amount" refers to a concentration of HPI which results in achieving a particular stated purpose, for example, to cause a decrease in transcription of a gene of interest in the cell. Of particular interest is an effective concentration that provides a decrease greater than or equal to at least about 45% or further decrease, including about 50% or more, about 60% or more, about 70% or more, about 75% or more, about 80% or more decrease in target activity (i.e., transcription) relative to a basal expression level. Target activity may be measured by any method known in the art. For example, where the target is a Gli transcription factor, the target activity may be measured by level of transcription (i.e of the Hh pathway genes Gli1 or Ptc1), level of the protein whose transcription is operably linked or activity of the protein whose transcription is operably linked. Alternatively, activity of a HPI of the disclosure may be measured by detection of a marker gene, for example, lacZ, one of the family of fluorescent polypeptides (e.g., GFP, YFP, BFP, RFP etc), or luciferase which is operably linked to Gli DNA binding sites.

Description

Inappropriate activation of the Hedgehog (Hh) signaling pathway has been implicated in a diverse spectrum of cancers, and its pharmacological blockade has emerged as an antitumor strategy. While nearly all known Hh pathway antagonists target the transmembrane protein Smoothened (Smo), small molecules that suppress downstream effectors could more comprehensively remediate Hh pathway-dependent tumors. The present disclosure provides antagonists that are epistatic to Smo, including two that can inhibit Hh target gene expression induced by the overexpression of Gli transcription factors. Their effects on Gli processing, stability, and trafficking highlight the role of primary cilia in Gli regulation, and provide evidence that Gli activator formation is a multi-step process. The ability of certain compounds to block the proliferation of medulloblastoma progenitor cells is shown and demonstrate that Hh pathway inhibitors can have tissue-specific activities.

Certain neoplasms require Hh ligand function, either through autocrine or paracrine signaling mechanisms, including small-cell lung cancers, pancreatic adenocarcinomas, and prostate tumors. In other cases, ligand-independent Hh target gene expression can lead to tumorigenesis, exemplified by Gorlin's syndrome patients who are heterozygous for Ptch1 and highly susceptible to basal cell carcinomas, medulloblastomas, and rhabdomyosarcomas. Oncogenic mutations in Smo have also been identified, and tumors can arise from loss of Su(fu).

A link between Hh target gene expression and oncogenesis indicates that pharmacological inhibitors of the Hh pathway may have therapeutic value. For example, the Smo antagonist cyclopamine can block tumor progression in a variety of mouse cancer models. While small molecules may be effective against Hh ligand-dependent tumors and those that involve a loss of Ptch1 function, cancers that result from downstream lesions within the Hh pathway are unlikely to be remediated; the oncogenic Smo mutant SmoM2 is resistant to cyclopamine, and medulloblastomas that arise in Su(fu) heterozygous mice are unresponsive to Smo inhibitors.

Screens of 1,990 synthetic chemicals and 94 natural products have identified a few compounds that can antagonize Hh target gene expression induced by Gli1 or Gli2 overexpression, including GANT-58, GANT-61, zerumbone, arcyriaflavin C, and physalin F. How these compounds antagonize Gli function has not been determined, although GANT-61 appears to attenuate the DNA-binding activity of Gli1 in vivo, and it has been suggested that arcyriaflavin C and physalin F indirectly antagonize Gli function through PKC/MAPK pathway blockade. Similarly, the natural product forskolin can inhibit Hh signaling by activating adenylate cyclase and consequently PKA, but its mechanism of action impacts multiple signaling pathways.

To discover nHh pathway inhibitors that do not directly target Smo, a large-scale, high-throughput screen was conducted for compounds that can abrogate Hh target gene expression induced by the Smo agonist SAG. The screening assays of the disclosure minimize the inhibitory activities of Smo-targeting compounds, since most known Smo antagonists are functionally and biochemically competitive with SAG. Four Hh pathway inhibitors (HPIs) that differentially perturb biochemical and cellular processes associated with Hh signaling, including several that involve the primary cilium. Their phenotypes revealed multiple pharmacologically targetable events within the Hh pathway, and a subset of these compounds can block the SmoM2-dependent proliferation of medulloblastoma progenitors.

Disruption of the Hh pathway may result in cellular proliferative disease characterized by the undesired propagation of cells, including, but not limited to, neoplastic disease conditions, e.g., cancer. Examples of cellular proliferative disease include, but are not limited to, skin cancer, (including Basal Cell carcinoma), brain cancer, (including glioma and medulloblastoma), colon cancer, mesothelioma, lung cancer, renal cell carcinoma, breast cancer, prostate cancer, sarcoma, ovarian cancer, esophageal cancer, stomach cancer, gastric cancer, hepatocellular cancer, rhabdomyosarcoma, nasopharyngeal cancer and pancreatic cancer. Subjects seeking alleviation according to the methods of the disclosure include any individual having any of the above-mentioned disorders.

In certain cases the disclosure provides compounds and methods of antagonizing, or inhibiting, the Hh pathway (i.e., an activated Hh pathway) by administering a HPI to a mammalian cell. Antagonism of the Hh pathway can be useful in the context of a tumor, for example, inhibition of cellular proliferation, inhibition of cellular transformation and inhibition of cellular migration (e.g., as an anti-cancer agent). In another aspect the disclosure provides compounds and methods of antagonizing the Hh pathway by administering a HPI to a mammalian cell useful in the context of developmental disorders, where in the developing cell or tissue, inhibition of the Hh pathway would be beneficial. The disclosure should not be construed to be limited solely to the treatment of patients having a cellular proliferative disease. Rather, the disclosure should be construed to include the alleviation of conditions or disease associated with increased expression of Hh pathway genes that would benefit from the compounds and methods of the subject disclosure.

The HPIs and methods of the instant disclosure can be used for prophylactic or therapeutic purposes. As used herein, the term "alleviate" or "alleviation" is used to refer to both prevention of disease, and reduction of pre-existing conditions. The reduction of ongoing disease (e.g. cancer), in order to stabilize or improve the clinical symptoms of the patient, is of particular interest. Such alleviation is desirably performed prior to loss of function in the affected tissues. Evidence of alleviation may be any diminution in the severity of disease, particularly measuring the severity of such symptoms as found in development and tumorigenic transformation of the skin, brain, lung, breast, prostate, gut, and blood.

Such subjects may be tested in order to assay the activity and efficacy of the subject HPIs. A significant improvement in one or more of parameters is indicative of efficacy. It is well within the skill of the ordinary healthcare worker (e.g., clinician) to adjust dosage regimen and dose amounts to provide for optimal benefit to the patient according to a variety of factors (e.g., patient-dependent factors such as the severity of the disease and the like, the compound administered, and the like).

Pharmaceutical Preparations Containing Compounds of the Disclosure.

Provided by the disclosure are pharmaceutical preparations of the subject HPIs described above. The subject HPIs can be incorporated into a variety of formulations for therapeutic administration by a variety of routes. More particularly, the HPIs of the present disclosure can be formulated into pharmaceutical compositions by combination with appropriate, pharmaceutically acceptable carriers, diluents, excipients and/or adjuvants, and may be formulated into preparations in solid, semi-solid, liquid or gaseous forms, such as tablets, capsules, powders, granules, ointments, solutions, suppositories, injections, inhalants and aerosols, in a sterile vial or in a syringe. Where the formulation is for transdermal administration, the compounds are preferably formulated either without detectable DMSO or with a carrier in addition to DMSO. The formulations may be designed for administration to subjects or patients in need thereof via a number of different routes, including oral, buccal, rectal, parenteral, intraperitoneal, intradermal, intratracheal, etc. The administration can be systemic or localized delivery of the formulation to a site in need of treatment, e.g., localized delivery to a tumor or application directly to the skin.

Pharmaceutically acceptable excipients usable with the disclosure, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins. The HPI or HPI formulation to be administered will, in any event, contain a quantity of the agent adequate to achieve the desired state in the subject being treated.

In pharmaceutical dosage forms, the subject HPIs of the disclosure may be administered in the form of their pharmaceutically acceptable salts, or they may also be used alone or in appropriate association, as well as in combination, with other pharmaceutically active compounds. The following methods and excipients are merely exemplary and are in no way limiting.

Prodrugs of the HPIs of the disclosure may be provided by altering functional groups on the HPI in such a manner that the alterations are removed in the body of a mammal. In certain cases, the alterations/modifications are made during or after synthesis of the effective HPI. Actual methods of preparing prodrugs are known, or will be apparent to the skilled artisan. See Bundgaard, in Design of Prodrugs, ed. H. Bundgaard, Elsevier Science Publishers, New York (1985).

The HPI can be administered to a host using any available conventional methods and routes suitable for delivery of conventional drugs, including systemic or localized routes. In general, routes of administration contemplated by the disclosure include, but are not necessarily limited to, enteral, parenteral, or inhalational routes, such as intrapulmonary or intranasal delivery.

Conventional and pharmaceutically acceptable routes of administration include intranasal, intrapulmonary, intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

For oral preparations, the subject HPIs of the disclosure can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Parenteral routes of administration include, but are not necessarily limited to; inhalation administration, topical, transdermal, subcutaneous, intramuscular, intraorbital, intracapsular, intraspinal, intrasternal, intravenous routes, i.e., any route of administration other than through the alimentary canal, and local injection, with intra or peritumoral injection being of interest, especially where a tumor is a solid or semi-solid tumor (e.g., Hodgkins lymphoma, non-Hodgkins lymphoma, and the like). Local injection into a tissue defining a biological compartment ((e.g., prostate, ovary, regions of the heart (e.g., pericardial space defined by the pericardial sac), intrathecal space, synovial space, and the like)) is also of interest. Parenteral administration can be carried to effect systemic or local delivery of the agent. Where systemic delivery is desired, administration typically involves invasive or systemically absorbed topical or mucosal administration of pharmaceutical preparations.

Methods of administration of the HPI through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

The subject HPIs of the disclosure can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol, collagen, cholesterol; and if desired, with conventional additives such as solubilizers, isotonic agents, suspending agents, emulsifying agents, stabilizers and preservatives.

The HPIs of the disclosure can also be delivered to the subject by enteral administration. Enteral routes of administration include, but are not necessarily limited to, oral and rectal (e.g., using a suppository) delivery.

Furthermore, the subject HPIs can be made into suppositories by mixing with a variety of bases such as emulsifying bases or water-soluble bases. The compounds of the present disclosure can be administered rectally via a suppository. The suppository can include vehicles such as cocoa butter, carbowaxes and polyethylene glycols, which melt at body temperature, yet are solidified at room temperature.

Dosages of the Compounds of the Disclosure

Depending on the subject and condition being treated and on the administration route, the subject HPIs may be administered in dosages of, for example, 0.1 µg to 100 mg/kg body weight per day. In certain embodiments, the therapeutic administration is repeated until a desired effect is achieved. Similarly the mode of administration can have a large effect on dosage. Thus, for example, oral dosages may be about ten times the injection dose. Higher doses may be used for localized routes of delivery.

A typical dosage may be a solution suitable for intravenous administration; a tablet taken from two to six times daily, or one time release capsule or tablet taken once a day and containing a proportionally higher content of active ingredient, etc. The time release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Dosages for a given HPI are readily determinable by those of skill in the art by a variety of means.

Although the dosage used will vary depending on the clinical goals to be achieved, a suitable dosage range is one which provides up to about 1 µg to about 1,000 µg or about 10,000 µg of subject HPI to alleviate a symptom in a subject animal.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more HPIs of the disclosure.

Similarly, unit dosage forms for injection or intravenous administration may comprise the HPI(s) in a composition as a solution in sterile water, normal saline or another pharmaceutically acceptable carrier.

Combination Therapy Using the Compounds of the Disclosure

For use in the subject methods, the subject HPIs may be formulated with or otherwise administered in combination with other pharmaceutically active agents, including other agents that activate or suppress a biochemical activity, such as a chemotherapeutic agent. The subject compounds may be used to provide an increase in the effectiveness of another chemical, such as a pharmaceutical, or a decrease in the amount of another chemical, such as a pharmaceutical that is necessary to produce the desired biological effect.

Examples of chemotherapeutic agents for use in combination therapy include, but are not limited to, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES).

In certain cases, the HPIs of the current disclosure may also be used with an anti-angiogenic factor, for example, the anti-VEGF antibody AVASTIN™.

Furthermore, the HPIs of the present disclosure may also be used in combination therapy with other Hh pathway antagonists, including another HPI of the disclosure. Examples of agents for use in combination therapy include, but are not limited to; cyclopamine, SANT 1-4, antibodies to Shh, Ihh, Dhh, Ptc1, Ptc2 or Smo. For example, the HPIs of the disclosure may be administered to antagonize a Gli gene or polypeptide, and the second Hh pathway antagonist may be administered to reduce Smo signaling. In an additional example, a HPI of the disclosure may be administered in combination with a second HPI of the disclosure.

The HPIs described herein for use in combination therapy other therapeutics may be administered by the same route of administration (e.g. intrapulmonary, oral, enteral, etc.) that the HPIs of the disclosure are administered. In the alternative, the therapeutics for use in combination therapy with the HPIs of the present disclosure may be administered by a different route of administration that the HPIs of the disclosure are administered.

Kits

Kits with unit doses of the subject compounds, usually in oral or injectable doses, are provided by the present disclosure. In such kits, in addition to the containers containing the unit doses will be an informational package insert describing the use and attendant benefits of the drugs in treating pathological condition of interest. Representative compounds and unit doses are those described herein above.

In one embodiment, the kit comprises a HPI formulation in a sterile vial or in a syringe, which formulation can be suitable for injection in a mammal, particularly a human.

One aspect of the present disclosure provides compounds according to formula (I):

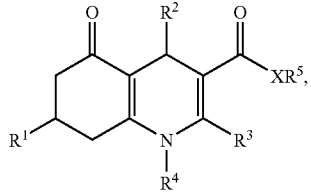

wherein: $R^1$, $R^2$, $R^3$, and $R^5$ can be independently: H, $CO_2R$, $NO_2$, CN, $SO_2$, SH, SR, OH, OR, $NH_2$, NHR, NRR, an ether group, alky, alkenyl, alkynyl, alkoxy, cycloalkyl, aryl, heterocycloalkyl, or heteroaryl, wherein alkyl, alkenyl, alkynyl, alkoxy, cycloalkyl, heterocycloalkyl, and heteroaryl may be optionally substituted with: $CO_2R$, $NO_2$, CN, $SO_2$, SH, SR, OH, OR, $NH_2$, NHR, NRR, halogen, alkyl, alkenyl, alkynyl, alkoxy, cycloalkyl, aryl, heterocycloalkyl, or heteroaryl; $R^4$ can be: H, $CO_2R$, or alkyl, where alkyl may be optionally substituted with $CO_2R$, $NO_2$, CN, $SO_2$, SH, SR, OH, OR, $NH_2$, NHR, NRR, halogen, alkyl, alkenyl, alkynyl, alkoxy, cycloalkyl, aryl, heterocycloalkyl, or heteroaryl; R can be independently: H; alkyl, cycloalkyl, aryl, heterocycloalkyl, or heteroaryl; and X can be: O, N, or S; or a pharmaceutically acceptable salt thereof.

Figure 20A:
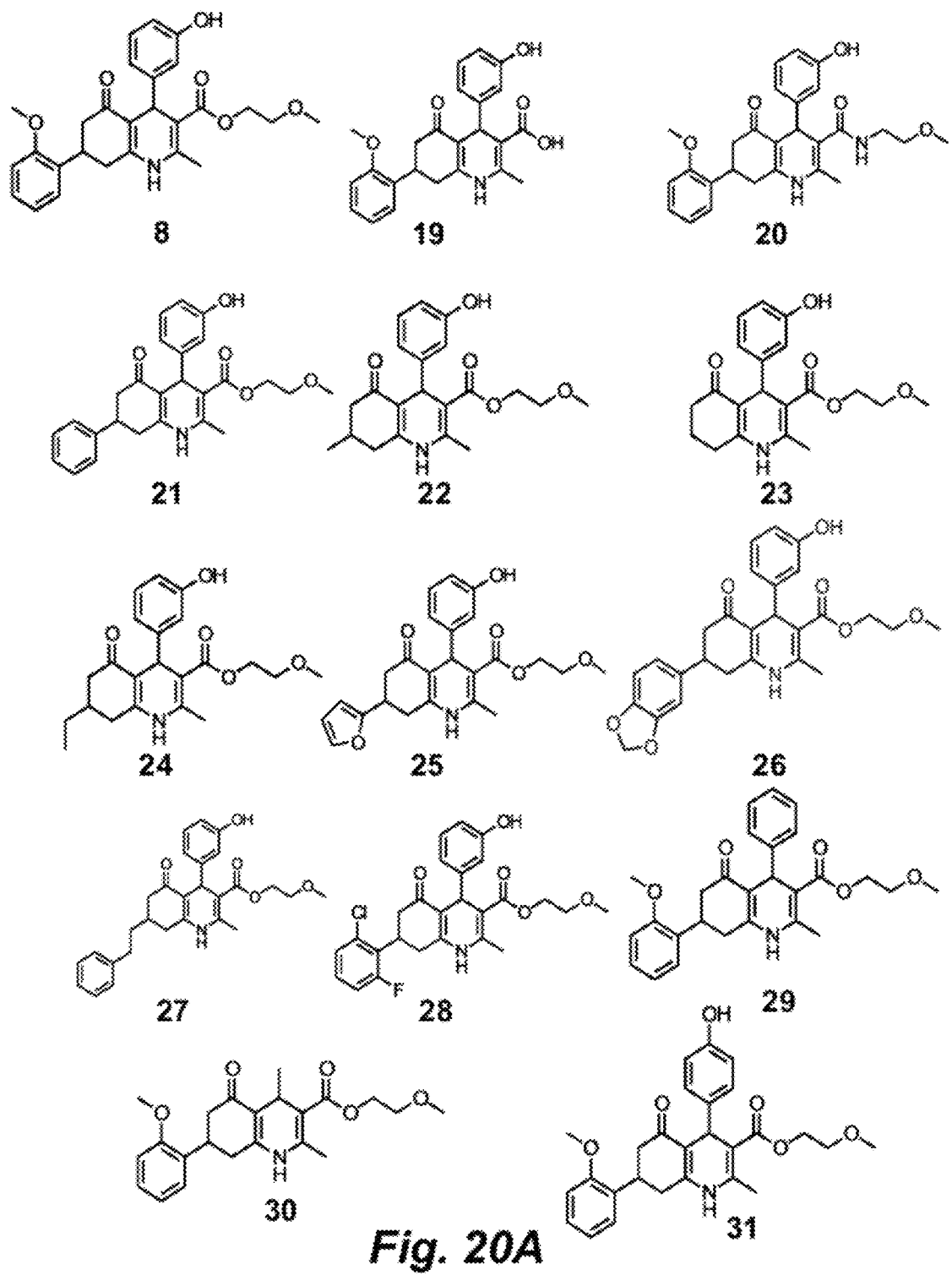
FIGS. 20A and 20B illustrate the HPI-1 and derivatives thereof as presented in Table 2.
Figure 20B:
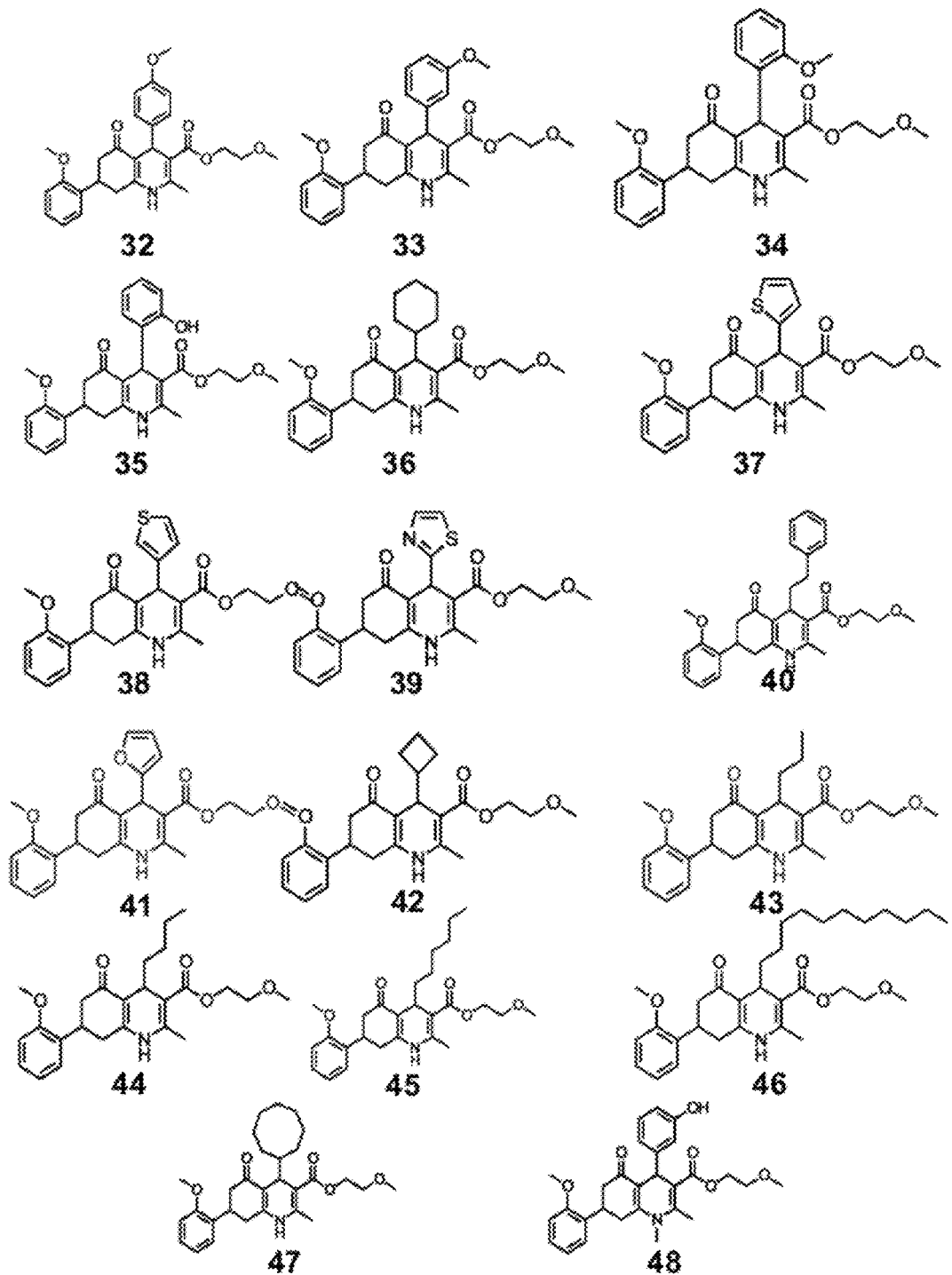

In the embodiments of this aspect of the disclosure, the compounds are antagonists of the Hedgehog signaling pathway of a cell. In the embodiments of the present disclosure, the compound can be selected from the group consisting of the compounds as shown in FIGS. 20A and 20B, or a pharmaceutically acceptable salt thereof.

In one embodiment of the disclosure, in the compound $R^1$ is aryl, optionally substituted with OH, alkoxy, or halogen; alkyl optionally substituted with aryl; heterocycloalkyl; or heteroaryl; $R^2$ is aryl, optionally substituted with OH or alkoxy; cycloalkyl; alkyl optionally substituted with aryl; or heteroaryl; $R^3$ is H or alkyl; $R^4$ is H or alkyl; $R^5$ is an ether group; and X is N or O; or pharmaceutically acceptable salt thereof.

Figure 19:
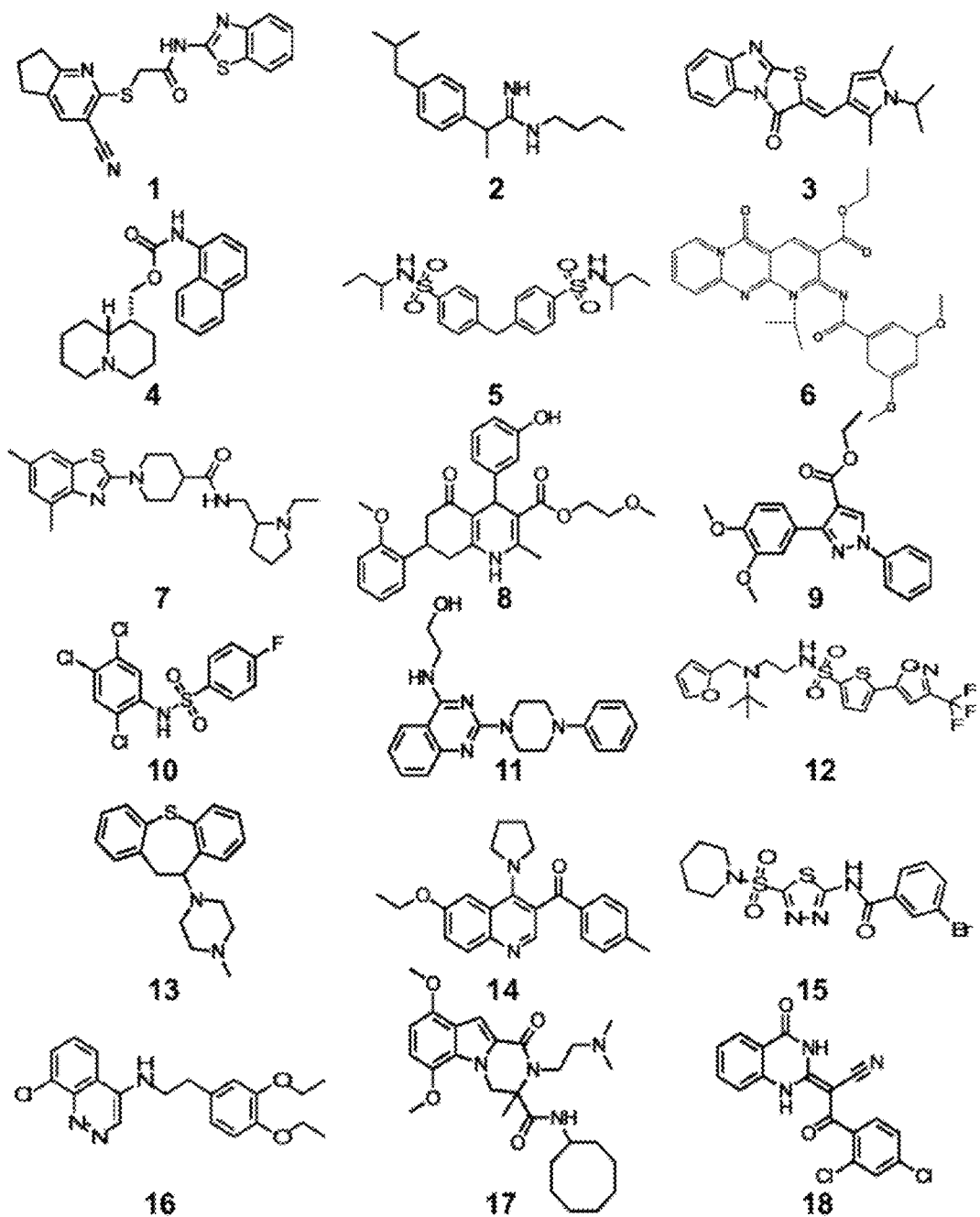
FIG. 19 illustrates the compounds of the disclosure as presented in Table 1.

Another aspect of the disclosure provides compounds selected from the group consisting of: the compounds as shown in FIG. 19, or a pharmaceutically acceptable salt thereof.

In the embodiments of this aspect of the disclosure, the compounds are antagonists of the Hedgehog signaling pathway of a cell.

Another aspect of the disclosure provides for pharmaceutical compositions comprising a compound or pharmaceutically acceptable salt thereof according to any one of the above embodiments, and a pharmaceutically acceptable carrier.

Still another aspect of the disclosure is a method of inhibiting Hedgehog pathway signaling in a cell, the method comprising: contacting the cell with a compound as set forth in any one of claims 1-4 in an amount effective to inhibit Hedgehog signaling in the cell; wherein Hedgehog pathway signaling in the cell is inhibited.

In embodiments of this aspect of the disclosure, the Hedgehog signaling is associated with undesirable cell proliferation.

In other embodiments of the disclosure, the cell may be a tumor cell.

In still other embodiments, the inhibition of the hedgehog pathway signaling in the cell may induce apoptosis of the cell.

In one embodiment of the disclosure, the cell is a cultured cell. In other embodiments, the cell is present in a mammal.

In the embodiments of the disclosure, the compound can be in a pharmaceutically acceptable composition.

In these embodiments of the disclosure, the pharmaceutically acceptable composition may further comprise a pharmaceutically acceptable carrier.

In yet other embodiments of the methods of this aspect of the disclosure, the methods may further comprising administering to the mammal an effective amount of a second therapeutic agent.

Still another aspect of the disclosure provides methods of screening a candidate agent for use as a Hedgehog pathway inhibitor compound (HPI), the method comprising: contacting a cell with a Smo agonist, wherein the cell comprises a heterologous reporter gene construct comprising Gli DNA binding sites operably linked to a region encoding a reporter; contacting the cell with a candidate HPI agent; and detecting a difference in activity of the reporter, wherein a lower level of activity of the reporter marker as compared to a control cell untreated with the candidate HPI is indicative of HPI activity.

In embodiments of this aspect of the disclosure, the Smo agonist is selected from the group consisting of: SAG, cyclopamine, SANT-1, SANT-2, SANT-3, SANT-4, and Purmorphamine.

In these embodiments, the reporter marker is luciferase, lacZ, alkaline phosphatase or a fluorescent protein.

Another aspect of the disclosure provides methods of diagnosing cancer in a mammal, the method comprising: contacting a detectably labeled HPI with a test sample of cancer cells suspected of over-expressing a Gli transcription factor; detecting the level of a Gli transcription factor in the test sample of cancer cells obtained from the mammal, wherein a higher level of HPI label detected as compared to a control sample is indicative of cancer in the mammal from which the test sample of cancer cells were obtained.

Yet another aspect of the disclosure provides kits comprising a container and a doses or plurality of doses of a Hedgehog pathway antagonist compound according to any of claims 1-4, and a package insert describing the use and attendant benefits of said compound, or a pharmaceutical composition comprising said compound, in treating a pathological condition of interest.

In embodiments of this aspect of the disclosure, the kit comprises said compound, or a pharmaceutical formulation comprising said compound, in a sterile vial or in a syringe, and wherein said formulation is suitable for injection in a recipient subject.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Identification of Hh pathway inhibitors (HPIs) that do not directly target Smo. To facilitate the identification of antagonists that act downstream of Smo, screening conditions were established that exploited competitive interactions between Smo agonists and antagonists. Shh-LIGHT2 cells, an NIH-3T3-derived cell line stably transfected with Gli-dependent firefly luciferase and constitutive Renilla luciferase reporters were stimulated with 0.5 µM SAG. 122,755 compounds were surveyed for the ability to block the resulting firefly luciferase expression without affecting Renilla luciferase activity. These assay conditions were resistant to inhibition by cyclopamine and similarly acting Smo inhibitors, whereas forskolin was equipotent against Shh and SAG-dependent Hh pathway activation as shown in FIG. 1A.

Figure 1B:
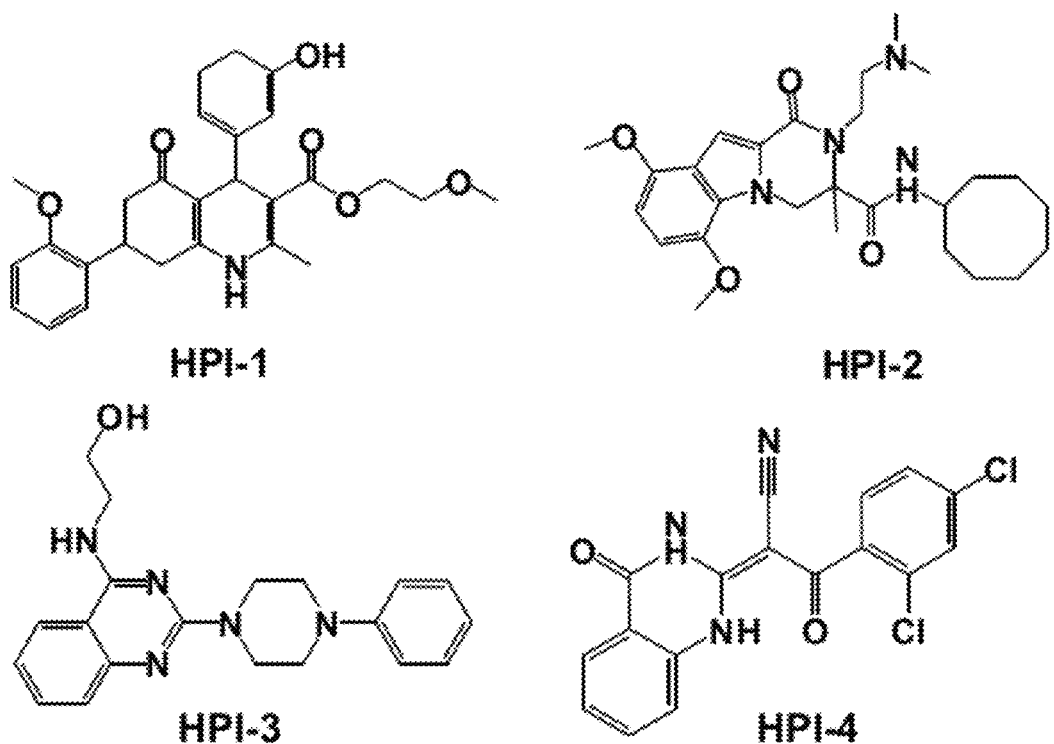
Figure 1C:
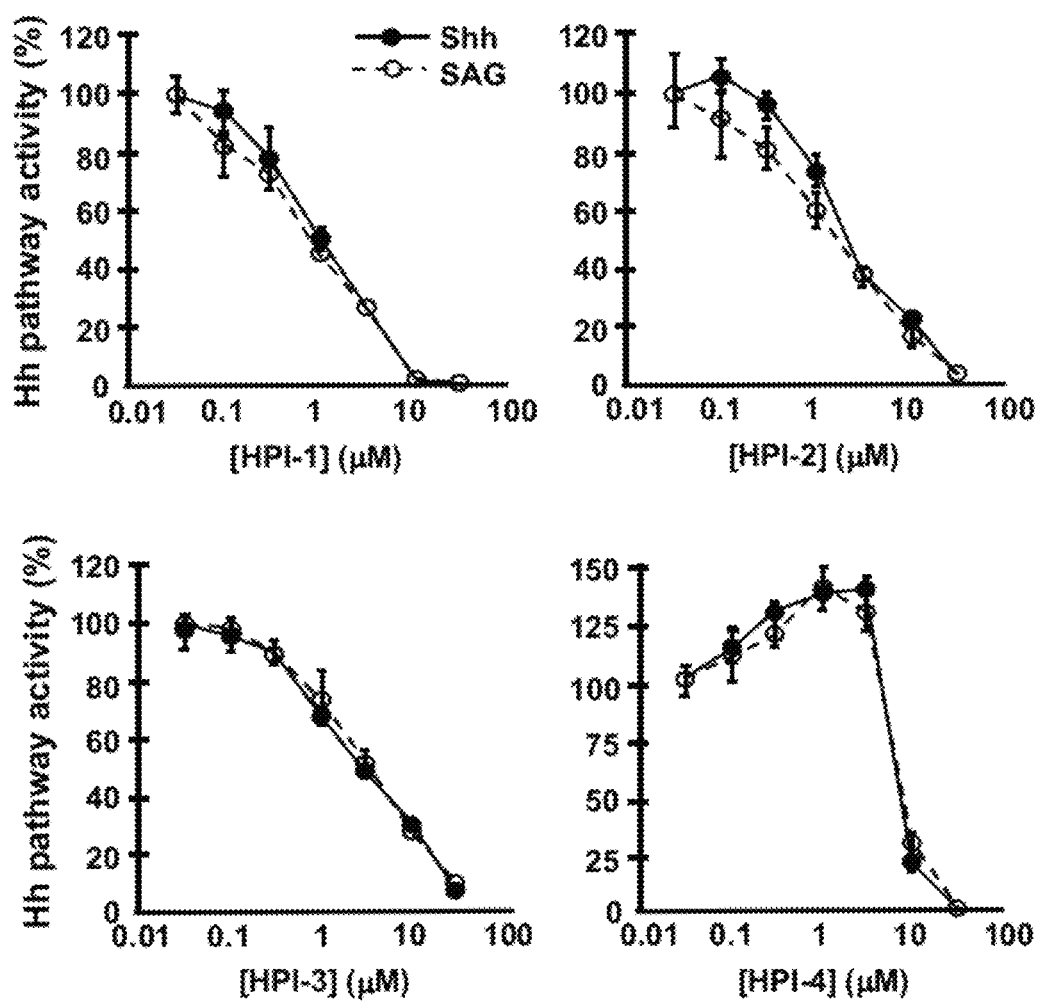
Figures 1D, 1E, 1F, 1G, 1H, 1I:
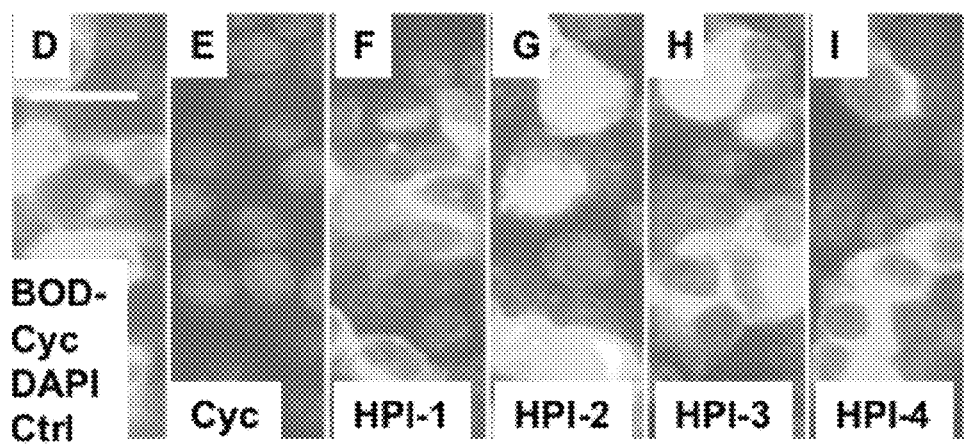

Through this screen (FIG. 1B), Hh pathway inhibitors such as HPI-1-HPI-4, as shown in FIG. 19, and Table 1) with median inhibitory concentrations (IC50s) less than 10 µM, and mechanisms of action that are distinct from cyclopamine, were identified. Inhibitors did not exhibit differential inhibition of Shh- and SAG-induced firefly luciferase expression in Shh-LIGHT2 cells (FIG. 1C), as is observed with cyclopamine and other Smo antagonists such as the SANTs. Nor did the compounds attenuate the binding of a fluorescent cyclopamine derivative (BODIPY-cyclopamine) to Smo-overexpressing HEK-293T cells (FIGS. 1D-1I).

Figure 6:
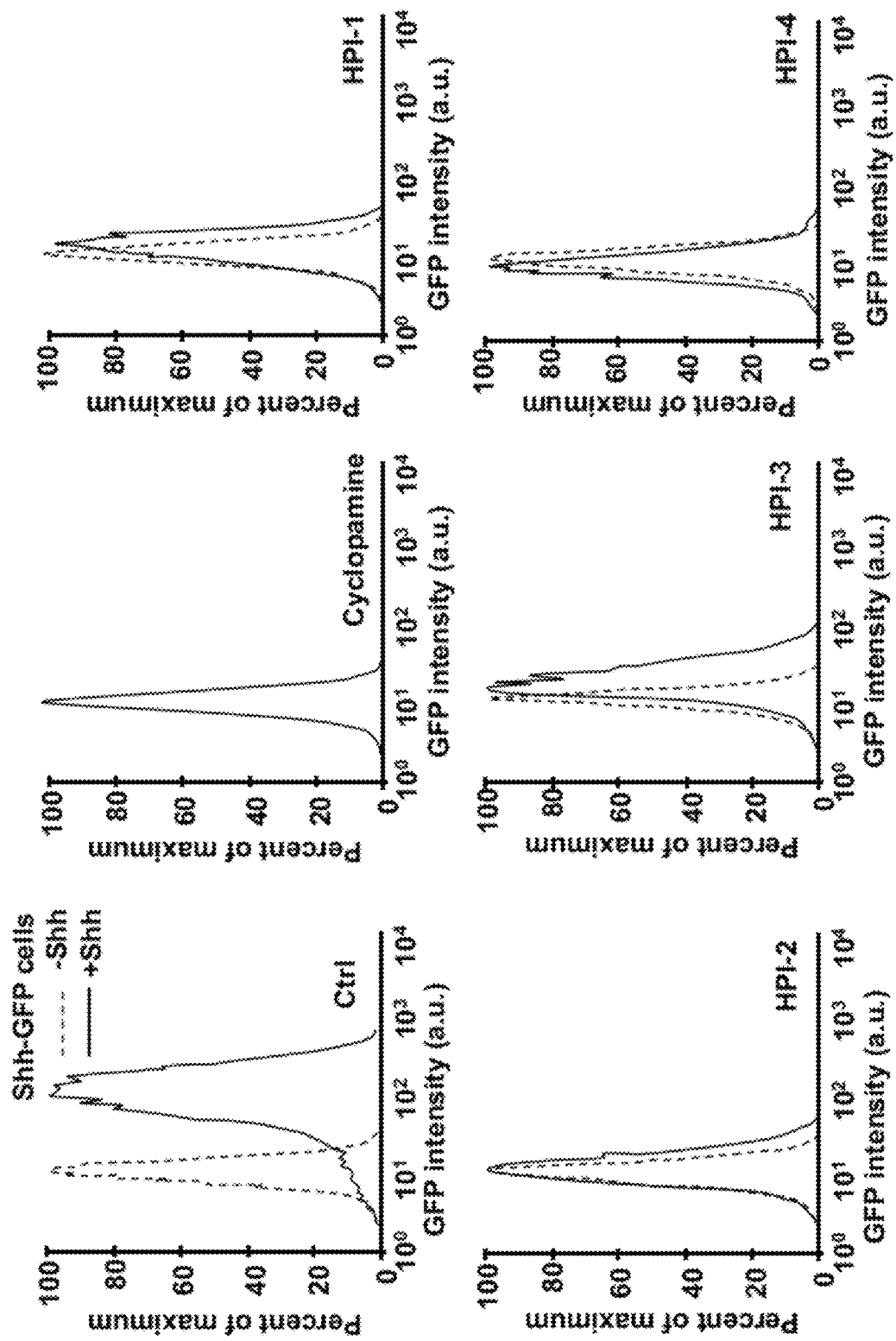
FIG. 6 illustrates as series of graphs showing the inhibition of Hh pathway activity in Shh-EGFP cells by the HPIs. Hh pathway activity in Shh-EGFP cells can be monitored by FACS, as demonstrated by the difference in fluorescence intensity observed between untreated cells (dark) and those stimulated with Shh-conditioned medium (light). Shh-EGFP cells treated simultaneously with Shh and either 3 µM cyclopamine or individual HPIs exhibit fluorescence intensities similar to those of untreated cells. The HPIs were used at concentrations ten-fold greater than their IC50s in the Shh-LIGHT2 assay or 30 µM, whichever was lower (15 µM HPI-1, 20 µM HPI-2, 30 µM HPI-3, and 30 µM HPI-4).
Figure 7:
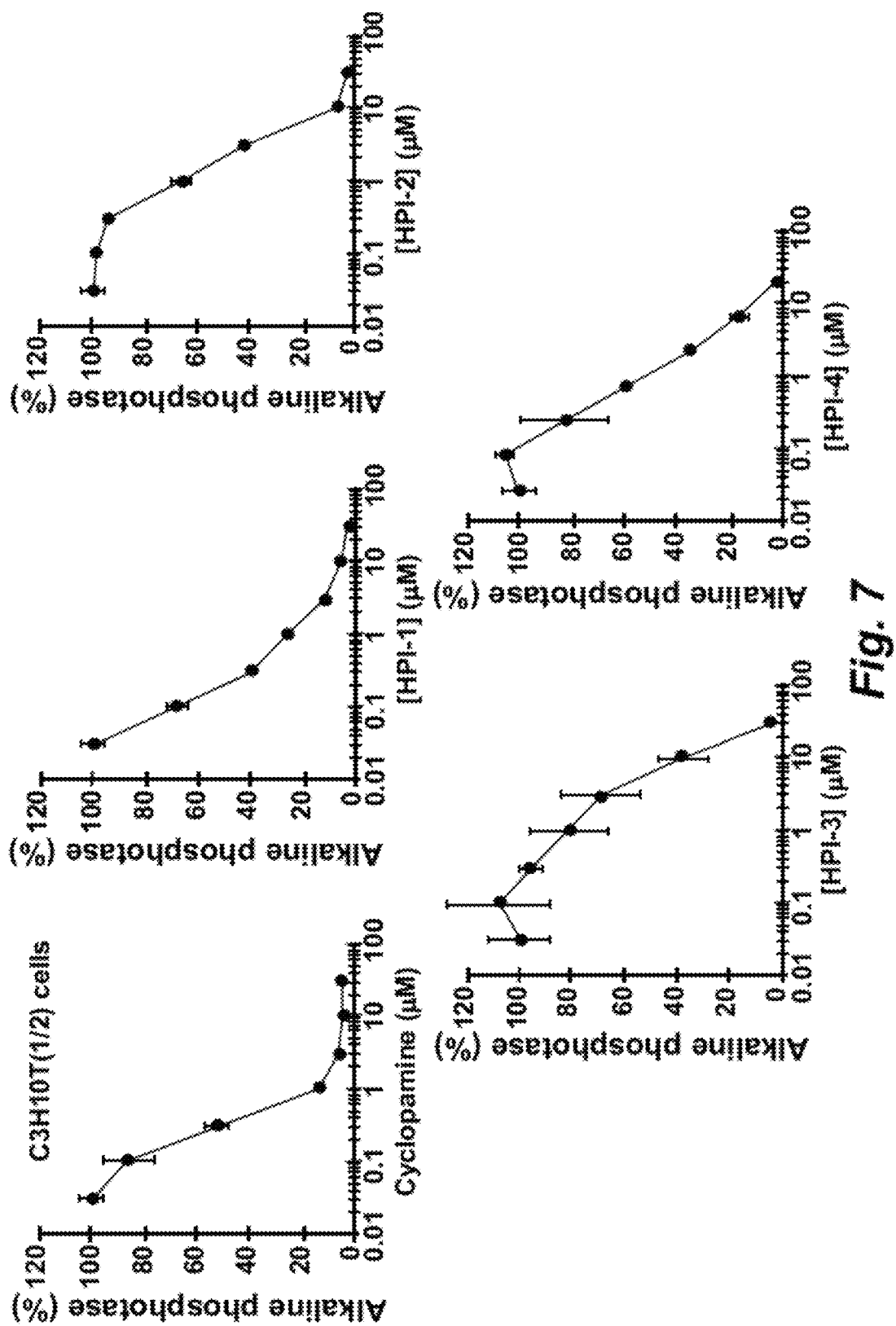
FIG. 7 illustrates a series of graphs showing the inhibition of Shh-dependent osteogenesis by the HPIs. Cyclopamine and the individual HPIs block the Shh-induced differentiation of C3H10T(1/2) cells into alkaline phosphatase-expressing osteoblasts. Data are the average of triplicate samples ± s.d.
Figure 8:
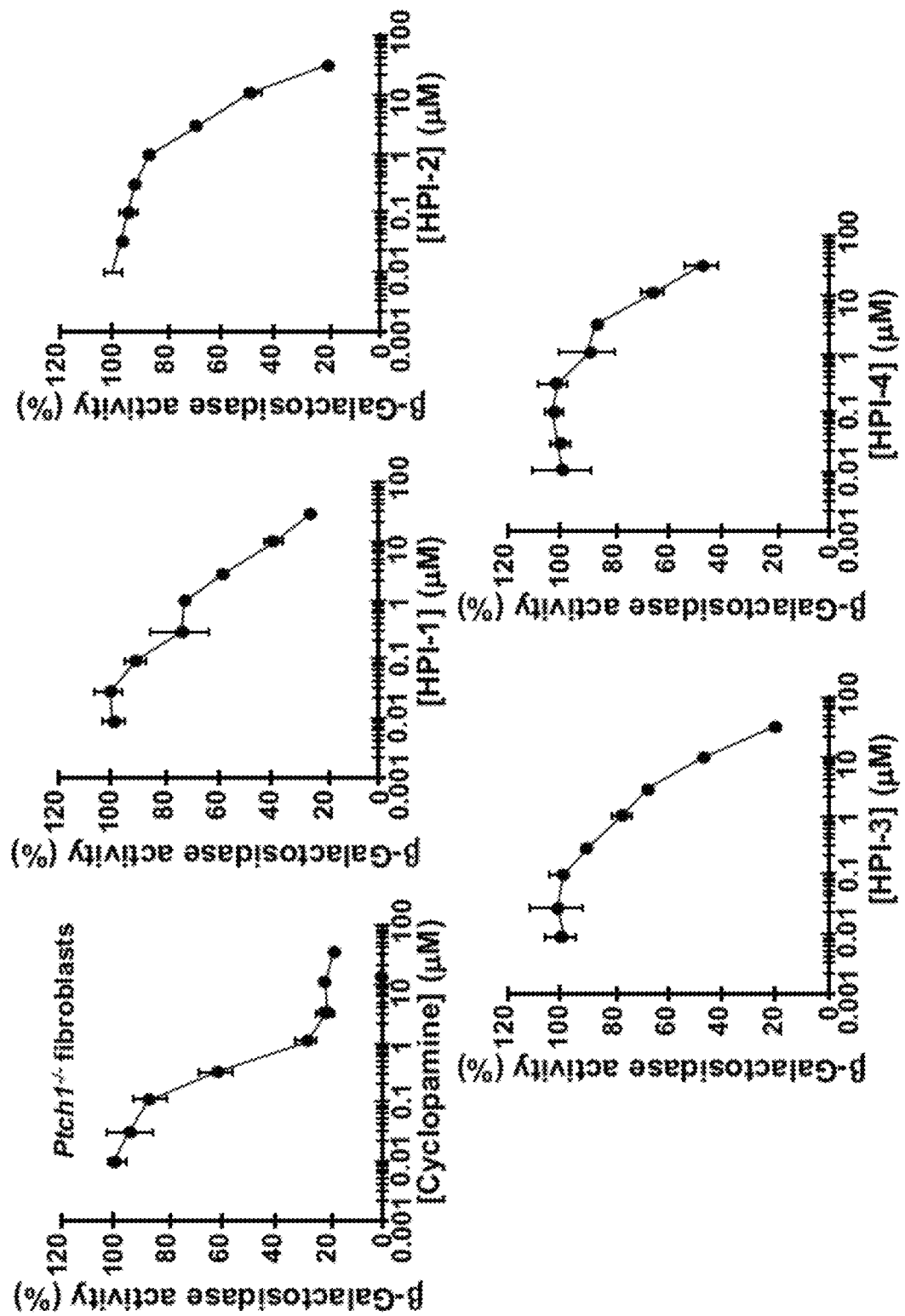
FIG. 8 illustrates a series of graphs showing the inhibition of constitutive Hh pathway activity in Ptch1$^{-/-}$ fibroblasts by the HPIs. Cyclopamine and the individual HPIs inhibit Hh pathway activity in Ptch1$^{-/-}$ fibroblasts as determined by cellular levels of the β-galactosidase reporter knocked into the Ptch1 coding region. Data are the average of triplicate samples ± s.d.
Figure 9:
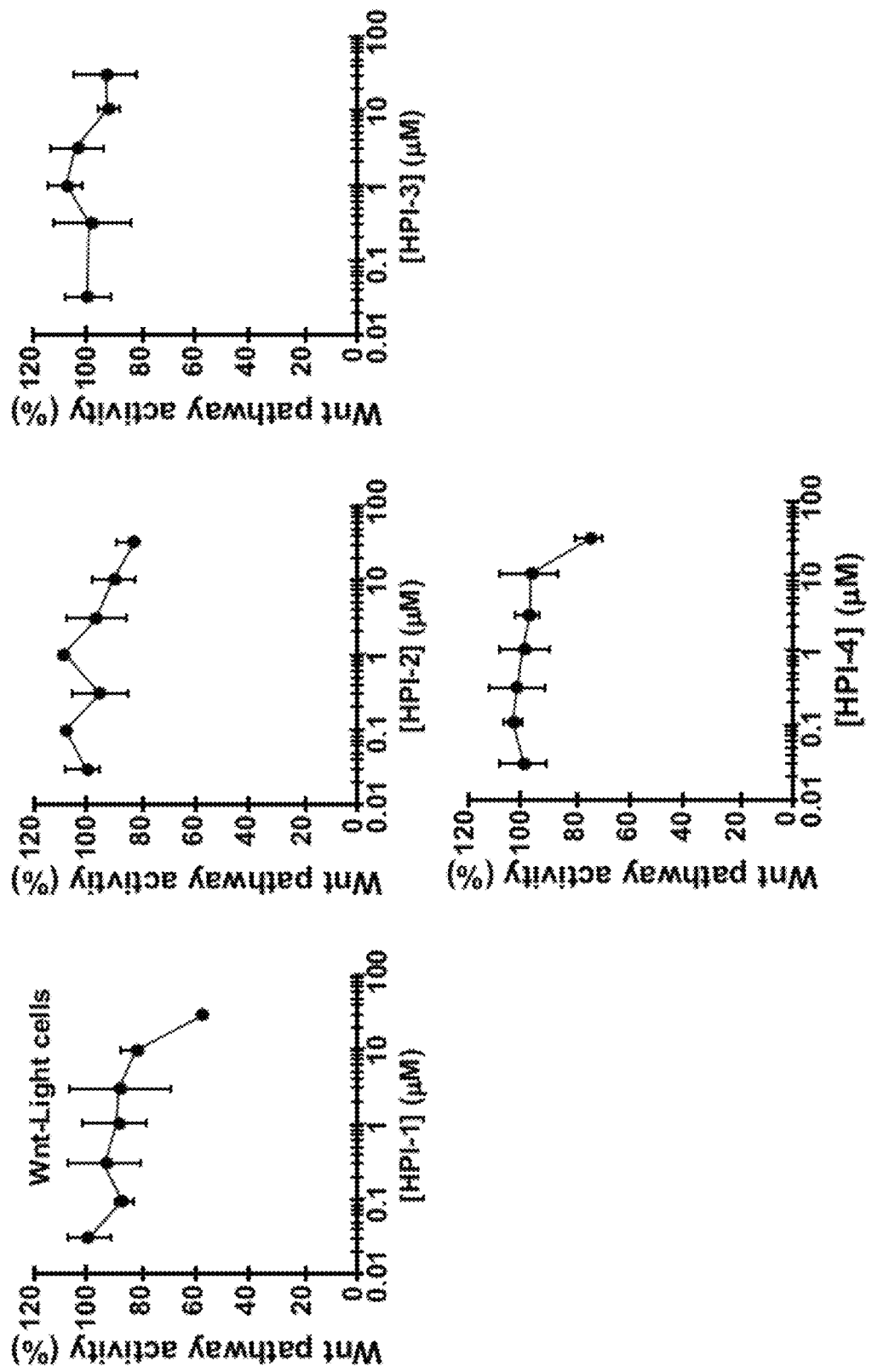
FIG. 9 illustrates a series of graphs showing the effects of the HPIs on Wnt-LIGHT cells. None of the HPIs significantly inhibit Wnt3a-induced pathway activation in L cells, as measured by a stably transfected TCF/LEFdependent firefly luciferase reporter. Data are the average of triplicate samples ± s.d.

The compounds HPI-1-HPI4 were tested in other cell lines competent for Hh target gene expression. A stable NIH-3T3 cell line was generated with a Gli-dependent enhanced green fluorescent protein reporter to provide a non-luciferase-based assay for compound activity (Shh-EGFP cells; FIG. 6). The ability of these small molecules to block Shh-induced differentiation of C3H10T(1/2) cells into alkaline phosphatase-positive osteoblasts (FIG. 7) or the constitutive Hh target gene expression in embryonic fibroblasts derived from Ptch1$^{-/-}$ mice were also evaluated as assessed by the β-galactosidase reporter replacing the Ptch1 coding region (FIG. 8). The compounds exhibited inhibitory activities in all three of these contexts, although some variability with respect to specific $IC_{50}$s was observed. In contrast, none of the compounds were able to block Wnt signaling in L cells stably transfected with a TCF/LEF-dependent firefly luciferase and treated with Wnt3a-conditioned medium (FIG. 9).

Example 2

HPI modulation of Smo multimerization and trafficking. The activities of these compounds against Hh target gene expression induced by loss of Ptch1 function or by SAG treatment indicate that they perturb Smo function and/or act downstream of this transmembrane receptor. Their inability to block BODIPYcyclopamine/Smo binding and their non-competitive interactions with respect to SAG further suggested that the four inhibitors do not directly target Smo. To evaluate whether any of the compounds perturb Smo multimerization or trafficking. Smo aggregation state can be monitored by co-expressing cyan and yellow fluorescent protein-tagged forms of this receptor (Smo-CFP and Smo-YFP) in NIH-3T3 cells, and observing fluorescence resonance energy transfer (FRET) between the two chromophores 9.

Figures 1J, 1K:
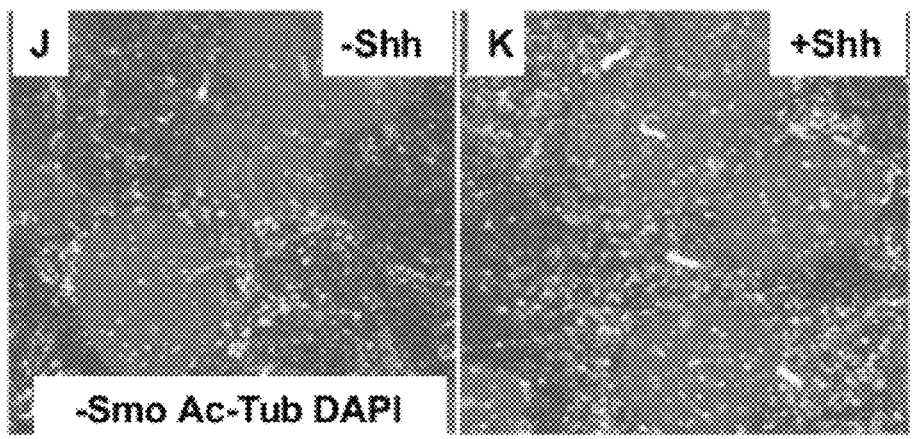
Figure 1L:
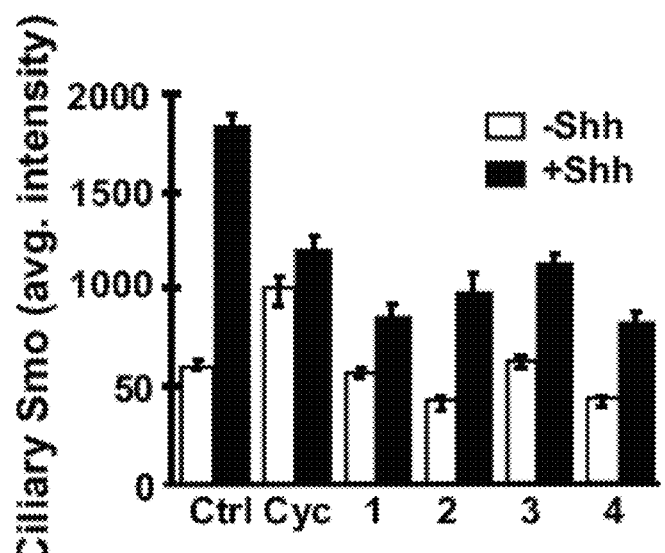
Figures 10A, 10B, 10C, 10D, 10E, 10F, 10G, 10H:
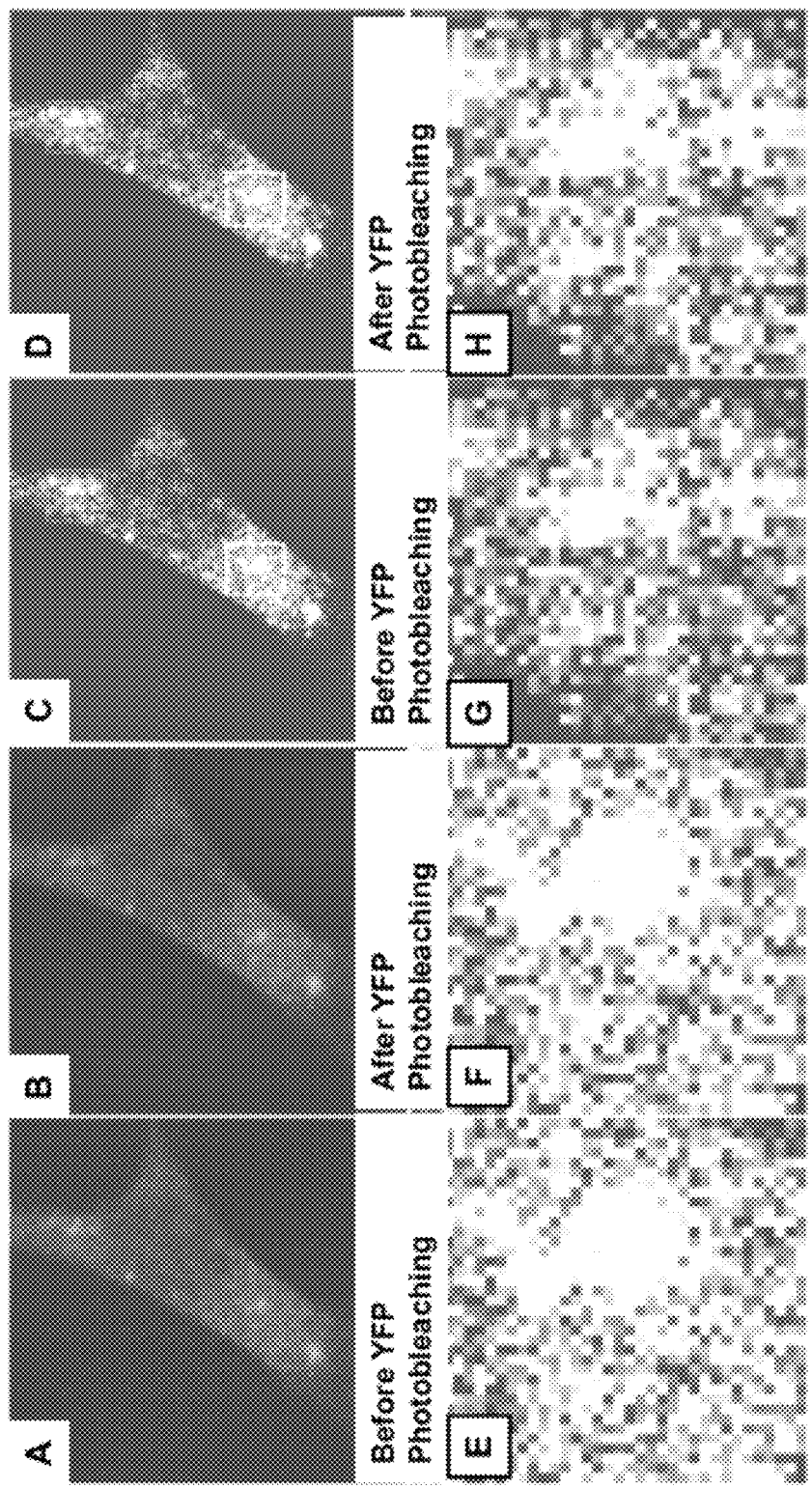
FIGS. 10A-10J illustrates the modulation of basal and Shh-induced Smo-CFP/Smo-YFP FRET by the HPIs.
Figure 10J:
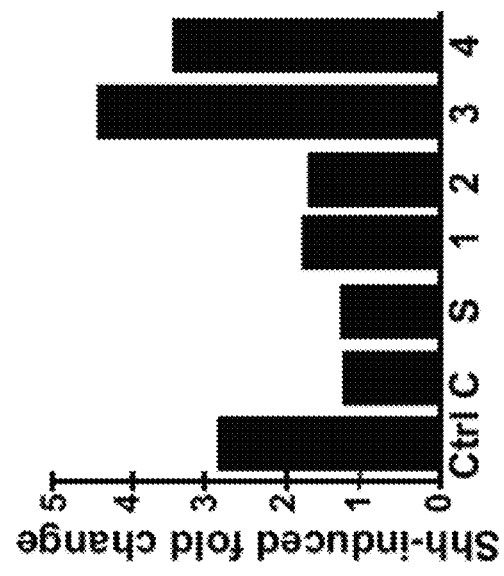
Figure 10I:
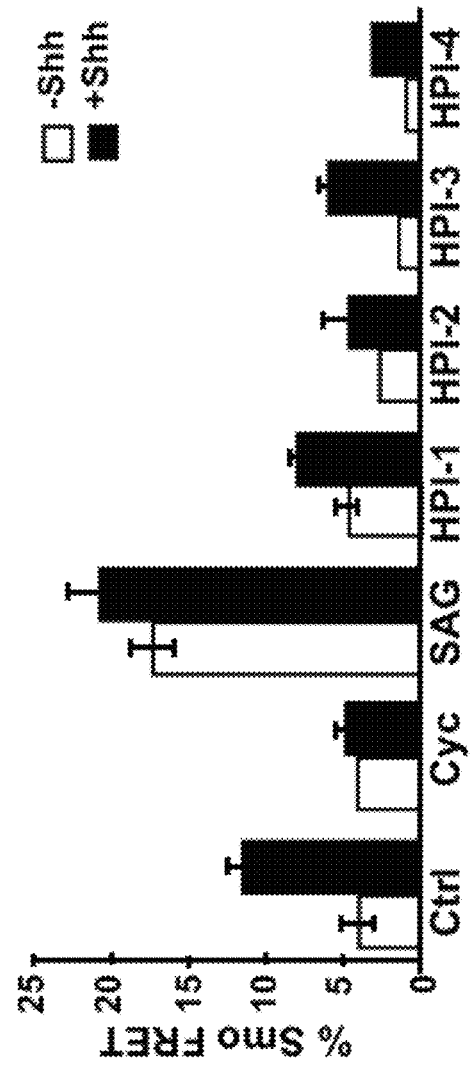

Treatment of these cells with Shh causes an increase in FRET, which can be blocked by the Smo antagonist cyclopamine (FIG. 10). Smo-CFP/Smo-YFP FRET is also Shh-insensitive in cells treated with SAG, since the compound alone can fully activate Smo. Using this assay, we observed that HPI-1 and HPI-2 attenuated the fold-change in Smo-CFP/Smo-YFP FRET upon Shh stimulation, while HPI-2, HPI-3, and HPI-4 decreased basal FRET levels (FIG. 10). To ascertain the effects of the four compounds on endogenous Smo, we next analyzed the Shh dependent trafficking of Smo to the primary cilium using an antibody against the C-terminal cytoplasmic domain of murine Smo (FIG. 1J-1L). Smo antagonists are known to perturb this process; certain SANTs prevent ciliary accumulation of Smo in Shh-treated cells, and cyclopamine stabilizes an inactive form of ciliary Smo. We therefore cultured NIH-3T3 cells until they formed primary cilia, treated them with Shh ligand, and then monitored Smo localization by immunofluoresence. While none of the HPIs completely blocked Smo trafficking to the cilium, the extent of ciliary Smo accumulation in response to Shh stimulation was decreased by all four compounds. These observations indicate that the HPIs can partially perturb Smo aggregation state and trafficking, likely through an indirect mechanism of action.

Example 3

Figure 2A:
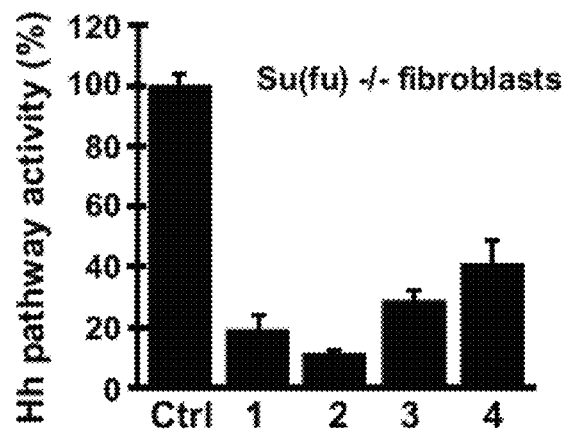
FIGS. 2A and 2B are graphs illustrating epistatic mapping of HPI activity relative to Su(fu), Gli1, and Gli2.
Figure 2B:
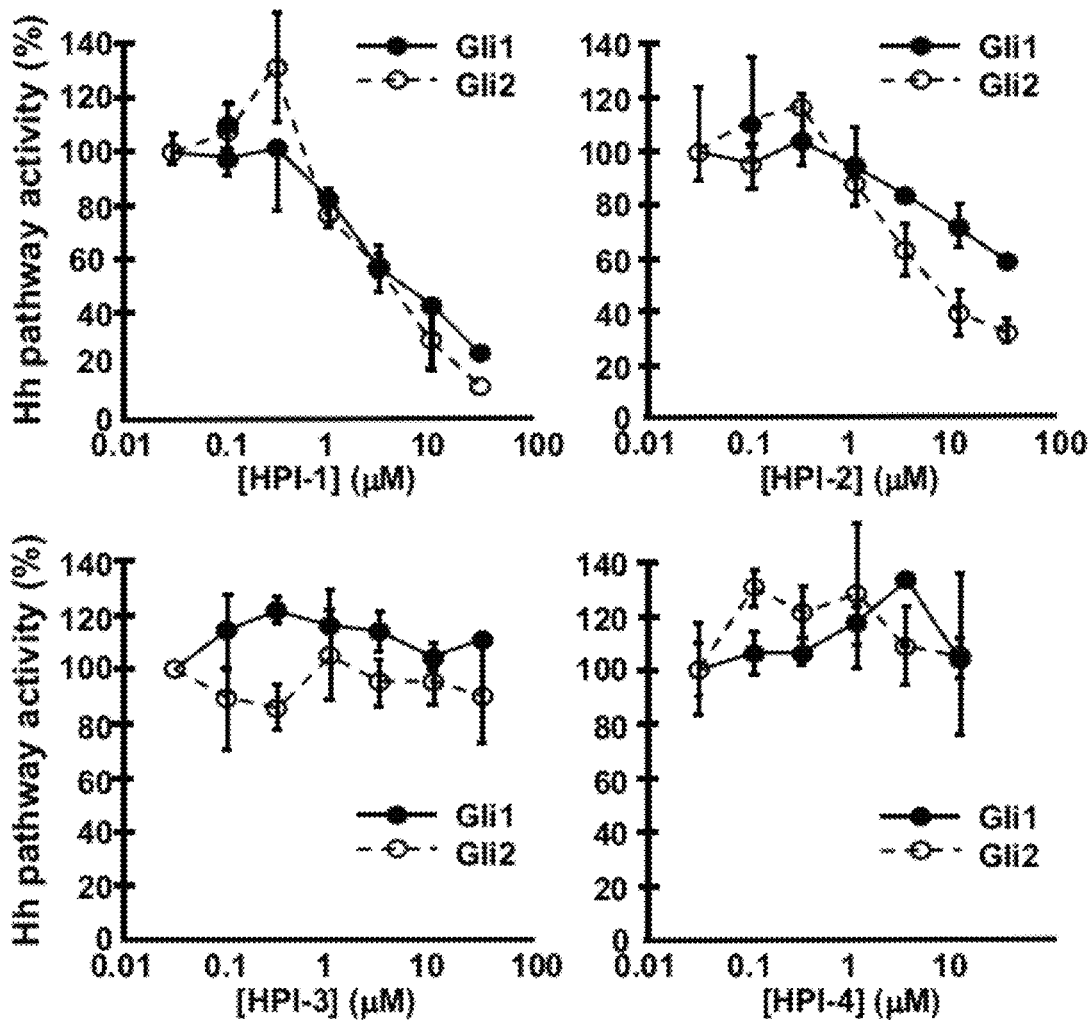
Figure 11:
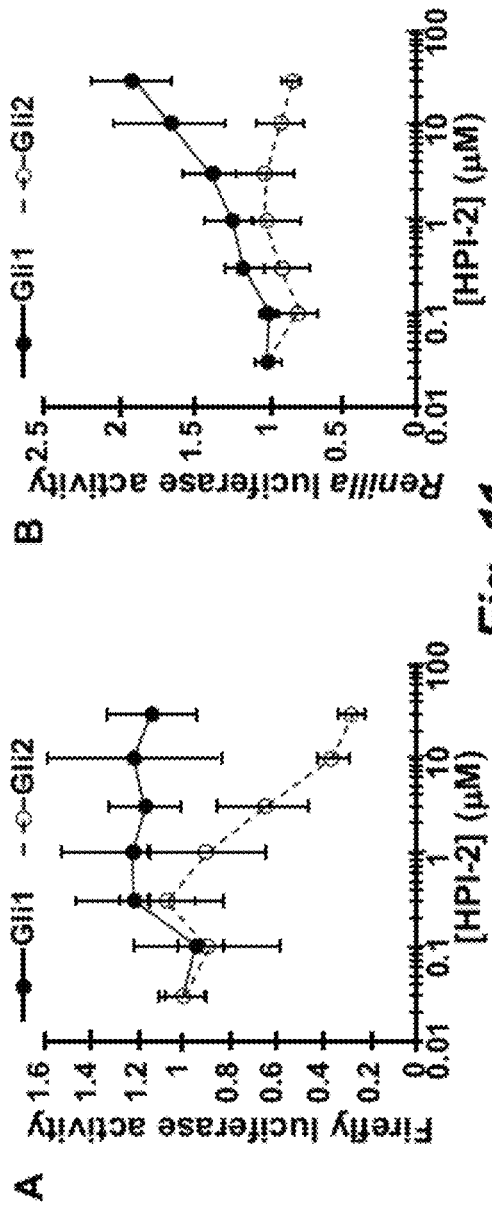
FIGS. 11A and 11B are graphs illustrating that HPI-2 selectively inhibits Gli2.

HPI epistasis with cytoplasmic Hh signaling proteins. To determine whether these partial effects on Smo multimerization and trafficking account for the inhibitory activities of the HPIs, we next investigated epistatic interactions between the antagonists and Hh signaling proteins downstream of Smo. For example, Su(fu)$^{-/-}$ fibroblasts exhibit constitutive, Smo-independent Hh target gene expression, as can be detected by transiently transfecting these cells with a Gli-dependent firefly luciferase reporter. We observed that all four HPIs were able to repress Hh pathway activity in cells lacking Su(fu) function and therefore act downstream of this negative regulator (FIG. 2A). Since the Gli transcription factors are epistatic to Su(fu), we then mapped the activities of the HPIs relative to Gli1 and Gli2 (FIG. 2B). NIH-3T3 cells were transiently transfected with expression vectors encoding N-terminally FLAG-tagged Gli1 or Gli2 to induce constitutive Hh pathway activation, a Gli-dependent firefly luciferase reporter, and a construct for constitutive Renilla luciferase expression as a transfection control. In these overexpression assays, HPI-1 and HPI-2 were able to inhibit Gli-induced firefly luciferase expression in a dose-dependent manner, while HPI-3 and HPI-4 had no significant activity (FIG. 2B). In addition, HPI-2 preferentially inhibited Gli2, as its effects on Gli1-overexpressing cells were entirely due to a moderate increase in Renilla luciferase activity (FIG. 11). These data suggest that HPI-3 and HPI-4 counteract the activities of endogenous Gli1 and Gli2 through mechanisms that are circumvented by overexpressed Gli activators. In contrast, HPI-1 and HPI-2 are active against both endogenous and overexpressed Gli activators.

Example 4

Figure 3A:
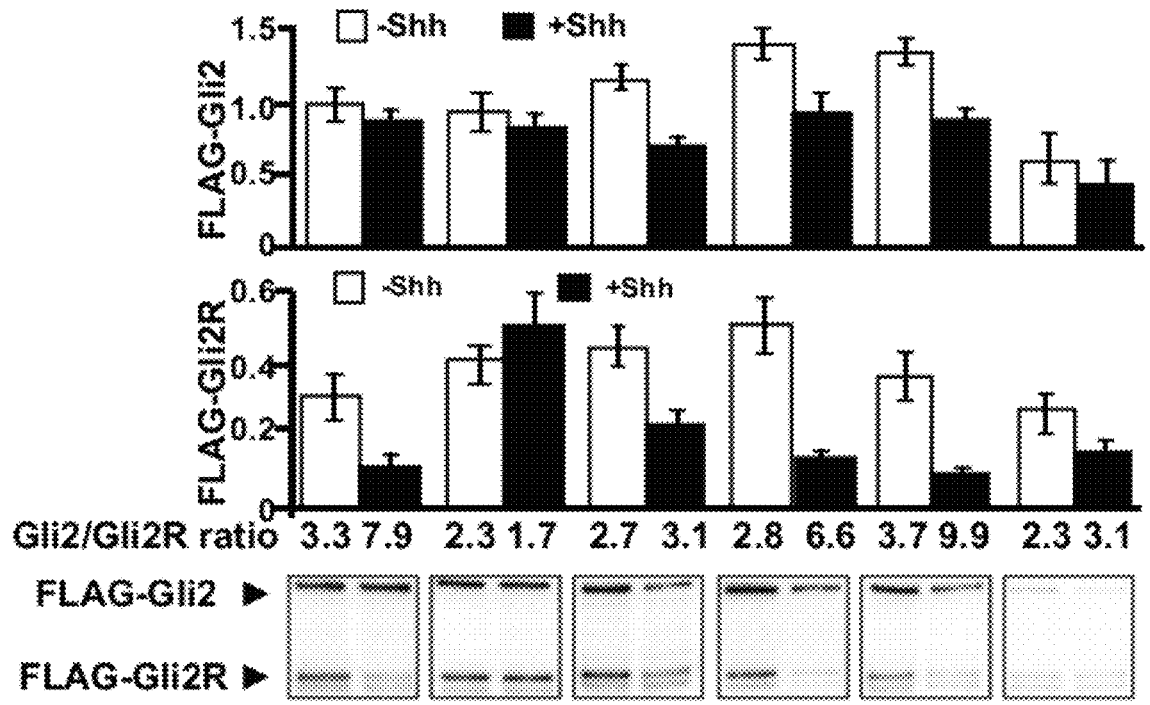
Figure 3B:
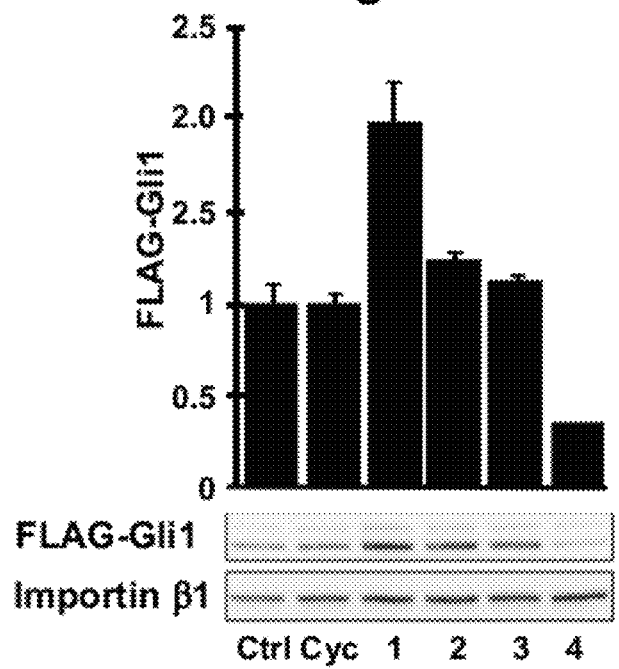
FIG. 3B: Effects of each HPI on cellular levels of FLAG-Gli1 in a stably transfected, clonal NIH-3T3 cell line. Representative immunoblotting results are shown, and quantitative data are the average band intensities from three independent experiments ± s.e.m, normalized with respect to FLAG-Gli1 levels in the control condition.

HPI modulation of Gli processing and stability. To further characterize the mechanisms by which HPIs can block Gli activator formation or function, we analyzed their effects on specific steps of Gli regulation, such as the phosphorylation- and proteosome-dependent formation of Gli repressors. Since Gli2 is the primary transcriptional activator in mammalian Hh signaling, we first focused our efforts on this Gli family member. We infected Shh-EGFP cells with a retroviral vector for FLAG-Gli2 expression and selected clones with low levels of the exogenous Gli2 protein (Shh-EGFP$^{FLAG-Gli2}$ cells). In these clones, the FLAG-Gli2 protein exists in both full-length and N-terminal repressor forms; Shh stimulation of these cells significantly reduces repressor formation, and cyclopamine can suppress the effects of Shh (FIG. 3A). Thus, the FLAG-Gli2 protein is regulated in a manner that recapitulates the endogenous transcription factor. We then treated Shh-EGFP$^{FLAG-Gli2}$ cells with the Hh pathway inhibitors in the absence and presence of Shh protein, and FLAG-Gli2 levels for each condition were analyzed by immunoblotting (FIG. 3A). In comparison to cells treated with a DMSO vehicle control, HPI-1-treated cells exhibited slightly elevated levels of full-length and repressor forms of FLAG-Gli2 under basal conditions and greater FLAG-Gli2 processing upon Shh stimulation. HPI-2 and HPI-3 moderately increased total FLAG-Gli2 levels as well but did not alter proteolytic processing of the transcription factor, and HPI-4 both decreased total FLAG-Gli2 levels and prevented Shh dependent stabilization of full-length FLAG-Gli2. To determine whether the HPIs affected Gli1 stability in similar manner, we also infected Shh-LIGHT2 cells with a retroviral vector for FLAG-Gli1 expression and selected clones with low levels of the exogenous Gli1 protein (Shh-LIGHT2$^{FLAG-Gli1}$ cells). FLAG-Gli1 levels associated with each of the HPIs were then assessed by immunoblotting. HPI-1 and HPI-4 increased and decreased FLAG-Gli1 stability, respectively, while neither HPI-2 or HPI-3 had any significant effect on FLAG-Gli1 levels (FIG. 3B).

Example 5

Figure 12:
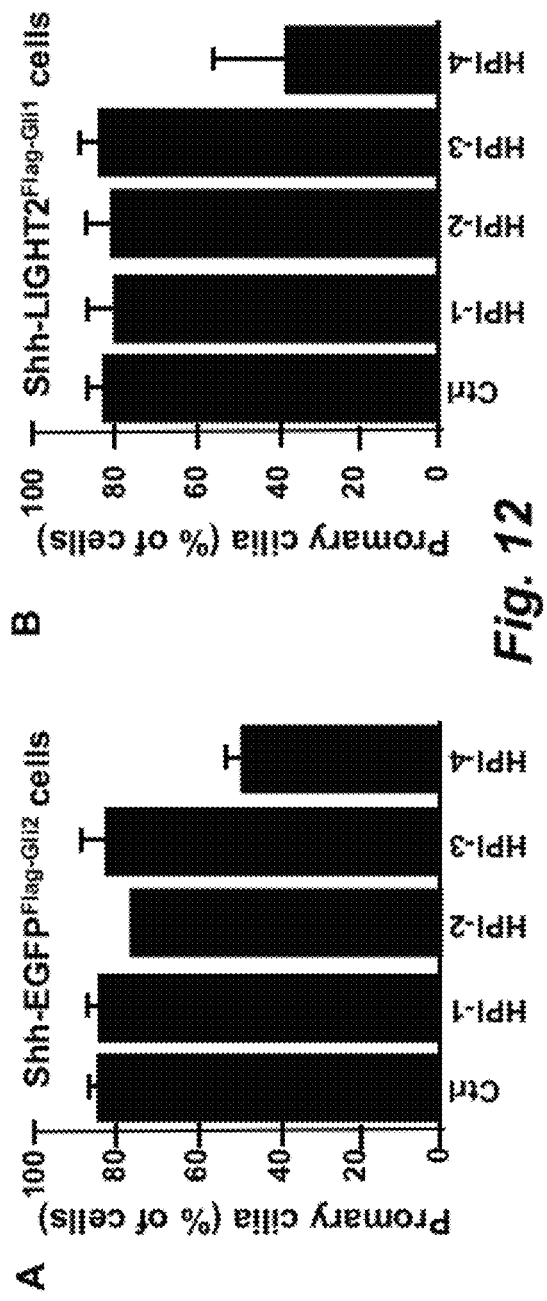
FIGS. 12A and 12B are graphs illustrating that HPI-4 inhibits primary cilia formation. Percentage of (FIG. 12A) Shh-EGFP$^{FLAG-Gli2}$ and (FIG. 12B) Shh-LIGHT2$^{FLAG-Gli1}$ cells with primary cilia after culturing them in medium containing DMSO, 15 μM HPI-1, 20 μM HPI-2, 30 μM HPI-3, or 30 μM HPI-4. Data are the average of two independent experiments ± s.d., each involving the analysis of at least 125 cells per condition.
Figure 13:
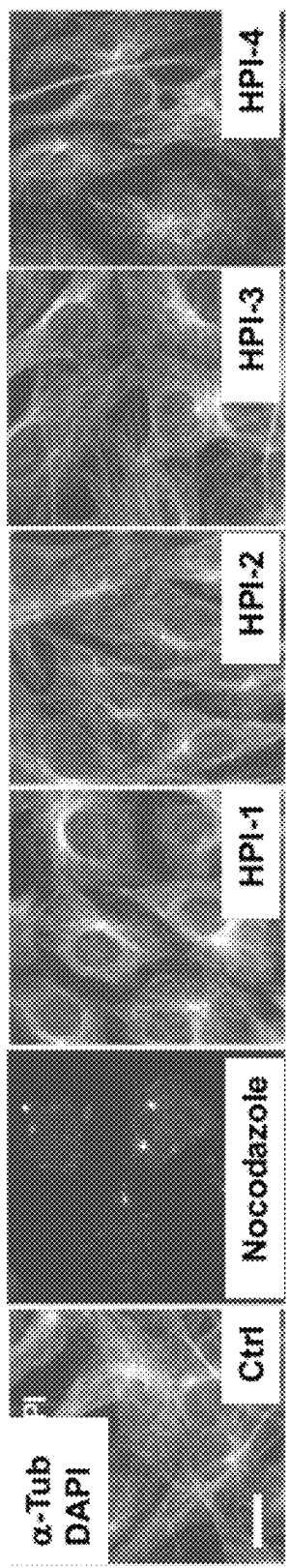
FIG. 13 are digital photographs showing that the HPIs of the disclosure do not perceptibly alter the general microtubule cytoskeleton. NIH-3T3 cells were treated with the individual HPIs and stained with an antibody against γ-tubulin. Doses of 15 μM HPI-1, 20 μM HPI-2, 30 μM HPI-3, and 30 μM HPI-4 were tested, and DMSO and 20 μM nocodazole were used as negative and positive controls, respectively. Scale bar: 10 μm.
Figure 14:
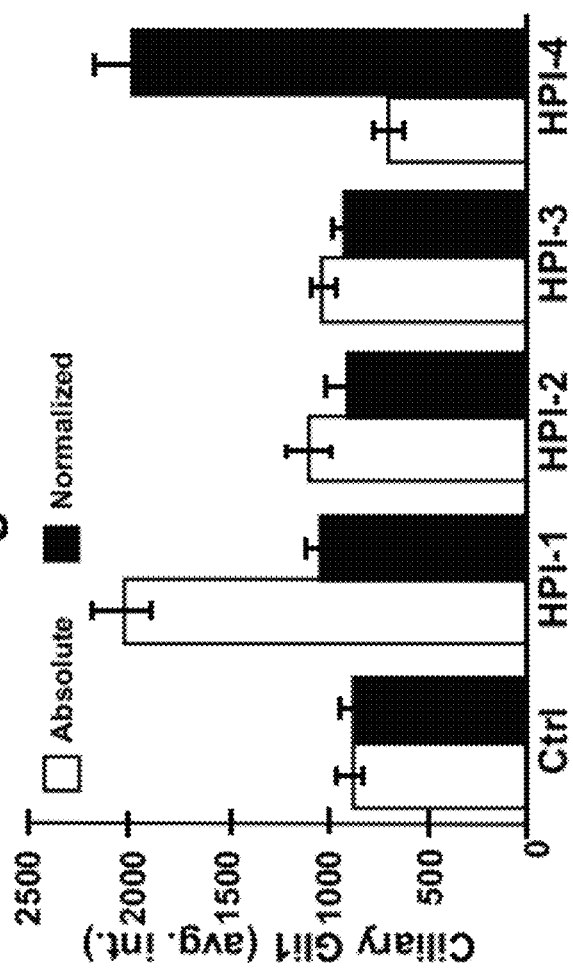
FIG. 14 is a graph showing the effects of the HPIs on ciliary levels of FLAG-Gli1. Quantification of ciliary FLAG-Gli1 levels in Shh-LIGHT2$^{FLAG-GLI1}$ cells treated with a DMSO vehicle control or individual HPIs and then analyzed by immunofluorescence (see FIG. 3H-L). Doses of 15 μM HPI-1, 20 μM HPI-2, 30 μM HPI-3, and 30 μM HPI-4 were used. Data are the average intensity of anti-FLAG antibody staining in at least 40 ciliary regions ± s.e.m, and both absolute ciliary intensities and those normalized with respect to total FLAG-Gli1 levels (see FIG. 3B) are shown. HPI-4 induces a ciliary accumulation of FLAG-Gli1 relative to its effects on total cellular levels of this transcription factor.

HPI modulation of Gli trafficking. We next analyzed the effects of the HPIs on Gli trafficking. In Shh-EGFP$^{FLAG-Gli2}$ cells, FLAG-Gli2 is distributed through the cytoplasm and nucleus in a punctate manner and localized to tip of the primary cilium, as visualized by antibodies against the FLAG epitope and the ciliary GTPase Arl13b (FIG. 3C-G). We treated Shh-EGFP-$^{FLAG-Gli2}$ cells with each of the antagonists and then observed the resulting FLAG-Gli2 distribution by immunofluorescence. In comparison to control cells, HPI-2, HPI-3, and HPI-4 increased ciliary levels of FLAG-Gli2 in a manner disproportionate to their effects on total FLAG-Gli2 levels (FIG. 3C-G and FIG. 3M). Cells cultured with HPI-4 also had truncated primary cilia, and this cellular organelle was absent in a significant fraction of HPI-4-treated cells (FIG. 3G and SI FIG. 7). The non-ciliary microtubule cytoskeleton, however, was not grossly perturbed by any of the HPIs (FIG. 13). We also assessed the subcellular localization of FLAG-Gli1 in the Shh-LIGHT2$^{FLAG-Gli1}$ cells. By immunostaining we observed FLAG-Gli1 in the cytoplasm, nuclei, and primary cilia of these cells, a distribution similar to that of FLAG-Gli2 in the Shh-EGFP$^{FLAG-Gli2}$ cells (FIG. 3H). However, FLAG-Gli1 localization was only significantly modulated by HPI-4, which reduced cytoplasmic levels of the transcription factor but retained nuclear FLAG-Gli1 (FIG. 3H-L). As observed with the Shh-EGFP$^{FLAG-Gli2}$ cells, HPI-4 also perturbed primary cilia formation in the FLAG-Gli1-expressing line and promoted accumulation of FLAG-Gli1 at the distal tip of this organelle relative to total FLAG-Gli1 levels (FIGS. 12 and 14). Ciliary FLAG-Gli1 levels were not significantly changed by any of the other HPIs.

Example 6

HPI activity can require Gli phosphorylation and is independent of PI3K and MAPK signaling. The HPI activity profiles suggest that all compounds block Hh target gene expression by acting at the level of the Gli transcription factors. Since Gli activity is known to be regulated by phosphorylation, we studied the effects of HPI-1 and HPI-2 on Hh pathway activation induced by the overexpression of Gli2 mutants lacking either PKA (Gli2 αPKA) or GSK3β (Gli2 αGSK) phosphorylation sites. The other HPIs were excluded from these studies, as they are ineffective against overexpressed Gli2. When overexpressed in NIH-3T3 cells, Gli2 αPKA mutant was partially resistant to HPI-1 and HPI-2, whereas wildtype Gli2 and the Gli2 αGSK mutant were inhibited to similar extents by the two compounds (FIG. 3J). These findings suggest that HPI-1 and HPI-2 enhance or work through Gli phosphorylation. HPI-1 and HPI-2 functions, however, do not appear to involve a general increase in PKA activity. HPI-1 does not induce the PKA-dependent phosphorylation of cAMP response element binding (CREB) protein, and the levels of CREB phosphorylation induced by HPI-2 are significantly lower than that observed in forskolin-treated cells (FIG. 15). In addition, the constitutive Hh target gene expression in Su(fu)$^{-/-}$ fibroblasts can only be partially inhibited by PKA activation, but both HPI-1 and HPI-2 reduce Hh pathway activity in these cells to near-basal levels.

We also assessed whether the HPIs act through PI3K or MAPK signaling, which have been implicated in Gli regulation. We activated the PI3K and MAPK pathways in NIH-3T3 cells with platelet-derived growth factor (PDGF), resulting in the phosphorylation of Akt and p44/p22 MAPK, respectively (FIG. 16). The PI3K inhibitor LY294002 prevented Akt phosphorylation under these conditions, and the Mek1/Mek2 inhibitor U0126 blocked p44/p22 MAPK phosphorylation. In contrast, none of the HPIs inhibited the PDGF-induced phosphorylation of either downstream substrate, indicating that the four Gli antagonists act independently of the PI3K and MAPK signaling pathways to block Hh target gene transcription.

Example 7

HPI repression of SmoM2-dependent proliferation of medulloblastoma progenitor cells. Having characterized how the HPIs functionally interact with known Hh signaling proteins, we investigated the ability of these compounds to block oncogenic Hh target gene expression. Due to the intimate link between dysregulated Hh pathway activation and medulloblastoma formation, our studies focused on cerebellar progenitor cells that give rise to these pediatric brain tumors. During brain development, cerebellar granule neuron precursors (GNPs) in the external granular layer proliferate in response to Shh protein secreted by neighboring Purkinje cells, after which they migrate into the internal granule layer and differentiate into mature granule neurons. The latter process requires Hh pathway downregulation, and abnormally sustained Hh target gene expression in GNPs ultimately leads to medulloblastoma formation. These oncogenic events can be recapitulated in murine models, including mice that are heterozygous for Ptch1 and those transgenically engineered for GNP-specific SmoM2 expression (Math1-Cre;SmoM2).

In both cases, the murine GNPs exhibit uncontrolled proliferation and elevated levels of the Hh target genes Gli1 and cyclin D1.

Figure 17:
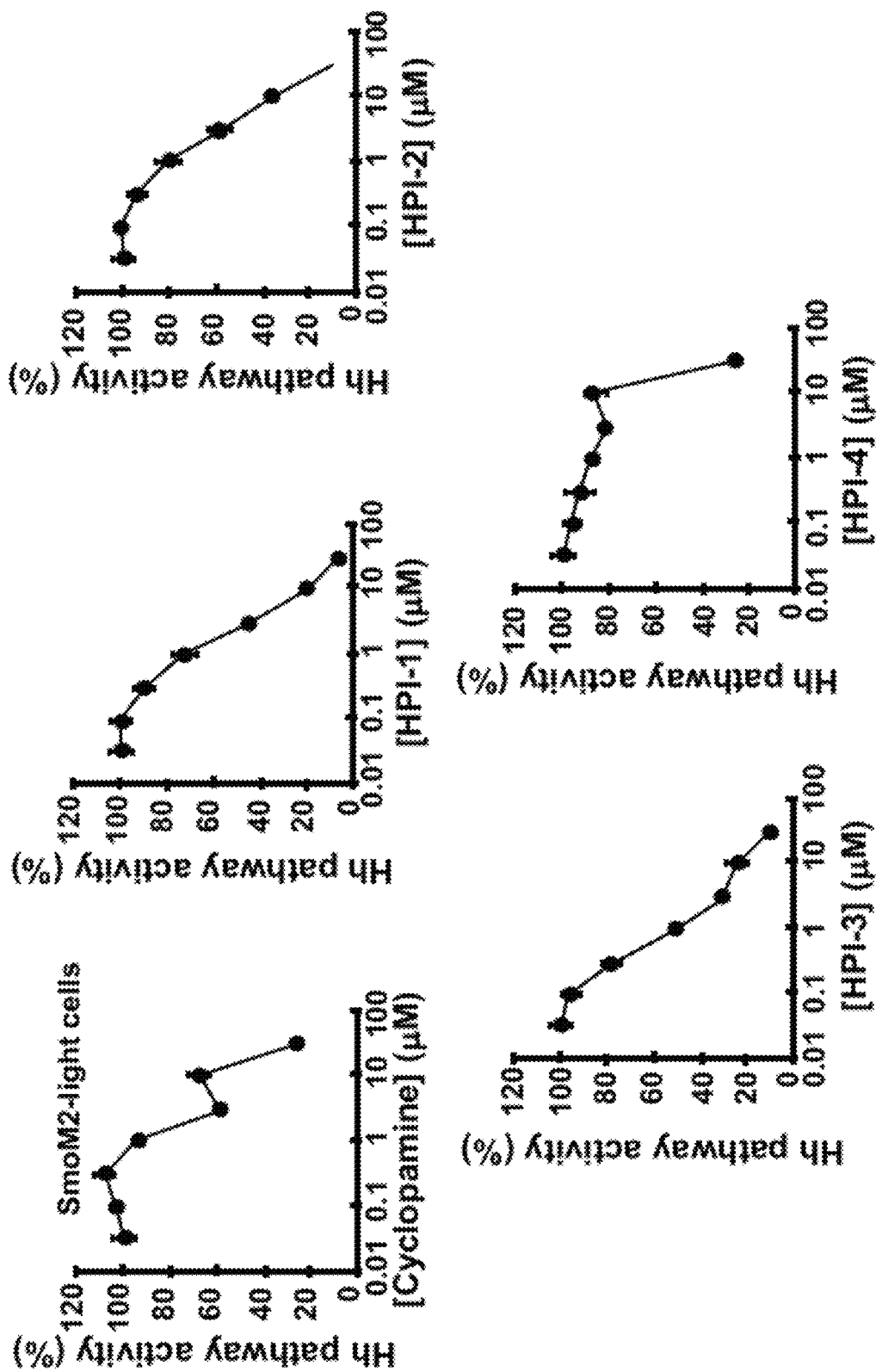
FIG. 17 is a series of graphs illustrating the inhibition of the Hh pathway activity in SmoM2-LIGHT cells by the HPIs. The constitutive Hh pathway activity in SmoM2-LIGHT2 cells can be inhibited by the HPIs with IC50s similar to those observed in Shh-stimulated Shh-LIGHT2 cells (see FIG. 1C). In contrast, cyclopamine is significantly less potent against SmoM2-dependent pathway activity (see FIG. 1A). Data are the average of triplicate samples ±s.d.

We therefore isolated GNPs from Math1-Cre:SmoM2 mice, which grow in a Hh ligand independent and cyclopamine-resistant manner in primary cultures. HPI-1 and HPI-4 significantly inhibited the proliferation of these neuronal progenitors, as measured by the fraction of cells exhibiting histone H3 phosphorylation (FIG. 4A-C). Both compounds also reduced cellular levels of cyclin D1 protein and Gli1 transcripts in the GNPs (FIG. 4D). In contrast, HPI-2 and HPI-3 did not block GNP proliferation. To extend these observations, we analyzed the effects of the HPIs on NIH-3T3 cells stably transfected for constitutive SmoM2 expression and Gli-dependent firefly luciferase activity (SmoM2-LIGHT cells). All compounds blocked Gli reporter expression in these cells, suggesting that SmoM2-induced Gli activity may be differentially regulated in neuron progenitor cells and fibroblasts (FIG. 17).

By conducting a high-throughput screen for small-molecule repressors of SAG, we have identified compounds, shown in Table 1, that block Hh target gene expression. These compounds include Gli antagonists Hh pathway inhibitors and compounds mechanistically distinct from cyclopamine and the SANTs. The HPIs do not inhibit the binding of BODIPY-cyclopamine to Smo-expressing cells, and are not functionally competitive with SAG. However, they can perturb the aggregation state of overexpressed Smo and attenuate Shh-dependent ciliary accumulation of endogenous Smo. These partial effects on Smo activity likely involve indirect mechanisms and do not solely account for the inhibitory activities of these compounds, since all HPIs can suppress Hh target gene expression induced by loss of Su(fu) and/or Gli protein overexpression.

Figure 5:
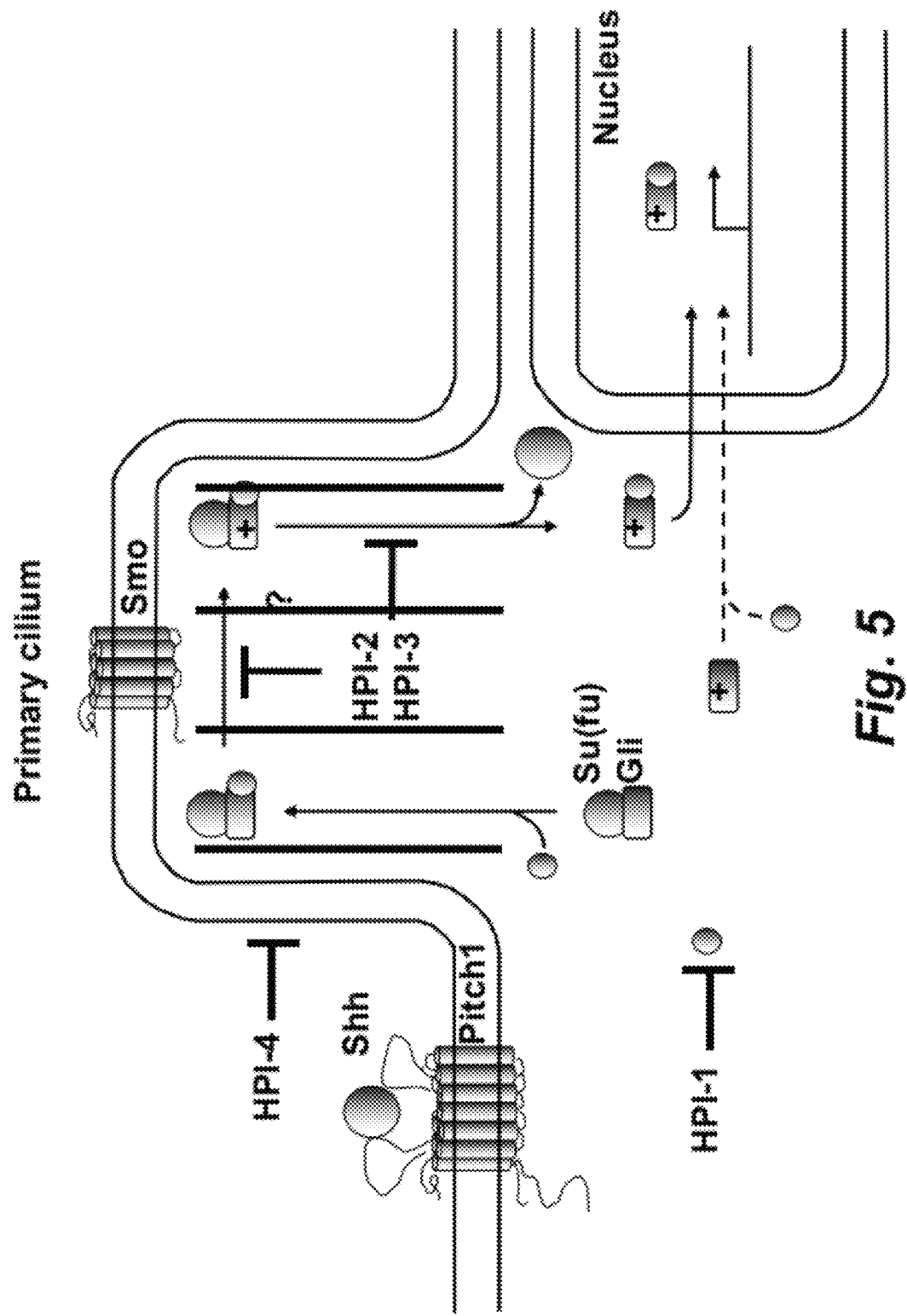
FIG. 5 schematically illustrates the Hh signaling pathway in its activated state and possible sites of HPI action. Upon Shh-Ptch1 binding, Smo accumulates in the primary cilium and promotes the stabilization and activation of full-length Gli proteins (red). The HPIs block this process through distinct mechanisms. HPI-1 inhibits a step required for both endogenous (solid arrows) and exogenous (dashed arrow) Gli activity, possibly involving a post-translational modification and/or a protein co-factor (green). HPI-2 and HPI-3 might either block the conversion of full-length Gli2 proteins into transcriptional activators or impede the retrograde ciliary transport of activated Gli2. HPI-4 disrupts formation of the primary cilium and therefore likely abrogates ciliary processes required for Gli function.

Shh-induced, Smo-dependent Gli2 stabilization is also intact in cells cultured with HPI-2 or HPI-3, demonstrating that Smo functionality is maintained in these cells. These observations indicate that the four HPIs block Hh pathway activation primarily through actions downstream of Smo. Our studies show that each of the four HPIs has a unique mechanism of action (FIG. 5). HPI-3 and HPI-4 map epistatically between Su(fu) and overexpressed Gli proteins, suggesting that they target regulatory mechanisms that control endogenous Gli function. Since HPI-3 does not alter Gli2 processing but increases the amount of ciliary Gli2, this compound might block trafficking of the activated transcription factor or prevent a step in Gli2 activation that facilitates retrograde ciliary transport. In comparison, HPI-4 reduces total cellular levels of Gli1 and Gli2, induces ciliary accumulation of both transcription factors, and shifts the nucleocytoplasmic distribution of Gli1. These effects on Gli localization and stability are likely indirect consequences of the primary cilium defects caused by HPI-4, reflecting the essential role of ciliary function in Gli regulation.

HPI-1 and HPI-2 counteract the activities of both endogenous and overexpressed Gli proteins. While not wishing to be bound by any one theory, HPI-1 is equipotent against overexpressed Gli1 and Gli2 and, therefore, may disrupt a cilium-independent process that is common to all Gli activators, such as a post-translational modification of the Gli protein and/or an interaction between the transcription factor and a protein co-factor. This putative step may promote Gli1 degradation and Gli2 stabilization, because full-length Gli1 and Gli2 repressor levels are elevated in cells treated with HPI-1. In contrast to HPI-1, HPI-2 preferentially inhibits Gli2 function, maintains Shh-regulated Gli2 processing, and promotes accumulation of ciliary Gli2. Like HPI-3, HPI-2 may target the activation and/or retrograde ciliary trafficking of full-length Gli2, however, the differential activities of HPI-2 and HPI-3 against endogenous and overexpressed Gli proteins indicate that the two inhibitors have distinct mechanisms of action.

HPI-1 antagonizes the transcriptional activities of overexpressed Gli1 and Gli2 with similar potencies, yet it stabilizes full-length Gli1 and promotes Gli2 processing. HPI-2 preferentially inhibits overexpressed Gli2. The HPIs also appear to alter the subcellular localization of Gli1 and Gli2 in an isoform-specific manner. Further studies will be required to establish the precise mechanisms by which the HPIs alter Gli function, as well as the direct cellular targets of these compounds. The HPIs of the present disclosure are mechanistically distinct from previously described Hh pathway inhibitors, including the Gli antagonists GANT-58, GANT-61, zerumbone, arcyriaflavin C, and physalin F. Nor do the HPIs significantly alter PI3K, MAPK, or PKA signaling, which can regulate Gli activity in a non-exclusive manner. Thus, the HPIs can be useful for probing the signaling mechanisms that control Gli function.

Finally, our studies illustrate the therapeutic potential of Hh pathway inhibitors that act downstream of Smo. HPI-1 and HPI-4 can block the proliferation of SmoM2-expressing GNPs and can be equally potent against medulloblastoma progenitor cells arising from loss of Su(fu) function, whereas the Smo inhibitor cyclopamine is ineffective against either oncogenic lesion.

The complexity of Gli regulation provides a variety of cellular targets that are amenable to small molecule modulation, and our discovery of HPIs with distinct mechanisms of action suggests that our large-scale chemical screen was not saturating.

Example 8

Constructs. Wildtype Smo was tagged at the C-terminus with three tandem Myc epitopes, CFP, or YFP in a pEGFP-C1-derived vector (lacking the EGFP cDNA). Wildtype Gli1 and Gli2 were amplified from a mouse cDNA library, tagged at the N-terminus with three tandem FLAG epitopes, and subcloned into pBMN-IRES-tdTomato-DEST or pBMN-IRES-hcRed-DEST vectors to provide constructs for retrovirus production. Expression constructs for Gli2 mutants lacking GSK3β or PKA phosphorylation sites were kindly provided. Gli-dependent and TCF/LEF-dependent firefly luciferase reporters have been described previously. A Gli-dependent EGFP reporter was generated from the corresponding firefly luciferase reporter. Small molecules HPI-1 through HPI-4 were purchased from ChemDiv, Spec, Chembridge, or Ambinter. Forskolin was obtained from Sigma, H89 and LY294002 were obtained from Cell Signaling Technology, and U0126 was obtained from Promega. BODIPY-cyclopamine was prepared as described previously.

Example 9

Cell lines. Shh-EGFP cells were generated by co-transfecting NIH-3T3 cells with the Gli-dependent EGFP reporter and pVGRXR (Invitrogen), followed by isolation of Shh-responsive cells by fluorescence-activated cell sorting (FACS) and clonal selection in medium containing 400 µg/mL zeocin. Wnt-LIGHT cells were generated by cotransfecting L cells with the TCF/LEF-dependent firefly luciferase reporter and pcDNA3, followed by selection in medium containing 1 mg/mL geneticin, and the isolation of Wnt3aresponsive clones. FLAG-Gli1- and FLAG-Gli2-expressing stable lines were generated by infecting Shh-LIGHT2 and Shh-EGFP cells, respectively, with the corresponding retroviral expression vectors, followed by FACS-based isolation of infected cells and immunofluorescence-based selection of individual clones with low levels of FLAG-Gli1 or FLAG-Gli2 expression. Primary cultures of cerebellar GNPs were obtained by triturating tumors derived from Math1-cre:SmoM2 mice and plating the dissociated cells onto poly-D-ornithine-coated plates.

Example 10

Immunoblotting. Lysates derived from NIH-3T3 cells, FLAG-Gli1- or FLAG-Gli2-expressing clones, or primary GNP cultures were resolved by SDS-PAGE, transferred to PVDF membranes, and immunoblotted with the appropriate primary and secondary antibodies. In the case of FLAGGli2, the lysates were first incubated with anti-FLAG agarose beads, and the immunoprecipitated proteins were analyzed by immunoblotting. Protein bands were quanitified using a ChemiDoc XRS system and Quantity One software (Bio-Rad).

Example 11

Immunofluorescence and image analysis. Cells were typically cultured on poly-D-lysine-coated glass coverslips and fixed with 4% paraformaldehyde in PBS for 10 min at room temperature. For experiments using FLAG-Gli1- or FLAG-Gli2-expressing lines, the fixed cells were also treated with methanol at −20° C. for 2-5 min. The fixed cells were washed with PBS, permeabilized with 0.2% Triton X-100, washed again with PBS, and then blocked in PBS containing 2% BSA or 1% normal goat serum. Primary antibodies were diluted in the blocking solution and used to stain cells for 2-3 h at room temperature. After washing three times with PBS, the fixed cells were treated with secondary antibodies in blocking solution for 1-2 hours at room temperature and then washed again with 22 PBS. The cells were then treated with DAPI-containing PBS, washed further with PBS, and then mounted in Prolong Gold (Invitrogen). Images of Smo localization were obtained on an inverted Leica DMIRE2 laser scanning confocal microscope, and images of FLAG-Gli1 and FLAG-Gli2 localization were obtained on an upright Leica DM4500B epifluorescence microscope. Quantitative image analyses were performed using Metamorph software (Universal Imaging).

Example 12

Shh-LIGHT2 assay for Hh pathway activation and library screening conditions. h-N-conditioned medium was prepared as previously described. Shh-LIGHT2 cells, an NIH-3T3-derived line stably transfected with Gli-dependent firefly luciferase (8XGliBS-FL) and constitutive Renilla luciferase (pRLTK, Promega) reporters, were cultured in DMEM (Invitrogen) containing 10% calf serum (CS, Hyclone), 400 µg/mL geneticin, 200 µg/mL zeocin, 100 U/mL penicillin, and 0.1 mg/mL streptomycin. For 96-well plate assays, Shh-LIGHT2 cells were seeded into each plate (10,000 cells/well) and cultured to confluency. The Shh-LIGHT2 cells were then grown in DMEM containing 0.5% CS, 100 U/mL penicillin, 0.1 mg/mL streptomycin, either 5% Shh-N-conditioned medium or 500 nM SAG, and various concentrations of the HPIs. After the cells were cultured for another 30 h, the resulting firefly and Renilla luciferase activities were measured using a Dual Luciferase Reporter kit (Promega) and a Veritas microplate luminometer (Turner Biosystems).

To screen 122,755 compounds from the Stanford High-Throughput Bioscience Center collection, the Shh-LIGHT2 assay was modified as follows. Shh-LIGHT2 cells were cultured in ten 10-cm tissue culture dishes using DMEM containing 10% CS, 100 U/mL penicillin, and 0.1 mg/mL streptomycin. When the cells reached >90% confluency, they were removed by trypsinization and diluted to a final volume of 50 mL medium. This cell suspension was then plated into clear-bottom, white-walled 384-well plates using a Titertek Multidrop dispenser (50 µL/well) and the cells were cultured until they reached confluency (3-4 days). The culture medium was then manually removed from each plate, and DMEM containing 0.5% CS, 100 U/mL penicillin, and 0.1 mg/mL streptomycin was added using the Multidrop dispenser (40 µL/well). The plates were then placed into an automated Staccato system (Caliper Life Sciences), which includes an automated CO2 incubator. An automated protocol was then run, in 3 which a Multidrop dispenser added 10 µL of a SAG solution in 0.5% CS medium (final SAG concentration of 500 nM) to columns 1-22 and 100 nL of each compound solution was added to the plates using a V&P Scientific pin tool, resulting in a final compound screening concentration of 10 µM. The SAG-free wells were used as negative controls. After 28-32 h, the assay medium was manually removed and the plates were frozen. To assay the firefly luciferase activities, the plates were thawed and placed into a Twister II stacker in the Staccato system. Bright-Glo luciferase substrate (Promega) was added by the Multidrop dispenser and the plates were analyzed on an Analyst GT microplate reader (2 min in the dark, 0.2 sec integration/well; Molecular Devices). Hits were defined as compounds that reduce the firefly luciferase signal by at least 50% compared to inhibitor-free controls. Primary hits were then re-tested in duplicate in an eight-point, 1:1 serially diluted doseresponse curve with a starting concentration of 20 µM. In these experiments, the median inhibitory concentration ($IC_{50}$) for both firefly and Renilla luciferase were determined using a Dual-Glo kit (Promega). Compounds that exhibited IC50s <10 µM and did not inhibit Renilla activity were selected for further study, including HPI-1 through HPI-4.

Example 13

HPI acquisition and synthesis. Upon the completion of the primary screen and dose-response studies, additional quantities of HPI-1 through HPI-4 were purchased from ChemDiv, Specs, Chembridge, or Abminter and their chemical compositions were verified by mass spectrometry. HPI-1 and HPI-2 were also re-synthesized through the following procedures.

Example 14

General synthetic procedures. Compounds were purified by flash chromatography using SiO2 (EM Science) as the stationary phase. $^1$H and $^{13}$C NMR spectra were taken on Varian Inova 400 and 500 MHz spectrometers in $CDCl_3$, and chemical shifts are reported as parts per million (ppm) downfield of the internal control trimethylsilane (TMS). High-resolution mass spectrometry (HRMS) data were obtained on a Micromass Q-TOF hybrid quadrupole liquid chromatography-mass spectrometer at the Stanford University Mass Spectrometry Facility. Purity of final compounds was assessed using a Waters 2795 HPLC system equipped with a dual wavelength UV detector, a reverse-phase (C18) 2.1×30 mm Agilent Zorbax HPLC column containing a 3.5-µm Stablebond stationary phase, and a mobile phase of water and acetonitrile, each containing 0.1% formic acid. E)-4-(2-methoxyphenyl)but-3-en-2-one. To a solution of o-anisaldehyde (3.00 g, 22.0 mmol) in acetone and water was added 2.0 mL of 50% NaOH, and the resulting mixture was allowed to stir for 3 days at room temperature. The reaction mixture was then extracted twice with dichloromethane, and the organic layers were pooled, dried with MgSO$_4$, and concentrated in vacuo to yield 1 as a white solid (4.12 g, 100%). Compound 1 was carried on to the next reaction without further purification. 5-(2-methoxyphenyl)cyclohexane-1,3-dione. To a solution of sodium ethoxide (0.53 g Na dissolved in 1.37 mL of ethanol, 23.4 mmol) in 15 mL of anhydrous ethanol was added diethyl malonate (3.60 mL, 23.4 mmol) followed by 1 (4.12 g, 23.4 mmol). The reaction mixture was refluxed for 16 h, after which it was cooled and extracted with chloroform/water. The aqueous layer was collected and distilled, leaving a residue, which was re-dissolved in 15 mL of 2N NaOH and refluxed for 4 h. After the solution was cooled to room temperature, 15 mL of 5N H2SO4 was added and the mixture was refluxed for an additional 2 h. Cooling of the reaction mixture then yielded 2 as a pale yellow precipitate, which was isolated by filtration and washed with water (5.00 g, 100%) HPI-1. To a dry round-bottom flask was added 3-hydroxybenzaldehyde (1.12 g, 9.16 mmol), dione 2 (2.00 g, 9.16 mmol), methoxyethyl acetoacetate (1.47 g, 9.16 mmol), ammonium acetate (1.10 g, 9.16 mmol), and the ionic liquid N,N-methylbutylimidazolium tetrafluoroborate (0.21 mL). The solution was stirred for 10 min at 90° C. The reaction mixture was applied directly to SiO2 column, and HPI-1 was purified by flash chromatography (ethyl acetate/hexanes, 6:4) to yield HPI-1 as pale yellow crystalline solid (2.69 g, 64%). $^1$H NMR (400 MHz, CDCl3/CD3OD): δ 7.18-6.61 (m, 8H), 5.06 (s, 1H), 5.01 (s, 1H), 4.12 (m, 2H), 3.81 (s, 3H), 3.55 (m, 2H), 3.33 (s, 2H), 3.32 (s, 3H), 2.64-2.49 (m, 4H), 2.36 (s, 3H). 13C (500 MHz, CDCl3): δ 196.6, 167.7, 157.1, 156.1, 151.0, 148.4, 144.6, 130.3, 129.1, 127.9, 127.1, 120.6, 119.8, 115.0, 113.3, 112.3, 110.6, 105.3, 70.4, 62.8, 58.7, 55.1, 42.3, 36.2, 33.1, 32.5, 19.2. HRMS (m/z): [M]+ calc. for C27H29NO6Na, 486.1893; found, 486.1891. HPLC (water/acetonitrile, 0.1% formic acid, 0-95%, 25 min): retention time, 10.3 min; 96% pure. Methyl-4,7-dimethoxy-1H-indole-2-carboxylate. A dry round-bottom flask was charged with NaN3 (0.900 g, 13.7 mmol) and 5 mL DMF. Methyl bromoacetate (1.20 mL, 13.1 mmol) was added dropwise to this solution, and the mixture was stirred for 2.5 h at room temperature. A white precipitate formed, and an equivalent volume of H2O was added. The resulting slurry was extracted three times with diethyl ether, and the pooled organic layer was washed six times with water, dried over MgSO4, and concentrated in vacuo to give methyl azidoacetate (1.5 g, 50%). This crude material was combined with 2,5-dimethoxybenzaldehyde (0.640 g, 3.83 mmol) in 15 mL of methanol (pre-chilled in an acetone/water dry ice bath), and the mixture was added at −10° C. to a solution of NaOMe (0.650 g, 11.5 mmol) in methanol 6 (6 mL). The yellow slurry was then stirred for 45 min at −10° C. and then overnight at 4° C. Ice water was added to the reaction, and the resulting precipitate was collected, dissolved in dichloromethane, dried over MgSO4, and concentrated in vacuo to give the azidocinnamate intermediate (0.65 g, 66%). The yellow solid was refluxed in 12 mL of xylenes for 30 min, after which N2 evolution ceased, and then refluxed for an additional 15 min. A yellow precipitate formed upon cooling of the reaction mixture, which was collected by filtration and washed with petroleum ether to give indole 3 as a yellow solid (0.46 g, 79%). 4,7-Dimethoxy-1-(2-oxopropyl)-1H-indole-2-carboxylic acid (4). α-Bromoacetone was prepared by combining 225 mL dichloromethane/methanol (7:3) and acetone (1.00 mL, 13.6 mmol) with tetrabutylammonium tribromide (6.20 g, 12.9 mmol). After 1 h, the red solution became colorless, and the dichloromethane/methanol was removed by distillation. The remaining solution was diluted with 25 mL of diethyl ether and washed three times with water to remove tetrabutylammonium bromide. The solution was than dried over MgSO4 and concentrated to give a 50%<-bromoacetone solution in diethyl ether. The N-alkyl indole was then prepared under anhydrous conditions by combining 3 (0.100 g, 0.425 mmol), α-bromoacetone (0.180 g, 1.28 mmol), anhydrous K$_2$CO$_3$ (0.170 g, 1.28 mmol), 18-crown-6 (16 mg, 0.064 mmol), and 0.5 mL DMF in a round-bottom flask fitted with a reflux condenser. This solution was allowed to stir at 80° C. for 3 h. The indole was then purified by SiO2 flash chromatography (ethyl acetate/hexanes, 7:3) and saponified with 2 N NaOH (aq) in methanol at 40° C. to obtain the carboxylic acid 4 (0.10 g, 83%). HPI-2. Cyclooctylamine (3.80 mL, 26.8 mmol) and ethyl formate (2.10 mL, 25.5 mmol) were stirred together for 3 h. Water (50 mL) was added to the reaction, and the mixture was extracted with ethyl acetate. The combined organic layers were dried over MgSO4, and 7 concentrated in vacuo to yield crude N-cyclooctylformamide (3.21 g, 80%). The formylated product was then dehydrated by phosphorus oxychloride (1.20 mL, 12.4 mmol) in 10 mL of petroleum ether/pyridine (3:5). Purification by SiO$_2$ flash chromatography using hexanes afforded the isocyanide product (2.1 g, 75%). An oven-dried and N2-purged sealed vial was charged with carboxylic acid 4 (122 mg, 0.44 mmol), N,N-dimethylethane-1,2-diamine (48.2 μL, 0.44 mmol), cyclooctyl isocyanide (60.6 mg, 0.440 mmol) and 300 μL of MeOH. After 16 h, the reaction mixture was purified directly by SiO2 flash chromatography (ethyl acetate/hexanes, 1:9) to yield HPI-2 as a tan crystalline solid (90 mg, 42%). $^1$H NMR (400 MHz, CDCl3): δ 7.62 (s broad, 1H), 7.31 (d, J=4.0 Hz, 1H), 6.58 (d, J=8 Hz, 1H), 6.35 (d, J=8 Hz, 1H), 5.59 (d, J=12 Hz, 1H), 4.21 (m, 1H), 4.08 (d, J=12 Hz, 1H), 3.92 (s, 6H), 3.72 (m, 2H), 3.57 (m, 2H), 2.76 (m, 2H), 2.48 (s, 6H), 1.75 (s, 3H), 1.64-1.24 (m, 14H). 13C (500 MHz, CDCl3): δ 178.46, 161.04, 148.50, 142.24, 127.59, 127.21, 120.35, 104.99, 104.96, 98.97, 65.19, 57.65, 55.89, 55.58, 52.82, 50.28, 44.86, 39.37, 32.13, 31.87, 26.88, 26.77, 25.26, 23.97, 23.20, 21.04. HRMS (m/z): [M]+ calc. for C27H40N4O4Na, 507.2947; found, 507.2948. HPLC (water/acetonitrile, 0.1% formic acid, 0-95%, 25 min): retention time, 9.35 min; 99% pure.

Example 15

BODIPY-cyclopamine/Smo binding assay. Smo-binding assays were conducted with BODIPY-cyclopamine and Smooverexpressing and HEK-293T cells as previously described, using a CMV-promoter based SV40 origin-containing expression construct for Smo-Myc3 (murine Smo containing three consecutive Myc epitopes at the C-terminus). HEK-293T cells were seeded into 24-well plates (30,000 cells/well) containing poly-D-lysine-treated 12-mm glass coverslips and cultured in 8 DMEM containing 10% fetal bovine serum (FBS, Invitrogen), 100 U/mL penicillin, and 0.1 mg/mL streptomycin. The cells were cultured until they reached 55 to 65% confluency (14-18 h), after which they were transfected with the Smo-Myc3 expression construct and FuGENE (Roche) according to the manufacturer's protocols. 24 h after transfection, the cells were washed with phosphate-buffered saline (PBS) and cultured in DMEM containing 0.5% FBS, 5 nM BODIPY-cyclopamine, and individual HPIs (20 μM). After 30 min, 10 μM Hoescht 33342 was added to each well, and the HPIs were incubated with the cells for an additional 60 min. The cells were then washed two times with PBS buffer, mounted in Prolong Gold (Invitrogen) and immediately imaged using a DM4500B compound microscope (Leica).

Example 16

Shh-EGFP assay for Hh pathway activation. A Gli-dependent enhanced green fluorescent protein reporter (Shh-EGFP) was generated by excising firefly luciferase cDNA from the 8XGliBs vector using NcoI/HpaI, and ligating in EGFP cDNA excised from the pEGFP-C1 vector (Clontech) by NcoI/Af/II digestion. NIH-3T3 cells were seeded into a 6-well plate (150,000 cells/well), cultured in DMEM containing 10% CS, 100 U/mL penicillin, and 0.1 mg/mL streptomycin for 24 h, and then transfected with 1 µg/well of Shh-EGFP plasmid, 50 ng/well of the zeocin resistance-conveying vector pVGRXR (Invitrogen), and FuGENE according to the manufacturer's protocols. The cells were grown to confluency and treated with DMEM containing 0.5% CS, 100 U/mL penicillin, 0.1 mg/mL streptomycin, and 5% Shh-N-conditioned medium for 30 h. Following Shh-N treatment, the adherent cultures were dissociated into single cells with 0.05% Trypsin-EDTA (300 µL/well; Invitrogen) for 5 min. The cells were then suspended in 1 mL of PBS containing 1% CS and sorted on a BD FACSAria (excitation: 488 nm; emission: 530/30 nm) to enrich for cells expressing EGFP in a Shh-N-responsive manner. Clonal populations were then cultured from single cells in DMEM containing 10% CS, 400 µg/mL zeocin, 100 U/mL penicillin, and 0.1 mg/mL streptomycin. To identify Shh-EGFP clones with maximum Shh-N-responsiveness, individual lines were seeded into 24-well plates (45,000 cell/well) and cultured for 48 h. The cells were then treated with DMEM containing 0.5% CS, 100 U/mL penicillin, 0.1 mg/mL streptomycin or the culture medium plus 5% Shh-N-conditioned medium. After 30 h, the adherent cultures were treated with 0.05% trypsin-EDTA (150 µL/well; Invitrogen) for 5 min to dissociate them into single cells. The cells were then resuspended in 500 µL of PBS containing 1% CS and analyzed on a BD FACSCalibur (excitation: 488 nm; emission: 530/30 nm). 10,000 cells were used to assess EGFP expression levels as a measure of Hh pathway activation, and the data was analyzed using FlowJo software (Tree Star). Clones with low basal EGFP levels and maximum Shh-Ninduced EGFP expression were selected for further use. To assess the inhibitory activities of the HPIs in the Shh-EGFP cells, a clonal line with maximum Shh-responsiveness was cultured in 24-well plates as described above. During treatment with Shh-N-conditioned medium, the cells were incubated either DMSO or individual HPIs (each at a concentration ten-fold greater than its IC50 in the Shh-LIGHT2 assay or 30 µM, whichever was lower: 15 µM HPI-1, 20 µM HPI-2, 30 µM HPI-3, and 30 µM HPI-4). The resulting EGFP levels were then evaluated by FACS and quantified using the FlowJo software.

Example 17

C3H10T(1/2) assay for Hh pathway activation. C3H10T (1/2) cells (ATCC) were plated into 96-well plates using DMEM containing 10% FBS, 100 U/mL penicillin, 0.1 mg/mL streptomycin, 5% Shh-N-conditioned medium, and various concentrations of the Hh pathway inhibitors. After approximately 40 h, the cells were washed with PBS and lysed in 50 µL of buffer containing 50 mM Tris-HCl, pH 9.5, 150 mM NaCl, 5 mM $MgCl_2$, and 1% Triton X-100. Alkaline phosphatase activities in the cell lysates were quantified by adding 10 µL of the lysate to 50 µL of CDP-Star chemiluminescence reagent (Perkin Elmer) and measuring the resulting chemiluminescence on a Veritas microplate luminometer.

Example 18

Ptch1$^{-/-}$ fibroblast assay for Hh pathway activation Hh pathway activation in Ptch1$^{-/-}$ fibroblasts was assayed as previously described, using the knocked-in β-galactosidase gene as a reporter for Hh target gene expression. Ptch1$^{-/-}$ fibroblasts were grown to 70-80% confluence in a 15-cm dish, trypsinized, and then resuspended in 40 mL of DMEM containing 10% FBS, 100 U/mL penicillin, and 0.1 mg/mL DMSO. This cell suspension was aliquoted into 96-well plates (150 µL/well), cultured overnight, and then treated with DMSO or various concentrations of the HPIs for 28 h. Cell viability was measured with CellTiter 96 AQ (Promega) according to the manufacturer's protocols. The cells were then lysed in Tropix lysis solution (30 µL/well; Applied Biosystems) and β-galactosidase levels were quantified by a Tropix Galacto-Star kit (Applied Biosystems) on a Veritas microplate luminometer.

Example 19

SmoM2-LIGHT assay for Hh pathway activation. SmoM2-LIGHT cells (previously named SmoA1-LIGHT cells) were grown to 70-80% confluence in a 15-cm dish, trypsinized, and then resuspended in 40 mL of DMEM containing 10% FBS, 100 U/mL penicillin, and 0.1 mg/mL DMSO. This cell suspension was aliquoted into 96-well plates (150 µL/well), cultured overnight, and then treated with DMSO or various concentrations of the HPIs for 28 h. Cells were then washed once with PBS then treated with 50 µL of passive lysis buffer (Promega). Hh pathway-dependent firefly luciferase activity in the lysates was quantified using Bright-Glo reagent and a Veritas microplate luminometer. Constitutive β-galactosidase activity was measured using the Tropix Galacto-Star kit.

Example 20

Wnt-LIGHT assay for Wnt pathway activation. Wnt3a-conditioned medium was prepared by culturing L cells stably expressing Wnt3a (ATCC) in DMEM containing 10% FBS, 100 U/mL penicillin, and 0.1 mg/mL streptomycin. After the cells reached 70% confluency, they were cultured in fresh medium, and the resulting Wnt3a-condition medium was collected 30 h later. To generate a Wnt pathway-reporter cell line (Wnt-LIGHT cells), L cells were seeded into a 6-well plate and cultured in DMEM containing 10% FBS, 100 U/mL penicillin, and 0.1 mg/mL streptomycin until they reached 50% confluency. The cells were then transfected with 1 µg/well of SuperTopFlash reporter, which contains seven TCF/LEF enhancer sites upstream of a basal promoter and firefly luciferase cDNA, 50 ng/well of constitutive Renilla reporter pRLSV40 (Invitrogen), 50 ng/well of the geneticin resistance-conveying vector pcDNA3 (Invitrogen), and FuGENE 6 according to the manufacturer's protocols. Clonal populations were obtained by culturing the transfected cells in DMEM containing 10% FBS, 1 mg/mL geneticin, 100 U/mL penicillin, and 0.1 mg/mL streptomycin. Individual clones were isolated by ring-cloning. To quantitatively assess Wnt pathway activation in the Wnt-LIGHT cells clones, the cells were then cultured in 48-well plates using DMEM containing 10% FBS, 400 µg/mL geneticin, 100 U/mL penicillin, and 0.1 mg/mL streptomycin. After the cells reached confluency, they were grown for another 24 h with either fresh culture medium or Wnt3a-conditioned medium. Through this process, a clone exhibiting maximum Wnt3a responsiveness and minimum basal pathway activation was identified. To determine whether the Hh pathway inhibitors affect Wnt signaling in the Wnt-LIGHT cells, the cells were cultured to 70-80% confluence in a 15-cm dish, trypsinized, and then resuspended in 40 mL of DMEM containing 10% FBS, 100 U/mL penicillin, and 0.1 mg/mL DMSO. This cell suspension was then aliquoted into 96-well plates (150 μL/well) and cultured overnight. The following day, the growth medium was replaced with Wnt3a-conditioned medium containing either DMSO or various concentrations of the HPIs. The cells were cultured further for 24-28 h, after which their firefly and Renilla luciferase activities were measured using a dual luciferase kit and Veritas microplate luminometer.

Example 21

FRET assay for Smo multimerization. To construct cyan and yellow fluorescent protein-tagged forms of murine Smo (Smo-CFP and Smo-YFP), CFP or FYP was fused in frame to the Smo C-terminus, using the Nhe//Sal/ sites in the pGE-Smo vector and the following primer sequences: 5'-GTA CGC TAG CAT GGT GAG CM GGG CGA GCT G-3' (SEQ ID NO.: 1) and 5'-GTA CGT CGA CTC ACT TGT ACA GCT CGT CCA TG-3' (SEQ ID NO.: 2). For FRET analysis of cultured cells, NIH-3T3 cells were seeded into 6-well plates (150,000 cells/well) and cultured in DMEM containing 10% CS, 100 U/mL penicillin, and 0.1 mg/mL streptomycin for 10-16 h. The cells were then transfected with 1 μg/well of the Smo-CFP and Smo-YFP expression constructs (1:1 mixture) and FuGENE 6, cultured for another 24 h, and treated with either 10 μM cyclopamine, 500 nM SAG, or individual HPIs (10 μM) in 13 the absence or presence of 10% Shh-N-conditioned medium for 5 h. The cells were washed with PBS buffer, fixed with 4% paraformaldehyde for 20 min, and mounted on slides in 80% glycerol. Fluorescence signals were acquired with the 100× objective of a Zeiss LSM510 confocal microscope with the following conditions: CFP was excited by 458-nm light and the emission was collected through a BP 480-520-nm filter. YFP was excited by 514-nm light and the emission was collected through a BP 535-590-nm filter. The CFP signal was obtained before and after photobleaching YFP(CFPBP and CFPAP, respectively) using the full power of the 514-nm laser line for 1-2 min at the top half of each cell, leaving the bottom half unbleached as an internal control. The CFP fluorescence intensity was analyzed using Metamorph software (Universal Imaging Corp.), and the energy transfer efficiency was calculated using the formula: FRET %=((CFPAP−CFPBP)/CFPAP)×100. Photobleached areas in 11-19 cells were analyzed for each experimental condition.

Example 22

Smo trafficking assay. NIH-3T3 cells were seeded into 24-well plates (40,000 cell/well) containing poly-Dlysine-coated 12-mm glass coverslips and cultured in DMEM containing 10% CS, 100 U/mL penicillin, and 0.1 mg/mL streptomycin until they reached 85-90% confluency. The medium was changed to DMEM containing 0.5% CS, 100 U/mL penicillin, and 0.1 mg/mL streptomycin and the cells were cultured for another 12 h. The cells were then treated with either DMSO, 15 μM HPI-1, 20 μM HPI-2, 30 μM HPI-3, or 30 μM HPI-4. Shh-N-conditioned medium was added to appropriate wells at a final concentration of 5%. After 12 h, the cells were fixed in 4% paraformaldehyde for 10 min at 4° C., washed three times with PBS, permeabilized for 1 min with PBS containing 0.1% Triton X-100, washed again three times with PBS, and then blocked with PBS containing 1% normal goat serum for 3 h. The coverslips were then treated with mouse anti-N-acetylated-<-tubulin (clone 6-11B-1, Sigma; 1:1,000 in blocking buffer) and rabbit anti-Smo antibody (1:2,000 dilution in blocking buffer) for 2 h at room temperature and washed 3×5 min with PBS. The coverslips were incubated next with Alexa Fluor 594-conjugated goat anti-mouse IgG and Alexa Fluor 488-conjugated donkey anti-rabbit IgG antibodies (Invitrogen; 1:1,000 dilutions in blocking buffer) for 1 h at room temperature. After washes with PBS and a 5-min incubation with 4,6-diamidino-2-phenylindole (DAPI), the samples were mounted using Prolong Gold (Invitrogen) and imaged with an inverted Leica DMIRE2 laser scanning confocal microscope. Ciliary Smo levels were quantified by designating ciliary regions according to Nacetylated-α-tubulin staining intensity using Metamorph software. Thresholded areas were further filtered for size and shape to remove non-ciliary regions, and additional ciliary regions were included manually. The ciliary regions were then transferred to the corresponding images of Smo antibody staining, and the average pixel intensity was recorded. Between 10-40 cilia were analyzed for each condition.

Example 23

Su(fu)$^{-/-}$ fibroblasts assay for Hh pathway activation. Su(fu)$^{-/-}$ fibroblasts were seeded into 24-well plates (60,000 cells/well) and cultured in DMEM containing 10% FBS, 10 μg/mL gentamicin, 100 U/mL penicillin, and 0.1 mg/mL streptomycin. After 24 h, the cells were transfected with Fugene HD (Roche), 8xGliBS-FL (95 ng/well), phRLSV40 (5 ng/well; Promega), and pEGFP-C1 (300 ng/well as a carrier; Clontech) according to the manufacturer's protocols. The cells were then treated with DMSO, 15 μM HPI-1, 20 μM HPI-2, 30 μM HPI-3, or 30 μM HPI-4 for 24 h. The resulting firefly and Renilla luciferase activities were measured using a dual luciferase kit and Veritas microplate luminometer.

Example 24

Hh pathway activation mediated by the overexpression of Gli, Gli2, Gli2αPKA, or Gli2αGSK. NIH-3T3 cells were seeded into 24-well plates (35,000 cells/well) and cultured in DMEM containing 10% CS, 100 U/mL penicillin, and 0.1 mg/mL streptomycin. The cells were co-transfected the following day with 220 ng/well pcDNA-derived Gli1, Gli2, or Gli2 phosphosite mutant expression vectors and 80 ng/well of a 1:15 mixture of phRLTK (Promega) and 8XGIiBS-FL. After transfection, cells were grown to confluence (approximately 48 h). The cell were then incubated for an additional 28-32 h in DMEM containing 0.5% CS, 100 U/mL penicillin, 0.1 mg/mL streptomycin, and either DMSO, 50 μM forskolin, 50 μM LY294002, or various concentrations of the HPIs. Firefly and Renilla luciferase activities were measured using a dual luciferase kit and a Veritas microplate luminometer.

Example 25

PKA-mediated CREB phosphorylation assay. NIH-3T3 cells were seeded into 12-well plates and grown to 80% confluency in DMEM containing 10% CS, 100 U/mL penicillin, and 0.1 mg/mL streptomycin. The cells were then cultured overnight in DMEM containing 0.5% CS, 100 U/mL penicillin, and 0.1 mg/mL streptomycin. The serum-starved cells were treated with DMSO or 10 µM H89 for 30 min, after which additional DMSO, 50 µM forskolin, 15 µM HPI-1, 20 µM HPI-2, 30 µM HPI-3, or 30 µM HPI-4 were added to the wells. The cells were cultured for an additional 2 h and then lysed in hot 2×SDS-PAGE sample buffer (100 mM Tris, pH 6.8, 200 mM DTT, 0.02% bromophenol blue, 16 20 mM NaF, 2 mM sodium orthovandate, 4% SDS, and 20% glycerol). After the samples were boiled for 5 min, they were resolved on 4-12% Criterion XT gels (Bio-Rad) and transferred to PVDF membranes (Millipore). The membranes were blocked overnight in TBST buffer (Trisbuffered saline with 0.1% Tween 20) containing 5% bovine serum albumin and then probed with either anti-phosphorylated CREB (87G3, Cell Signaling Technology; 1:1,000 dilution) or CREB (48H2, Cell Signaling Technology, 1:1,000 dilution) antibodies. After extensive washing in TBST, the membranes were incubated with horseradish peroxidase-conjugated donkey antirabbit IgG antibody (GE Healthcare, 1:10,0000 dilution), and the immunoblotted proteins were visualized using a SuperSignal West Dura Extended Duration kit (Pierce) and a ChemiDoc XRS system (Bio-Rad).

Example 26

PI3K and MAPK signaling assays. NIH-3T3 cells were seeded into 6-well plates and grown to 80% confluency in DMEM containing 10% CS, 100 U/mL penicillin, and 0.1 mg/mL streptomycin. Cells were then serumstarved for 8 h in DMEM containing 0.5% CS and either DMSO, 15 µM HPI-1, 20 µM HPI-2, 30 µM HPI-3, or 30 µM HPI-4. 50 µM LY294002 and 10 µM U0126 were used as positive controls. After serum starvation, cells were stimulated with 10 ng/ml PDGF BB for 30 min, washed in PBS, and lysed in buffer containing 50 mM Tris HCl pH 7.4, 250 mM NaCl, 20 mM NaF, 2 mM sodium orthovanadate, 2 mM EDTA, 2 mM PMSF, 1% Triton X-100, and EDTA free protease inhibitor cocktail (Roche). Cell lysates were clarified by centrifugation at 20,000×g and total protein concentrations were determined by the BCA assay (Pierce). 15 µg of protein from each lysate was mixed with 6×SDS-PAGE sample buffer (300 mM Tris-HCl, pH 6.8 containing 60% glycerol, 12% SDS, 600 mM DTT, and 0.05% bromophenol blue), boiled for 17 5 min and then resolved on 4-12% Bis-Tris Criterion XT gels. The electrophoresed samples were transferred to PVDF membranes and blocked overnight in TBST buffer containing 5% BSA. The membranes were then probed with anti-phosphorylated Akt (193H12, Cell Signaling Technology; 1:1,000 dilution), Akt (9727, Cell Signaling Technology, 1:1,000 dilution), phosphorylated p44/p42 MAPK (20G11, Cell Signaling Technology), or p44/p42 MAPK (137F5, Cell Signaling Technology) antibodies. After extensive washing in TBST, the membranes were incubated with horseradish peroxidase-conjugated donkey anti-rabbit IgG antibody (GE Healthcare, 1:10,000 dilution), and the immunoblotted proteins were visualized using a SuperSignal West Dura Extended Duration kit (Pierce) and a ChemiDoc XRS system.

Example 27

Generation of FLAG-Gli1 and FLAG-Gli2 retroviruses. Gli1 and Gli2 were amplified from a mouse oligo dT primed cDNA library with Phusion DNA polymerase (NEB), and subcloned into pCR-Blunt II-TOPO (Invitrogen) using the following polymerase chain reaction (PCR) primers (Gli1: 5'-GCG CCT CTC CCA CAT ACT AGA AAT CT-3' (SEQ ID NO.: 3), 5-TAG GAA ATA CCA TCT GCT TGG GGT TC-3' (SEQ ID NO.: 4)) and (Gli2: 5'-CAC CTG CAT GCT AGA GGC AAA CTT TT-3' (SEQ ID NO.: 5), 5'-TCA GGC CTA GTT AAC ACT TTG GGA CA-3' (SEQ ID NO.: 6)). The resulting vectors were used as templates for amplification of Gli1 and Gli2 with primers containing NotI and Bg/II restriction sites: (Gli1: 5'-GAA TGC GGC CGC GTT CAA TCC AAT GAC TCC AC-3' (SEQ ID NO.: 7), 5'-GAA GAT CTT TAG GCA CTA GAG TTG AGG-3' (SEQ ID NO.: 8)) and (Gli2: 5'-GAA TGC GGC CGC GGA GAC TTC TGC CCC AGC CC-3' (SEQ ID NO.: 9), 5'-GAA GAT CTT AGG TCA TCA TGT TTA AAA AC-3' (SEQ ID NO.: 10)). The PCR products were digested with NotI and Bg/II and ligated into the pCMV 3×FLAG 26 vector (Sigma). This plasmid construct was then used as a template for generating FLAG-tagged Gli1 and Gli2 cDNAs with flanking Gateway recombination sites using the common forward primer for FLAG 5'-AAA AAG CAG CCT CAG CCA CCA TGG ACT ACA AAG ACC ATG ACG GTG-3' (SEQ ID NO.: 11) and the reverse primers 5'-AGA AAG CTG GGT CTT AGG CAC TAG AGT TGA GGA ATT G-3' (SEQ ID NO.: 12) and 5'-AGA AAG CTG GGT CTT AGG TCA TCA TGT TTA AAA AC-3' (SEQ ID NO.: 13) for Gli1 and Gli2, respectively. These products were re-amplified with Gateway flanking primers (5'-GGG GAC AAG TTT GTA CAA AAA AGC AGG CTC A-3' (SEQ ID NO.: 14) and 5'-GGG GAC CAC TTT GTA CAA GAA AGC TGG GTC-3' (SEQ ID NO.: 15)) to add complete attB1 and attB2 sites and then recombined into the Gateway entry vector pDNR207 (Invitrogen). Entry vectors were sequence verified and recombined into the pBMNIRES-tdTomato-DEST or pBMN-IRES-hcRed-DEST vectors to generate FLAG-Gli1-tdTomato and FLAG-Gli2-hcRed retroviral constructs. The pBMN-IRES-tdTomato-DEST and pBMNIRES-hcRed-DEST vectors contain a Gateway cassette inserted into the polylinker region, followed by an internal ribosome entry sequence (IRES) for expression of the tdTomato and hcRed fluorescent proteins, respectively, as a reporter of infection efficiency. To generate retroviruses for FLAG-Gli1 or FLAG-Gli2 expression, HEK-293T cells (ATCC) were grown in DMEM containing 10% FBS, 100 U/mL penicillin, and 0.1 mg/ml streptomycin. The cells were cultured in 10-cm dishes and then transfected at 30% confluency in the following manner: 61 µL of 2 M CaCl2, 6 µg of pBMN vector (pBMN-Gli1-IRES-TdTomato or pBMN-Gli2-IRES-hcRed), and 3 µg of pCL-ECO retrovirus packaging vector (Imgenex) were diluted into 500 µL of nuclease-free H2O (Invitrogen) and added slowly to 500 µL of 2×HBS buffer (50 mM HEPES, pH 7.1, 280 mM NaCl, 1.5 mM Na2HPO4). Following a 1-min incubation at room temperature, the mixture was gradually added to a single 10-cm plate. Retroviral supernatants were collected 24 h later with a full medium replacement and then collected again after an additional 24 h. The combined supernatants were passed through a 0.45-19 µm filter and stored at −80° C. TdTomato or hcRed expression was used to confirm that a greater than 90% infection rate was achieved.

Example 28

Generation of cell lines stably expressing FLAG-Gli1 or FLAG-Gli2. To generate a FLAG-Gli1-expressing cell line, Shh-LIGHT2 cells were seeded into a 24-well plate (40,000 cells/well) and cultured in DMEM containing 10% CS, 100 U/mL penicillin, and 0.1 mg/mL streptomycin for 18 h. The cells were then infected with FLAG-Gli1-TdTomato retrovirus, and after 30 h, TdTomato-expressing cells were isolated on a Vantage SE/FACS DiVa cell sorter (excitation: 598 nm; emission: 575/26 nm). Clonal cell lines were cultured in DMEM containing 10% CS, 100 U/mL penicillin, and 0.1 mg/mL streptomycin, and individual clones that exhibited FLAG-Gli1 expression by immunofluorescence microscopy were isolated and expanded. To generate a FLAG-Gli2-expressing cell line, Shh-EGFP cells was added to a 24-well plate (40,000 cells/well) and cultured in DMEM containing 10% CS, 100 U/mL penicillin, and 0.1 mg/mL streptomycin for 18 h. The cells were then infected with FLAG-Gli2-hcRed retrovirus, and after 30 h, hcRed-expressing cells were isolated on a Vantage SE/FACS DiVa cell sorter (excitation: 598 nm; emission: 620/20 nm). Clonal cell lines were cultured in DMEM containing 10% CS, 100 U/mL penicillin, and 0.1 mg/mL streptomycin, and individual clones that exhibited FLAG-Gli2 expression by immunofluorescence microscopy were isolated and expanded.

Example 29

Analysis of Gli2 processing and Shh-dependent Gli2 stabilization. To analyze Gli2 processing, a Shh-EGFP clone expressing low levels of FLAG-Gli2 was cultured in 60-mm plates and grown to confluency in DMEM containing 10% CS, 100 U/mL penicillin, and 0.1 mg/mL streptomycin. The culture medium was then replaced with DMEM containing 10% CS, 100 U/mL penicillin, 0.1 mg/mL streptomycin, and either DMSO, 3 µM cyclopamine, 15 µM HPI-1, 20 µM HPI-2, 30 µM HPI-3, or 30 µM HPI-4. Each compound incubation was also done in the absence and presence of 5% Shh-N-conditioned medium, and the cells were maintained under these conditions for 24 h. The cells were subsequently solubilized in lysis buffer (100 µL/well; 50 mM Tris-HCl, pH 7.4, 1% Triton X-100, 250 mM NaCl, 2 mM EDTA, 20 mM NaF, 2 mM Na3VO4, 2 mM 2-mercaptoethanol, EDTA-free protease inhibitor cocktail (Roche)). This suspension was transferred to a 1.5-mL centrifuge tube and incubated on ice for 30 min, with vortexing every 5 min. The cell lysates were then centrifuged at 20,000×g at 4° C. for 20 min. Supernatants were removed, and a BCA protein assay was performed to quantify protein levels. Mouse anti-FLAG M2 agarose slurry (20 µL, Sigma) was pelleted by centrifugation and incubated with 800 ng of protein from each condition for 90 min at 4° C. and then washed three times with 1 mL of wash buffer (75 mM Tris-HCl buffer, pH 8.0 containing 225 mM NaCl, 0.5% Triton X-100) and centrifuged at 2,300×g at 4° C. The agarose beads were suspended in 30 µL of 1×SDS-PAGE sample buffer (50 mM Tris-HCl, pH 6.8 containing 10% glycerol, 2% SDS, 50 mM DTT, 200 mM 2-mercaptoethanol, and 0.001% bromophenol blue), and the mixture was boiled for 5 min. The samples were then resolved on a 4-12% Bis-Tris Criterion XT gel and transferred to a PVDF membrane. The membrane was dehydrated with methanol, and then probed with rabbit anti-FLAG antibody (Sigma; 1:1,000 dilution in blocking buffer (PBS 21 containing 3% non-fat dried milk and 0.01% Tween 20)) for 90 min. Blots were washed 4×5 min in PBS containing 0.01% Tween 20 and then probed with horseradish peroxidaseconjugated donkey anti-rabbit IgG antibody (GE Healthcare; 1:10,000 dilution in blocking buffer) for 1 h. Blots were washed 4×3 min in PBS, and the immunoreactive bands were detected with a SuperSignal West Dura kit and a ChemiDoc XRS system. Protein bands were quantified using Quantity One software (Bio-Rad). For each experiment, boxes of equal size were drawn around the FLAG-Gli2 and FLAG-Gli2R bands. Band intensities were then normalized to the average intensity for all bands in a given experiment. The results from all experiments were averaged and normalized relative to the basal level of FLAG-Gli2 (DMSO treatment without Shh-N-conditioned medium).

Example 31

Analysis of Gli1 stability. To analyze Gli1 expression levels, FLAG-Gli1-expressing Shh-LIGHT2 cells were cultured in 12-well plates and grown to confluency in DMEM containing 10% CS, 100 U/mL penicillin, and 0.1 mg/mL streptomycin. The culture medium was then replaced with DMEM containing 10% CS, 100 U/mL penicillin, 0.1 mg/mL streptomycin, and either DMSO, 15 µM HPI-1, 20 µM HPI-2, 30 µM HPI-3, or 30 µM HPI-4. The cells were maintained under these conditions for 24 h. The cells were subsequently solubilized in lysis buffer (100 µL/well; 50 mM Tris-HCl, pH 7.4, 1% Triton X-100, 250 mM NaCl, 2 mM EDTA, 20 mM NaF, 2 mM Na3VO4, 2 mM 2-mercaptoethanol, and EDTA-free protease inhibitor cocktail (Roche)). This suspension was transferred to a 1.5-mL centrifuge tube and incubated on ice for 30 min, with vortexing every 5 min. The cell lysates were then centrifuged at 20,000×g at 4° C. for 20 min. Supernatants were removed, and a BCA assay was performed to quantify protein levels. 15 µg 22 of protein from each sample was solubilized in 1×SDS-PAGE sample buffer (50 mM Tris-HCl, pH 6.8 containing 10% glycerol, 2% SDS, 50 mM DTT, 200 mM 2-mercaptoethanol, and 0.001% bromophenol blue) and boiled for 5 min. The samples were then resolved on a 4-12% Bis-Tris Criterion XT gel and transferred to a PVDF membrane. The membrane was dehydrated with methanol, and then probed with mouse anti-FLAG M2 antibody (Sigma; 1:1,000 dilution in blocking buffer (PBS containing 3% non-fat dried milk and 0.01% Tween 20)) for 90 min. The blots were washed 4×5 min in PBS containing 0.01% Tween 20 and then probed with horseradish peroxidase-conjugated sheep anti-mouse IgG antibody (GE Healthcare; 1:10,000 dilution in blocking buffer) for 1 h. The membranes were washed again 4×3 min in PBS, and immunoreactive bands were detected with a SuperSignal West Dura kit and a ChemiDoc XRS system. To probe for loading controls, the blots were rinsed with PBS, incubated for 1 min in methanol, washed 3×5 min in PBS, and then re-blocked for 1 h in PBS containing 5% non-fat dried milk and 0.1% Tween 20. The membranes were then incubated for 1 h with rabbit antiimportin β1 antibody (sc-11367, Santa Cruz Biotechnology; 1:1,000 dilution in blocking buffer), washed 3×10 min with PBS containing 0.1% Tween 20, incubated with donkey anti-rabbit IgG antibody (GE Healthcare; 1:10,000 dilution in PBS containing 0.1% Tween 20), washed 3×10 min with PBS containing 0.1% Tween 20, and then analyzed by chemiluminescence as described above. Protein bands were quantified using Quantity One software (Bio-Rad). FLAG-Gli1 and importin β1 bands were normalized to the average band intensities for each experiment. The ratio of these two values was then used to determine the relative amount of FLAG-Gli1 per condition. Results from three independent experiments were then averaged, and normalized to FLAG-Gli1 levels in DMSO-treated cells.

Example 32

Immunostaining of FLAG-Gli lines and NIH-3T3 cells. The FLAG-Gli1-expressing or FLAG-Gli2-expressing clonal cell lines were seeded into 24-well plates (80,000 cells/well) containing poly-D-lysine-coated 12-mm glass coverslips. The cells were grown to confluency in DMEM containing 10% CS, 100 U/mL penicillin, and 0.1 mg/mL streptomycin and then cultured for an additional 24 h in DMEM medium containing 0.5% CS, 100 U/mL penicillin, 0.1 mg/mL streptomycin, and either DMSO, 20 μM nocodazole, 15 μM HPI-1, 20 μM HPI-2, 30 μM HPI-3, or 30 μM HPI-4. The cells were subsequently fixed in 4% paraformaldehyde for 10 min at room temperature followed by treatment with methanol at −20° C. for 2 to 5 min. The cells were washed with PBS, permeabilized with 0.2% Triton X-100 for 2 to 5 min, and then blocked with PBS containing 2% BSA for 3 h at room temperature. The coverslips were then treated with mouse anti-FLAG M2 antibody (Sigma; 1:1,000 dilution in blocking buffer) and rabbit anti-Arl13b (10) (1:1,000 dilution in blocking buffer) for 3 h at room temperature and washed 3×5 min with PBS. The coverslips were incubated next with Alexa Fluor 594-conjugated goat anti-mouse IgG and Alexa Fluor 488-conjugated donkey anti-rabbit IgG antibodies (Invitrogen; 1:1,000 dilutions in blocking buffer) for 2 h at room temperature. After washes with PBS and a 5-min incubation with 4,6-diamidino-2-phenylindole (DAPI), the samples were mounted using Prolong Gold (Invitrogen) and imaged with an upright Leica DM4500B compound microscope. In order to quantify ciliary Gli2 localization, a circular region with diameter equal to the average width of cilia as determined by the anti-Arl13b antibody staining was manually placed at the distal end of each cilium. Regions were transferred from the anti-Arl13b antibody image to the anti-FLAG antibody image, and FLAG staining intensities within those areas were assessed. Between 40 and 80 cilia were analyzed for each condition. To normalize ciliary FLAG-Gli2 levels with respect to compound-dependent changes in total FLAG-Gli2 levels, the absolute average intensities for each condition were divided by the fold change in FLAG-Gli2 levels, as determined by the quantitative immunoblotting described above. Quantification of ciliary FLAG-Gli1 levels was performed in an analogous manner. Since HPI-4 perturbs primary cilia formation, only Arl13b-positive structures that could be clearly identified as cilia were used for Gli protein quanitification in HPI-4-treated cells. To assess cytoplasmic microtubule structures in cells treated with the HPIs, NIH-3T3 cells were cultured on poly-D-lysine-coated 12-mm glass coverslip, treated with the HPIs, and fixed with 4% paraformaldehyde as described above. In place of the methanol treatment, the cells were permeabilitized with PBS containing 0.1% Triton X-100 for 1 min. Washing, blocking, and antibody incubation steps were then conducted as before, using mouse anti-<-tubulin (DM1-A, Sigma, 1:2,000 in blocking buffer). Secondary antibody treatments, DAPI staining, mounting, and imaging were then conducted as described above.

Example 33

Analysis of Math1-cre:SmoM2 cerebellar GNP proliferation. To generate Math1-cre:SmoM2 tumors (11), a Math1-cre driver was used to conditionally express an activated Smo (SmoM2) allele. The Gt(ROSA)26Sortm1 (Smo/EYFP) Amc/J) mouse line was obtained from Jackson Laboratory (Bar Harbor, ME). Generation and characterization of Math1-cre transgenic animals that carry bacteriophage P1 cre recombinase under control of a 1.4 kb upstream Math1 enhancer element has been described previously. Primary cultures from Math1-cre:SmoM2 tumors were established by triturating tumor tissue and plating the dissociated cells onto poly-D-ornithine-coated plates in DMEM-F-12 with N2 supplement, 25 mM KCI, and antibiotics. After culturing the cells for 24 h, they were treated with individual HPIs (10 βM) for 24 h. Cell proliferation was then quantified by immunocytochemistry, and the expression of cyclin D1 and Gli1 were assessed by immunoblotting and RT-PCR, respectively. For immunocytochemistry, the primary cultures were fixed in 4% paraformaldehyde for 30 min at room temperature. The cells were then incubated in PBS containing 5% normal goat serum, 0.1% BSA, and 0.3% Triton X-100 for 1 h and with anti-phosphorylated histone H3 antibody (9706, Cell Signaling Technology; 1:500 dilution) overnight at 4° C. Each sample was then washed with PBS and incubated with Alexa Fluor 555-conjugated anti-rabbit IgG antibody (Molecular Probes; 1:1,000 dilution) and embedded. Immunofluorescently stained cultures were imaged using a Nikon Eclipse E600 microscope equipped with a 20×objective. Approximately 30,000 cells were analyzed for each experimental condition. To detect proteins by immunoblotting, non-denaturing lysates were prepared from Math1-cre:SmoM2 cultures using lysate buffer (50 mM HEPES, pH 7.4, containing 150 mM NaCl, 1 mM EDTA, 2.5 mM EGTA, 0.1% Triton X-100, 10% glycerol, and 1 mM DTT), resolved on a 10% SDS-PAGE gel, and transferred onto a PVDF membrane. The membrane was incubated overnight at 4° C. with anti-cyclin D1 (Ab-3, Neomarkers; 1:1,000 dilution) or anti-β-tubulin (T4026, Sigma; 1:5,000 dilution) antibodies. After extensive washing in 10 mM Tris-HCl, pH 8.0 containing 0.1% Triton X-100, the membrane was incubated with horseradish peroxidase-conjugated goat anti-rabbit IgG (Pierce; 1:10,000 dilution) or donkey anti-mouse IgG (Jackson Laboratories, 1:10,000 dilution) antibodies, and the immunoblotted proteins were visualized with an ECL kit (Amersham) and a Konica SRX-101A film processor. For RT-PCR analyses, total RNA from Math1-cre:SmoM2cultures was extracted with TRIzol (Invitrogen) according to the manufacturer's protocol. The RNA was purified further 26 with an RNeasy kit (Qiagen), and then reverse-transcribed with an Advantage RT-for-PCR Kit (Clontech) and random hexamer primers. PCR was performed using a Stratagene RoboCycler Gradient 96 temperature cycler with a Hot Top Assembly, the Titanium Taq DNA polymerase (Clontech), and the following primers: Gli1: 5'-ACA GCG GGG GCA GAA GTC G-3' (SEQ ID NO.: 16), 5'-CCT CAG CCC CAG TAT CCC CAG TCG-3' (SEQ ID NO.: 17); β-actin: the Clontech Mouse β-Actin Control Amplimer Set. Typical PCR conditions were as follows: an initial denaturation at 95° C. for 1 min followed by 28 cycles of denaturation at 94° C. for 45 sec, annealing at 60° C. for 45 sec, extension at 70° C. for 2 min, and a final extension at 72° C. for 7 min. The resulting PCR products were analyzed on 2% agarose gels.

Example 34

HPIs in a mouse tumor model: To study the efficacy of the HPIs of the disclosure in cancer, a mouse model of medulloblastoma is used. Two useful transgenic mice have been generated. The first mouse has a Ptc1+/−; p53−/− genotype and a reporter construct comprising the Math1 promoter operably linked to firefly luciferase. The second mouse has a Su(fu)+/−; p53−/− genotype and a reporter construct comprising the Math1 promoter operably linked to firefly luciferase. These mice spontaneously generate medulloblastomas which can be tracked, as the Math1 promoter will express luciferase in a tissue specific manner in the granule cells in the developing cerebellum. As luciferin is not toxic to the mouse, HPIs of the disclosure will be administered to the mouse and parameters such as tumor growth/shrinkage will be measured by repeated luciferase injection over several different time points without necessarily sacrificing the mouse.

A second experiment to utilize these mice is where tumors taken from the mice described are dissected and disassociated from the parent mice and injected into the flank of an athymic (nude) mouse. The HPIs of the disclosure are used to treat the tumor, either as a single agent or in combination with another agent. Again, because the mice will be expressing the luciferase marker, the mice will be whole body imaged at different time points in order to determine efficacy, rather than necessarily sacrificing the mouse.

Example 35

In addition to yielding more potent derivatives, different syntheses will provide modifications of the pharmacophore to create probes of HPI-1 function. For those HPIs in Table 1 and Table 2 denoted to interact with Gli polypeptides, these compounds may be modified for use in biochemical precipitation or crosslinking experiments in order to determine the binding sites of individual HPIs to specific sites on the Gli polypeptides.

In particular, the methoxyl derivative of HPI-1 (see Table 2, HPI-1.15) has an $IC_{50}$ of approximately 0.7 µM in the Shh-LIGHT2 assay as a diastereomeric mixture. This compound has been further separated into four diastereomers.

The development of HPI-1 reagents for these target identification strategies may require further SAR analyses; for example, certain changes to the $R_1$ substituent are tolerated by the HPI-1 target, suggesting that synthetic probes can be obtained by modifying this group. To generate a HPI-1 affinity matrix, an aminomethylphenyl group is placed at the $R_1$ position and a phenyl group is placed at the $R_2$ position (to take advantage of the increased potency of the des-hydroxy HPI-1 derivative). The primary amine could then be functionalized with a linker or tag (e.g. biotin) for attachment to a polymeric support, enabling binding protein isolation by affinity chromatography. Another example would be to place a hydroxyphenyl moiety at the $R_1$ position. The HPI-1 analog could then be converted into a highly sensitive photo-crosslinking reagent by transforming the ketone into a diazirine and halogenating the hydroxyphenyl group with $^{125}I$. Crosslinking of the HPI-1 target with this reagent would facilitate its isolation by sequential rounds of protein fractionation. In an alternative example, if large $R_1$ substituents are not tolerated by the HPI-1 target, a propynylphenyl moiety could be incorporated at this position in combination with the diazirine modification. This reagent would allow one to biochemically isolate photo-crosslinked targets, since the terminal alkyne could be functionalized with a "pull-down" tag after protein crosslinking and denaturation. Similar approaches have been successfully used to isolate proteins crosslinked with activity-based probes and to identify the targets of biologically active small molecules. These types of methodologies would be expanded to encompass all HPIs of the disclosure as similar approaches have been successfully used to isolate proteins crosslinked with activity based probes (Salisbury and Cravatt, QSAR Comb. Sci. (2007) 26:1229-1238). In all of the above approaches, specific HPI-1/target interactions would be distinguished from non-specific protein binding by their ability to be blocked by soluble, unmodified HPI-1.

It should be emphasized that the synthetic probes described above are not meant to be a complete account of HPI-1-based probes but are illustrative of the types of probes that can be prepared. For example, the photocrosslinking group could also be installed as phenyl(trifluoromethyl)diazirine at the $R_1$ position of the cyclohexenyl ring system.

Example 36

Use of HPIs in bone formation: To determine the ability of HPIs of the disclosure to antagonize the Hh pathway during development, HPIs will be tested in a mouse model of bone growth. In postnatal mammals, most of the skeleton formation occurs by the replacement of cartilage with osteogenic cells in what is termed endochondral ossification. This process is a spatiotemporally organized progression of chondrocyte proliferation, differentiation into hypertropic cells, infiltration by osteoblasts and blood vessels and apoptosis. The Hh pathway member involved in this process is Ihh, which controls expression of parathyroid hormone related peptide (PTHrP) at the distal ends of the growing bone. Ihh also promotes the formation of osteoblasts within the perichondrium adjacent to the pre-hypertrophic and hypertropic condrocytes. These osteoblasts form the bone collar, a precursor of the outer cortical bone, and invade the hypertrophic cartilage matrix to create trabecular bone. Loss of Ihh, Smo or Gli2 function during murine embryogenesis is associated with severe bone defects, showing a marked reduction in chondrocyte proliferation, ectopic hypertrophic differentiation, delayed calcification, and bones that are about 20% of normal size. Preliminary studies have shown that small molecule Smo antagonists can inhibit murine postnatal bone growth, and provide a basis for determining the ability of HPIs of the disclosure to similarly inhibit bone development.

To determine if HPIs of the disclosure effect bone growth, HPIs will be administered to 10 day old postnatal mice by oral gavage or intraperitoneal injection for a period of four days. Initially, HPIs of the disclosure will be administered in twice daily doses of 50 and 100 mg/kg, with ten mice for each group. Littermates will be treated with corn oil as a negative control and cyclopamine as a positive control. HPIs of the disclosure are predicted to induce dwarfism that is detectable after four days of treatment and grossly evident after six weeks. Disruption of bone development will also be examined at the cellular level, by staining dissected femurs with Alizarin red and Alcian blue to show bone and cartilage respectively. Developmental defects will include, but are not limited to; cellular disorganization, premature vascularization, growth plate defects and loss of cortical and trabecular bone. Other cellular markers that will be used are; proliferating cell nuclear antigen (PCNA) and Sox9 for examining chondrocyte proliferation, collagen type X (chondrocyte hypertrophy), PECAM-1 (blood vessel invasion), collagen type 1 (trabecular bone formation) and PTHrP expression. Finally, Gli1 and Ptc1 expression will be detected by in situ hybridization to confirm that the Hh pathway is being inhibited.

Example 37

Synthesis of HPIs: Synthesis of HPIs of the disclosure can be performed by any means by one of skill in the art. However, an example of synthesis of HPI-1 is provided. HPI-1 can be readily prepared in a one-pot synthesis using the Hantzsch reaction (Loev et al., J. Pharm. Pharmacol. (1972) 24:917-918) (see also FIG. 10 panel A-B). This synthetic transformation generates the dihydropyridyl pharmacophore from an aldehyde, two 1,3-diones, and ammonia acetate in high yields. First, one of the 1,3-diones was prepared in two synthetic steps (FIG. 10, panel A). 4-(2-methoxyphenyl)but-3-en-2-one was synthesized by an aldol condensation of 2-methoxybenzaldehyde and acetone, followed by dehydration. Reaction of the α,β-unsaturated ketone product with ethyl malonate generated an ester intermediate, which yielded the desired aryl-substituted 1,3-dione upon decarboxylation. HPI-1 was then synthesized by heating a mixture of the aryl-substituted 1,3-dione, 3-hydroxybenzaldehyde, 2-methoxyethyl acetoacetate, ammonium acetate, and the ionic liquid 1-butyl-3-methylimidazolium tetrafluoroborate (BMIM.BF$_4$) (FIG. 10, panel B). Purification by silica gel chromatography yielded the final product as a mixture of four diastereomers in 63% overall yield. Using this procedure, it is possible to synthesize gram quantities of HPI-1, which would be sufficient for both research and clinical applications. HPI-1 derivatives set forth in Table II were similarly prepared.

Example 38

Figure 18:
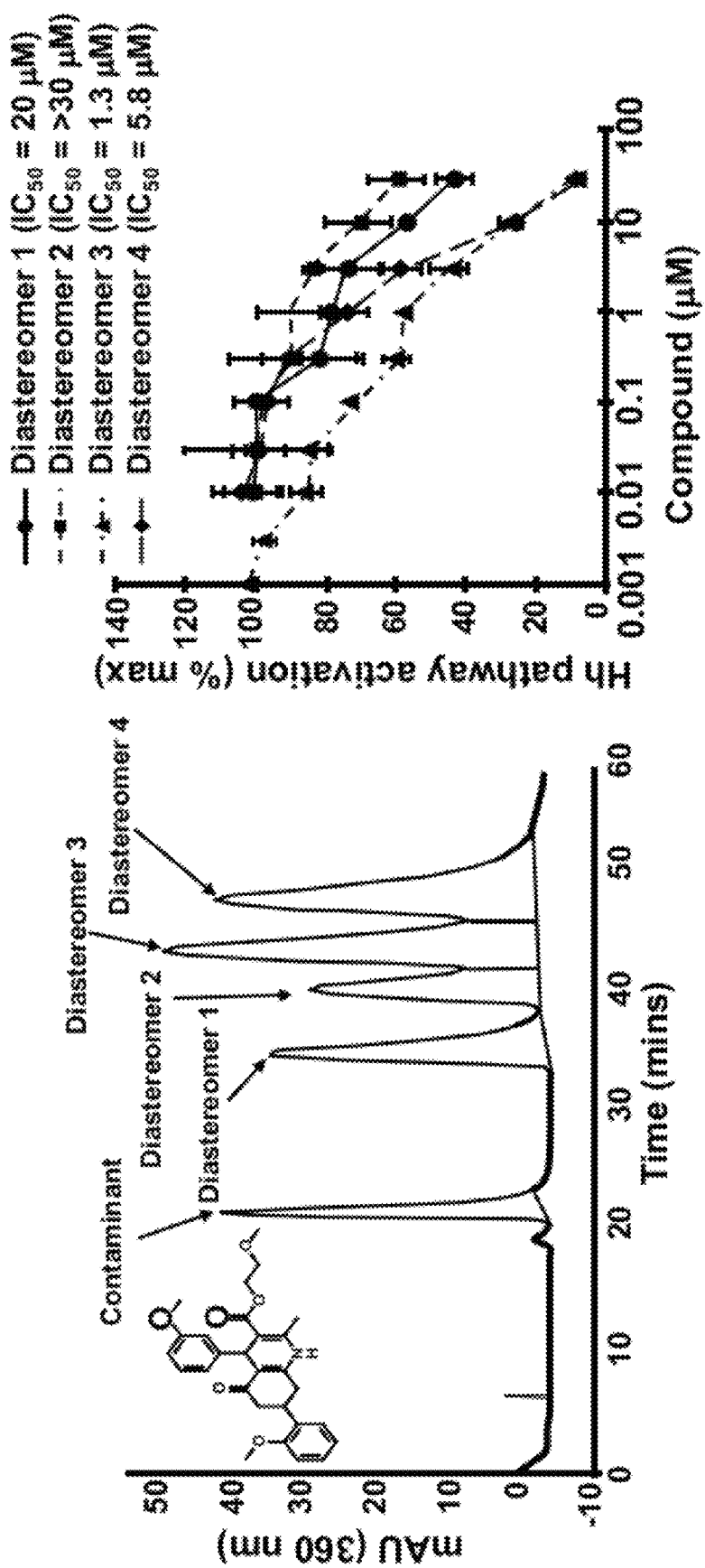
FIG. 18 shows graphs illustrating the chiral separation of an O-Me derivative of HPI-1.

Purification and identification of HPI-1 stereoisomers: HPI-1 is a mixture of four diastereomers, and structure-activity relationship (SAR) data suggests that the activity of this Gli antagonist is due to only one stereoisomer. To determine the active principle in the HPI-1 mixture and purify this diastereomer, chiral dihydropyridine compounds are purified using Pirkle stationary phases, which contain chiral recognition groups, composed of π-electron acceptors and/or π-electron donors. Accordingly, the four HPI-1 diastereomers were separated using an analytical Whelk-O-1 phase HPLC column, which is based upon 1-(3,5-dinitrobenzamido)-1,2,3,4-tetrahydrophenanthrene (mobile phase: 20% ethanol/80% hexane), as shown in FIG. 18.

Previous efforts to resolve dihydropyridyl stereoisomers have relied upon lipases that hydrolyze the ester group in a stereospecific manner and chiral alkaloids that stereoselectively co-crystallize with organic acids. In one approach HPI-1 is treated with Lipase PS (Amano Enzyme, Inc.), which has been previously used to obtain dihydropyridyl acids in >99% enantiomeric purity (Ebiike et al., Chem. Pharm. Bull. (1992) 40:1083-1085 (Japanese)). The resulting products are analyzed by chiral HPLC and compared with the known chromatography retention times of the HPI-1 esters and acids. Acids liberated by lipase-mediated hydrolysis are separated from the remaining esters by a standard aqueous/organic separation, providing at least a partial purification of the biologically active diastereomer. If the active isomer is a Lipase PS substrate, it can be further separated by any remaining contaminants by co-crystallizing it with chiral alkaloids such as cinchonidine or cinchonine. Similarly, if the active isomer is not hydrolyzed by this enzyme, it can be chemically saponified to the carboxylic acid and then mixed with an alkaloid for crystallization. The acid/alkaloid crystals are then used to determine the absolute stereochemical configuration of the active compound by x-ray diffraction. Re-esterification of the purified acid would then yield the desired HPI-1 or HPI-1 derivative.

As more HPIs or HPI-1 derivatives are identified, the same strategy is pursued to obtain these antagonists in diastereomerically pure form. If it is observed that these resolution procedures do not sufficiently discriminate between HPI-1 or HPI-1 stereoisomers, then a preparative-scale Whelk-O-1 column is used.

The hedgehog pathway inhibitors, or their pharmaceutically acceptable salts may contain one or more asymmetric centers and may thus give rise to enantiomers, diastereomers, and other stereoisomeric forms that may be defined, in terms of absolute stereochemistry, as (R) or (S) or, as (D) or (L) for amino acids. The present disclosure is meant to include all such possible isomers, as well as, their racemic and optically pure forms. Optically active (+) and (−), (R) and (S), or (D) and (L) isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

TABLE 1

| Compound Structure[a] | Compound Structure and HTBC Compound ID | BODIPY-cyclopamine competition | Microtubule disruption | IC50 (uM) Shh/Shh-LIGHT2 cells | IC50 (uM) SAG/Shh-LIGHT2 cells | % Inhibition Shh-GFP cells | IC50 (uM) Shh/C3H 10T[1/2] cells | % Inhibition Su(fu)-/- MEFs | IC50 (uM) Gli1 Transfected or Infection | IC50 (uM) Gli2 Transfected |
|---|---|---|---|---|---|---|---|---|---|---|
| 1 | STF-083089-1 | No | No | 0.25 | 0.21 | 74.4 | 0.9 | 95.2 | 1 | 3 |
| 2 | STF-086469-1 | No | No | 1.6 | 2.2 | 80.9 | 0.8 | 6.26 | >30 | >30 |
| 3 | STF-083392-1 | No | No | 0.5 | 0.55 | 60.5 | 0.9 | 92.8 | 1 | 2 |
| 4 | STF-010544-1 | No | No | 1.8 | 4 | 63 | 0.8 | −7.55 | >30 | >30 |
| 5 | STF-123397-1 | No | No | 1 | 0.8 | 84.9 | 0.9 | 45.7 | 7 | 10 |
| 6 | STF-093855-1 | No | No | 1 | 1 | 84.5 | 0.45 | 90 | 1.5 | 1.5 |
| 7 | STF-104402-1 | No | No | 1.6 | 1 | 90.5 | 0.8 | 32.1 | >10 μM (Toxic at 30) | >10 μM (Toxic at 30) |
| 8 | STF-085811-1 (HPI-1) | No | No | 1.3 | 1.5 | 86 | 0.4 | 80.2 | 3 | 3 |
| 9 | STF-080835-1 | No | No | 5 | 5 | 86.5 | 0.8 | −26.9 | >30 | >30 |
| 10 | STF-047200-1 | No | No | 2.2 | 2.2 | 78.8 | 4 | 81.8 | 2 | 4 |
| 11 | STF-031687-1 (HPI-3) | No | No | 2 | 1.5 | 76.7 | 2 | 70.7 | >30 | >30 |
| 12 | STF-120982-1 | No | No | 2 | 2 | 87.5 | 0.25 | Toxic at 20 | 4 | 15 |
| 13 | STF-023694-1 | No | No | 1.4 | 1.6 | 78.3 | 2.5 | Toxic at 15 | >30 | >30 |
| 14 | STF-023694-1 | No | No | 5.5 | 5.5 | 67.2 | 0.4 | 84.3 | >30 | 10 |
| 15 | STF-113777-1 | No | No | 4.5 | 5 | 86.9 | 4 | 89.1 | 12 | 25 |
| 16 | STF-120012-1 | No | No | 4.5 | 8 | 82.7 | 0.2 | 62.1 | >30 | >30 |
| 17 | STF-075501-1 (HPI-2) | No | No | 2 | 2 | 80.2 | 2 | 89.1 | >30 | 6 |
| 18 | STF-078717-1 (HPI-4) | No | No | 7.5 | 8 | 80 | 0.7 | 58.5 | >10 | >10 |

[a]As shown in FIG. 19

TABLE 2

| Compound Structure[a] | Compound Structure | BODIPY-cyclopamine competition | Microtubule disruption | IC50 (uM) Shh/Shh-LIGHT2 cells | IC50 (uM) SAG/Shh-LIGHT2 cells | % Inhibition Shh-GFP cells | IC50 (uM) Shh/C3HT10[1/2] cells | % Inhibition Su(fu)-/- MEFs | IC50 (uM) Gli1 Transfected or Infection | IC50 (uM) Gli2 Transfected |
|---|---|---|---|---|---|---|---|---|---|---|
| 8 | STF-085811-1 (HPI-1) | No | No | 1.3 | 1.5 | 86 | 0.4 | 80.2 | 3 | 3 |
| 19 | HPI-1.1 | | | >20 | >20 | | | | | |
| 20 | HPI-1.2 | | | 13 | 7.6 | | | | | |
| 21 | HPI-1.3 | | | 3.2 | | | | | | |
| 22 | HPI-1.4 | | | >20 | | | | | | |
| 23 | HPI-1.5 | | | >20 | | | | | | |
| 24 | HPI-1.6 | | | >20 | >20 | | | | | |
| 25 | HPI-1.7 | | | >20 | >20 | | | | | |
| 26 | HPI-1.8 | | | 4.8 | 5.3 | | | | | |
| 27 | HPI-1-9 | | | 7.2 | 6.1 | | | | | |
| 28 | HPI-1.10 | | | 8.1 | 9.4 | | | | | |
| 29 | HPI-1.11 | | | 0.98 | | | | | | |
| 30 | HPI-1.12 | | | 13 | | | | | | |
| 31 | HPI-1.13 | | | 1.5 | 1.7 | | | | | |
| 32 | HPI-1.14 | | | 2.3 | 3.2 | | | | | |
| 33 | HPI-1.15 | | | 0.67 | 0.71 | | | | | |
| 34 | HPI-1.16 | | | 1.1 | 1.2 | | | | | |
| 35 | HPI-1.17 | | | 0.76 | 2.8 | | | | | |
| 36 | HPI-1.18 | | | 3 | 2.1 | | | | | |
| 37 | HPI-1.19 | | | 0.74 | 1.1 | | | | | |
| 38 | HPI-1.20 | | | 1.2 | 1.1 | | | | | |
| 39 | HPI-1.21 | | | 2.9 | 2.9 | | | | | |
| 40 | HPI-1.22 | | | 2.1 | 2.3 | | | | | |
| 41 | HPI-1.23 | | | 1.3 | 2 | | | | | |
| 42 | HPI-1.24 | | | 6.3 | 7.8 | | | | | |
| 43 | HPI-1.25 | | | 3.3 | 3.9 | | | | | |
| 44 | HPI-1.26 | | | 3.8 | 7.9 | | | | | |
| 45 | HPi-1.27 | | | 1.4 | 2.2 | | | | | |
| 46 | HPI-1.28 | | | >20 | >20 | | | | | |
| 47 | HPI-1.29 | | | 11 | 12 | | | | | |
| 48 | HPI-1.30 | | | 2.7 | 2.4 | | | | | |

[a]As shown in FIGS. 20A and 20B

What is claimed is:

1. A method of inhibiting Hedgehog pathway signaling in a cell, the method comprising:
obtaining a cell or population of cells;
contacting the cell or population of cells with a compound having the formula:

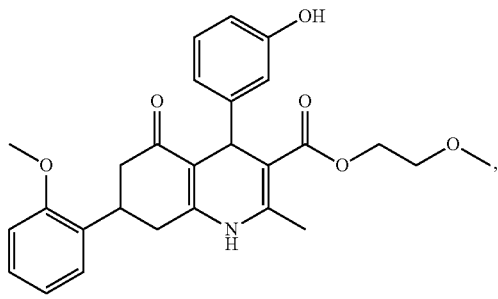

or a pharmaceutically acceptable salt thereof, in an amount effective to inhibit Hedgehog signaling in the cell, thereby inhibiting Hedgehog pathway signaling in the cell or population of cells.

2. The method of claim 1, wherein the inhibition of the hedgehog pathway signaling induces apoptosis in the cell or population of cells.

3. The method of claim 1, wherein the cell or population of cells is in a tissue of a human or animal subject, or isolated therefrom.

4. The method of claim 1, wherein the compound is in a pharmaceutically acceptable composition, wherein the pharmaceutically acceptable composition optionally further comprises a pharmaceutically acceptable carrier.

5. The method of claim 1, further comprising administering to the human or animal subject an effective amount of a second therapeutic agent.

* * * * *

UNITED STATES PATENT AND TRADEMARK OFFICE
CERTIFICATE OF CORRECTION

PATENT NO. : 8,119,640 B2  
APPLICATION NO. : 12/866338  
DATED : February 21, 2012  
INVENTOR(S) : Chen et al.

It is certified that error appears in the above-identified patent and that said Letters Patent is hereby corrected as shown below:

In The Specification

At column 1, lines 19-21, in the paragraph entitled "Statement Regarding Federally Sponsored Research or Development", delete:

"This disclosure was made with support under contract CA136574 awarded by the National Institutes of Health. The Government has certain rights in this invention."

and replace with:

"This invention was made with Government support under contract CA136574 awarded by the National Institutes of Health. The Government has certain rights in the invention."

Signed and Sealed this  
Fifteenth Day of March, 2016

Michelle K. Lee  
*Director of the United States Patent and Trademark Office*

SEQUENCE LISTING

<160> NUMBER OF SEQ ID NOS: 17

<210> SEQ ID NO 1
<211> LENGTH: 31
<212> TYPE: DNA
<213> ORGANISM: Artificial sequence
<220> FEATURE:
<223> OTHER INFORMATION: Primer

<400> SEQUENCE: 1
gtacgctagc atggtgagca agggcgagct g                                   31

<210> SEQ ID NO 2
<211> LENGTH: 32
<212> TYPE: DNA
<213> ORGANISM: Artificial sequence
<220> FEATURE:
<223> OTHER INFORMATION: Primer

<400> SEQUENCE: 2
gtacgtcgac tcacttgtac agctcgtcca tg                                  32

<210> SEQ ID NO 3
<211> LENGTH: 26
<212> TYPE: DNA
<213> ORGANISM: Artificial sequence
<220> FEATURE:
<223> OTHER INFORMATION: Primer -continued

```
<400> SEQUENCE: 3
gcgcctctcc cacatactag aaatct                                          26

<210> SEQ ID NO 4
<211> LENGTH: 26
<212> TYPE: DNA
<213> ORGANISM: Artificial sequence
<220> FEATURE:
<223> OTHER INFORMATION: Primer

<400> SEQUENCE: 4
taggaaatac catctgcttg gggttc                                          26

<210> SEQ ID NO 5
<211> LENGTH: 26
<212> TYPE: DNA
<213> ORGANISM: Artificial sequence
<220> FEATURE:
<223> OTHER INFORMATION: Primer

<400> SEQUENCE: 5
cacctgcatg ctagaggcaa actttt                                          26

<210> SEQ ID NO 6
<211> LENGTH: 26
<212> TYPE: DNA
<213> ORGANISM: Artificial sequence
<220> FEATURE:
<223> OTHER INFORMATION: Primer

<400> SEQUENCE: 6
tcaggcctag ttaacacttt gggaca                                          26

<210> SEQ ID NO 7
<211> LENGTH: 32
<212> TYPE: DNA
<213> ORGANISM: Artificial sequence
<220> FEATURE:
<223> OTHER INFORMATION: Primer

<400> SEQUENCE: 7
gaatgcggcc gcgttcaatc caatgactcc ac                                   32

<210> SEQ ID NO 8
<211> LENGTH: 27
<212> TYPE: DNA
<213> ORGANISM: Artificial sequence
<220> FEATURE:
<223> OTHER INFORMATION: Primer

<400> SEQUENCE: 8
gaagatcttt aggcactaga gttgagg                                         27

<210> SEQ ID NO 9
<211> LENGTH: 32
<212> TYPE: DNA
<213> ORGANISM: Artificial sequence
<220> FEATURE:
<223> OTHER INFORMATION: Primer

<400> SEQUENCE: 9
gaatgcggcc gcggagactt ctgccccagc cc                                   32

<210> SEQ ID NO 10
<211> LENGTH: 29
<212> TYPE: DNA
```

```
<213> ORGANISM: Artificial sequence
<220> FEATURE:
<223> OTHER INFORMATION: Primer

<400> SEQUENCE: 10
gaagatctta ggtcatcatg tttaaaaac                                    29

<210> SEQ ID NO 11
<211> LENGTH: 45
<212> TYPE: DNA
<213> ORGANISM: Artificial sequence
<220> FEATURE:
<223> OTHER INFORMATION: Primer

<400> SEQUENCE: 11
aaaaagcagc tcagccacc atggactaca aagaccatga cggtg                   45

<210> SEQ ID NO 12
<211> LENGTH: 37
<212> TYPE: DNA
<213> ORGANISM: Artificial sequence
<220> FEATURE:
<223> OTHER INFORMATION: Primer

<400> SEQUENCE: 12
agaaagctgg gtcttaggca ctagagttga ggaattg                           37

<210> SEQ ID NO 13
<211> LENGTH: 35
<212> TYPE: DNA
<213> ORGANISM: Artificial sequence
<220> FEATURE:
<223> OTHER INFORMATION: Primer

<400> SEQUENCE: 13
agaaagctgg gtcttaggtc atcatgttta aaaac                             35

<210> SEQ ID NO 14
<211> LENGTH: 31
<212> TYPE: DNA
<213> ORGANISM: Artificial sequence
<220> FEATURE:
<223> OTHER INFORMATION: Primer

<400> SEQUENCE: 14
ggggacaagt ttgtacaaaa aagcaggctc a                                 31

<210> SEQ ID NO 15
<211> LENGTH: 30
<212> TYPE: DNA
<213> ORGANISM: Artificial sequence
<220> FEATURE:
<223> OTHER INFORMATION: Primer

<400> SEQUENCE: 15
ggggaccact ttgtacaaga aagctgggtc                                   30

<210> SEQ ID NO 16
<211> LENGTH: 19
<212> TYPE: DNA
<213> ORGANISM: Artificial sequence
<220> FEATURE:
<223> OTHER INFORMATION: Primer

<400> SEQUENCE: 16
acagcggggg cagaagtcg                                               19
```

```
<210> SEQ ID NO 17
<211> LENGTH: 24
<212> TYPE: DNA
<213> ORGANISM: Artificial sequence
<220> FEATURE:
<223> OTHER INFORMATION: Primer

<400> SEQUENCE: 17
cctcagcccc agtatcccca gtcg                                            24
```